(12) United States Patent
Huang et al.

(10) Patent No.: US 12,371,491 B2
(45) Date of Patent: Jul. 29, 2025

(54) ANTI-TIGIT IMMUNOSUPPRESSANT AND APPLICATION THEREOF

(71) Applicant: Bio-Thera Solutions, Ltd., Guangdong (CN)

(72) Inventors: Junjie Huang, Guangzhou (CN); Xiaoyun Wu, Guangzhou (CN); Zhenqian Xu, Guangzhou (CN); Shide Liang, Guangzhou (CN); Shengfeng Li, Guangzhou (CN); Jin-Chen Yu, Guangzhou (CN); Xianming Huang, Guangzhou (CN)

(73) Assignee: Bio-Thera Solutions, Ltd., Guangzhou (CN)

( * ) Notice: Subject to any disclaimer, the term of this patent is extended or adjusted under 35 U.S.C. 154(b) by 820 days.

(21) Appl. No.: 17/639,877

(22) PCT Filed: Sep. 3, 2020

(86) PCT No.: PCT/CN2020/113200
§ 371 (c)(1),
(2) Date: Mar. 2, 2022

(87) PCT Pub. No.: WO2021/043206
PCT Pub. Date: Mar. 11, 2021

(65) Prior Publication Data
US 2022/0348650 A1 Nov. 3, 2022

(30) Foreign Application Priority Data

Sep. 3, 2019 (WO) ............... PCT/CN2019/104258

(51) Int. Cl.
| | | |
|---|---|---|
| C07K 16/00 | (2006.01) | |
| A61K 39/00 | (2006.01) | |
| A61P 35/00 | (2006.01) | |
| C07K 16/28 | (2006.01) | |

(52) U.S. Cl.
CPC .......... *C07K 16/2803* (2013.01); *A61P 35/00* (2018.01); *C07K 2317/24* (2013.01); *C07K 2317/515* (2013.01); *C07K 2317/52* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| | | |
|---|---|---|
| 9,290,577 B2 | 3/2016 | Hudson et al. |
| 2017/0088613 A1 | 3/2017 | Grogan et al. |
| 2017/0165366 A1 | 6/2017 | Hicklin et al. |
| 2018/0371083 A1 | 12/2018 | Williams et al. |

FOREIGN PATENT DOCUMENTS

| | | |
|---|---|---|
| CN | 1303430 A | 7/2001 |
| CN | 1307484 A | 8/2001 |
| CN | 102149825 A | 8/2011 |
| CN | 102958537 A | 3/2013 |
| CN | 107428834 A | 12/2017 |
| CN | 109071656 A | 12/2018 |
| JP | 2018527919 A | 9/2018 |
| JP | 2018532397 A | 11/2018 |
| JP | 2018533371 A | 11/2018 |
| WO | 2020257760 A1 | 12/2020 |

OTHER PUBLICATIONS

Office Action in Japanese Application No. 2022-514242, mailed Jul. 16, 2024, 11 pages.
International Search Report for PCT/CN2020/113200, filed Sep. 3, 2020, Date of Mailing of International Search Report Dec. 7, 2020, (16 pages).
Database Geneseq [Online] "Anti-TIGIT monoclonal antibody light chain variable domain, SEQ 412.", XP002809865, retrieved from EBI accession No. GSP:BIU07367 Database accession No. BIU07367, Feb. 4, 2021 (Feb. 4, 2021), 1 page.
Wang et al., "Immune checkpoint blockade and its combination therapy with small-molecule inhibitors for cancer treatment" Biochimica Et Biophysica Acta (BBA)—Reviews on Cancer, Elsevier Science BV, Amsterdam, NL, vol. 1871, No. 2, Apr. 1, 2019 (Apr. 1, 2019), pp. 199-224, XP085692939.

*Primary Examiner* — Misook Yu
*Assistant Examiner* — Imma Barrera
(74) *Attorney, Agent, or Firm* — Sheppard Mullin Richter & Hampton LLP

(57) ABSTRACT

The present invention provides an anti-TIGIT immunosuppressant and use thereof. The immunosuppressant can bind to the extracellular region of human TIGIT, and can be used for treating diseases such as a cancer.

16 Claims, 16 Drawing Sheets
Specification includes a Sequence Listing.

SEQUENCE LISTING

<160> NUMBER OF SEQ ID NOS: 57

<210> SEQ ID NO 1
<211> LENGTH: 343

```
<212> TYPE: PRT
<213> ORGANISM: Artificial Sequence
<220> FEATURE:
<223> OTHER INFORMATION: Amino acid sequence of extracellular region of
      human PVR (CD155)

<400> SEQUENCE: 1

Met Ala Arg Ala Met Ala Ala Trp Pro Leu Leu Leu Val Ala Leu
1               5                   10                  15

Leu Val Leu Ser Trp Pro Pro Gly Thr Gly Asp Val Val Gln
            20                  25                  30

Ala Pro Thr Gln Val Pro Gly Phe Leu Gly Asp Ser Val Thr Leu Pro
        35                  40                  45

Cys Tyr Leu Gln Val Pro Asn Met Glu Val Thr His Val Ser Gln Leu
50                  55                  60

Thr Trp Ala Arg His Gly Glu Ser Gly Ser Met Ala Val Phe His Gln
65                  70                  75                  80

Thr Gln Gly Pro Ser Tyr Ser Glu Ser Lys Arg Leu Glu Phe Val Ala
                85                  90                  95

Ala Arg Leu Gly Ala Glu Leu Arg Asn Ala Ser Leu Arg Met Phe Gly
            100                 105                 110

Leu Arg Val Glu Asp Glu Gly Asn Tyr Thr Cys Leu Phe Val Thr Phe
        115                 120                 125

Pro Gln Gly Ser Arg Ser Val Asp Ile Trp Leu Arg Val Leu Ala Lys
130                 135                 140

Pro Gln Asn Thr Ala Glu Val Gln Lys Val Gln Leu Thr Gly Glu Pro
145                 150                 155                 160

Val Pro Met Ala Arg Cys Val Ser Thr Gly Gly Arg Pro Pro Ala Gln
                165                 170                 175

Ile Thr Trp His Ser Asp Leu Gly Gly Met Pro Asn Thr Ser Gln Val
            180                 185                 190

Pro Gly Phe Leu Ser Gly Thr Val Thr Val Thr Ser Leu Trp Ile Leu
        195                 200                 205

Val Pro Ser Ser Gln Val Asp Gly Lys Asn Val Thr Cys Lys Val Glu
210                 215                 220

His Glu Ser Phe Glu Lys Pro Gln Leu Leu Thr Val Asn Leu Thr Val
225                 230                 235                 240

Tyr Tyr Pro Pro Glu Val Ser Ile Ser Gly Tyr Asp Asn Asn Trp Tyr
                245                 250                 255

Leu Gly Gln Asn Glu Ala Thr Leu Thr Cys Asp Ala Arg Ser Asn Pro
            260                 265                 270

Glu Pro Thr Gly Tyr Asn Trp Ser Thr Thr Met Gly Pro Leu Pro Pro
        275                 280                 285

Phe Ala Val Ala Gln Gly Ala Gln Leu Leu Ile Arg Pro Val Asp Lys
290                 295                 300

Pro Ile Asn Thr Thr Leu Ile Cys Asn Val Thr Asn Ala Leu Gly Ala
305                 310                 315                 320

Arg Gln Ala Glu Leu Thr Val Gln Val Lys Glu Gly Pro Pro Ser Glu
                325                 330                 335

His Ser Gly Ile Ser Arg Asn
            340

<210> SEQ ID NO 2
<211> LENGTH: 1029
<212> TYPE: DNA
<213> ORGANISM: Artificial Sequence
```

<220> FEATURE:
<223> OTHER INFORMATION: DNA sequence of extracellular region of human
      PVR (CD155)

<400> SEQUENCE: 2

```
atggctagag ctatggctgc tgcttggcca ctgctgctgg tggccctgct ggtgctgtct    60
tggcccccte caggaaccgg cgacgtggtg gtgcaggctc aacccaggt gcctggcttc    120
ctgggcgatt ccgtgacact gccttgctac ctgcaggtgc aaacatgga ggtgacacac    180
gtgagccagc tgacatgggc tagacatgga gagtctggct ccatggccgt gttccaccag    240
acccagggcc ctagctactc tgagtccaag cgcctggagt ttgtggctgc tagactggga    300
gctgagctga ggaatgcttc cctgcggatg tttggcctga gtggagga cgagggcaat    360
tatacatgcc tgttcgtgac ctttccacag ggcagccggt ctgtggatat ctggctgaga    420
gtgctggcca agccccagaa cacagctgag gtgcagaagg tgcagctgac aggagagcct    480
gtgccaatgg ctagatgcgt gtccacaggc ggcaggcccc ctgctcagat cacctggcac    540
tctgacctgg gcggcatgcc caatacatct caggtcccag gcttcctgtc cggcaccgtg    600
acagtgacca gcctgtggat tctggtgcct tccagccagg tggatggcaa gaacgtgacc    660
tgcaaggtgg agcatgagag ctttgagaag ccacagctgc tgacagtgaa tctgaccgtg    720
tactatccac ccgaggtgtc catcagcggc tacgacaaca attggtatct gggccagaat    780
gaggccacac tgacctgtga tgctaggtct aaccctgagc aaccggcta taattggtcc    840
accacaatgg cccactgcc tccattcgct gtggctcagg agctcagct gctgatcaga    900
ccagtggaca gcccatcaa caccacactg atctgtaacg tgacaaatgc tctgggcgcc    960
agacaggctg agctgaccgt gcaggtgaag gagggccctc catctgagca ttccggcatc    1020
agccgcaat                                                           1029
```

<210> SEQ ID NO 3
<211> LENGTH: 141
<212> TYPE: PRT
<213> ORGANISM: Artificial Sequence
<220> FEATURE:
<223> OTHER INFORMATION: Human TIGIT sequence

<400> SEQUENCE: 3

```
Met Arg Trp Cys Leu Leu Leu Ile Trp Ala Gln Gly Leu Arg Gln Ala
1               5                  10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro
    130                 135                 140
```

<210> SEQ ID NO 4
<211> LENGTH: 245
<212> TYPE: PRT
<213> ORGANISM: Artificial Sequence
<220> FEATURE:
<223> OTHER INFORMATION: Monkey TIGIT sequence

<400> SEQUENCE: 4

```
Met Arg Trp Cys Leu Phe Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Lys Lys Gly Gly Ser Val Ile Leu Gln Cys His Leu Ser
        35                  40                  45

Ser Thr Met Ala Gln Val Thr Gln Val Asn Trp Glu Gln His Asp His
    50                  55                  60

Ser Leu Leu Ala Ile Arg Asn Ala Glu Leu Gly Trp His Ile Tyr Pro
65                  70                  75                  80

Ala Phe Lys Asp Arg Val Ala Pro Gly Pro Gly Leu Gly Leu Thr Leu
                85                  90                  95

Gln Ser Leu Thr Met Asn Asp Thr Gly Glu Tyr Phe Cys Thr Tyr His
            100                 105                 110

Thr Tyr Pro Asp Gly Thr Tyr Arg Gly Arg Ile Phe Leu Glu Val Leu
        115                 120                 125

Glu Ser Ser Val Ala Glu His Ser Ala Arg Phe Gln Ile Pro Leu Leu
    130                 135                 140

Gly Ala Met Ala Met Met Leu Val Val Ile Cys Ile Ala Val Ile Val
145                 150                 155                 160

Val Val Val Leu Ala Arg Lys Lys Lys Ser Leu Arg Ile His Ser Val
                165                 170                 175

Glu Ser Gly Leu Gln Arg Lys Ser Thr Gly Gln Glu Glu Ile Pro
            180                 185                 190

Ser Ala Pro Ser Pro Gly Ser Cys Val Gln Ala Glu Ala Ala Pro
        195                 200                 205

Ala Gly Leu Cys Gly Glu Gln Gln Gly Asp Asp Cys Ala Glu Leu His
    210                 215                 220

Asp Tyr Phe Asn Val Leu Ser Tyr Arg Ser Leu Gly Ser Cys Ser Phe
225                 230                 235                 240

Phe Thr Glu Thr Gly
                245
```

<210> SEQ ID NO 5
<211> LENGTH: 249
<212> TYPE: PRT
<213> ORGANISM: Artificial Sequence
<220> FEATURE:
<223> OTHER INFORMATION: Mouse TIGIT sequence

<400> SEQUENCE: 5

```
Met His Gly Trp Leu Leu Leu Val Trp Val Gln Gly Leu Ile Gln Ala
1               5                   10                  15

Ala Phe Leu Ala Thr Ala Ile Gly Ala Thr Ala Gly Thr Ile Asp Thr
            20                  25                  30

Lys Arg Asn Ile Ser Ala Glu Glu Gly Gly Ser Val Ile Leu Gln Cys
        35                  40                  45

His Phe Ser Ser Asp Thr Ala Glu Val Thr Gln Val Asp Trp Lys Gln
    50                  55                  60
```

Gln Asp Gln Leu Leu Ala Ile Tyr Ser Val Asp Leu Gly Trp His Val
65                  70                  75                  80

Ala Ser Val Phe Ser Asp Arg Val Val Pro Gly Pro Ser Leu Gly Leu
            85                  90                  95

Thr Phe Gln Ser Leu Thr Met Asn Asp Thr Gly Glu Tyr Phe Cys Thr
        100                 105                 110

Tyr His Thr Tyr Pro Gly Gly Ile Tyr Lys Gly Arg Ile Phe Leu Lys
    115                 120                 125

Val Gln Glu Ser Ser Asp Asp Arg Asn Gly Leu Ala Gln Phe Gln Thr
130                 135                 140

Ala Pro Leu Gly Gly Thr Met Ala Ala Val Leu Gly Leu Ile Cys Leu
145                 150                 155                 160

Met Val Thr Gly Val Thr Val Leu Ala Arg Lys Asp Lys Ser Ile Arg
                165                 170                 175

Met His Ser Ile Glu Ser Gly Leu Gly Arg Thr Glu Ala Glu Pro Gln
            180                 185                 190

Glu Trp Asn Leu Arg Ser Leu Ser Ser Pro Gly Ser Pro Val Gln Thr
        195                 200                 205

Gln Thr Ala Pro Ala Gly Pro Cys Gly Glu Gln Ala Glu Asp Asp Tyr
    210                 215                 220

Ala Asp Pro Gln Glu Tyr Phe Asn Val Leu Ser Tyr Arg Ser Leu Glu
225                 230                 235                 240

Ser Phe Ile Ala Val Ser Lys Thr Gly
                245

<210> SEQ ID NO 6
<211> LENGTH: 6
<212> TYPE: PRT
<213> ORGANISM: Artificial Sequence
<220> FEATURE:
<223> OTHER INFORMATION: Fusion protein linker

<400> SEQUENCE: 6

Ile Glu Gly Arg Met Asp
1               5

<210> SEQ ID NO 7
<211> LENGTH: 18
<212> TYPE: DNA
<213> ORGANISM: Artificial Sequence
<220> FEATURE:
<223> OTHER INFORMATION: DNA sequence of fusion protein linker

<400> SEQUENCE: 7
attgaaggta gaatggat                                                    18

<210> SEQ ID NO 8
<211> LENGTH: 126
<212> TYPE: PRT
<213> ORGANISM: Artificial Sequence
<220> FEATURE:
<223> OTHER INFORMATION: Heavy chain variable region of positive control
      antibody (Tiragolumab)

<400> SEQUENCE: 8

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
            35                  40                  45

Trp Leu Gly Lys Thr Tyr Tyr Arg Phe Lys Trp Tyr Ser Asp Tyr Ala
 50                  55                  60

Val Ser Val Lys Gly Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Phe Tyr Cys Thr Arg Glu Ser Thr Thr Tyr Asp Leu Leu Ala Gly Pro
            100                 105                 110

Phe Asp Tyr Trp Gly Gln Gly Thr Leu Val Thr Val Ser Ser
            115                 120                 125

<210> SEQ ID NO 9
<211> LENGTH: 113
<212> TYPE: PRT
<213> ORGANISM: Artificial Sequence
<220> FEATURE:
<223> OTHER INFORMATION: Light chain variable region of positive control
      antibody (Tiragolumab)

<400> SEQUENCE: 9

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Leu Tyr Ser
            20                  25                  30

Ser Asn Asn Lys Lys Tyr Leu Ala Trp Tyr Gln Gln Lys Pro Gly Gln
        35                  40                  45

Pro Pro Asn Leu Leu Ile Tyr Trp Ala Ser Thr Arg Glu Ser Gly Val
 50                 55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Phe Thr Phe Gly Pro Gly Thr Lys Val Glu Ile
            100                 105                 110

Lys

<210> SEQ ID NO 10
<211> LENGTH: 119
<212> TYPE: PRT
<213> ORGANISM: Artificial Sequence
<220> FEATURE:
<223> OTHER INFORMATION: Heavy chain variable region of positive anti-
      TIGIT antibody (10A7)

<400> SEQUENCE: 10

Glu Val Gln Leu Val Glu Ser Gly Gly Gly Leu Thr Gln Pro Gly Lys
1               5                   10                  15

Ser Leu Lys Leu Ser Cys Glu Ala Ser Gly Phe Thr Phe Ser Ser Phe
            20                  25                  30

Thr Met His Trp Val Arg Gln Ser Pro Gly Lys Gly Leu Glu Trp Val
        35                  40                  45

Ala Phe Ile Arg Ser Gly Ser Gly Ile Val Phe Tyr Ala Asp Ala Val
    50                  55                  60

Arg Gly Arg Phe Thr Ile Ser Arg Asp Asn Ala Lys Asn Leu Leu Phe
65                  70                  75                  80

Leu Gln Met Asn Asp Leu Lys Ser Glu Asp Thr Ala Met Tyr Tyr Cys 85                  90                  95
Ala Arg Arg Pro Leu Gly His Asn Thr Phe Asp Ser Trp Gly Gln Gly
                100                 105                 110
Thr Leu Val Thr Val Ser Ser
        115

<210> SEQ ID NO 11
<211> LENGTH: 114
<212> TYPE: PRT
<213> ORGANISM: Artificial Sequence
<220> FEATURE:
<223> OTHER INFORMATION: Light chain variable region of positive anti-
      TIGIT antibody (10A7)

<400> SEQUENCE: 11

Asp Ile Val Met Thr Gln Ser Pro Ser Ser Leu Ala Val Ser Pro Gly
1               5                   10                  15

Glu Lys Val Thr Met Thr Cys Lys Ser Ser Gln Ser Leu Tyr Tyr Ser
                20                  25                  30

Gly Val Lys Glu Asn Leu Leu Ala Trp Tyr Gln Gln Lys Pro Gly Gln
        35                  40                  45

Ser Pro Lys Leu Leu Ile Tyr Tyr Ala Ser Ile Arg Phe Thr Gly Val
    50                  55                  60

Pro Asp Arg Phe Thr Gly Ser Gly Ser Gly Thr Asp Tyr Thr Leu Thr
65                  70                  75                  80

Ile Thr Ser Val Gln Ala Glu Asp Met Gly Gln Tyr Phe Cys Gln Gln
                85                  90                  95

Gly Ile Asn Asn Pro Leu Thr Phe Gly Asp Gly Thr Lys Leu Glu Ile
                100                 105                 110

Lys Arg

<210> SEQ ID NO 12
<211> LENGTH: 19
<212> TYPE: PRT
<213> ORGANISM: Artificial Sequence
<220> FEATURE:
<223> OTHER INFORMATION: Humanized antibody heavy chain signal peptide

<400> SEQUENCE: 12

Met Glu Phe Gly Leu Ser Trp Val Phe Leu Val Ala Ile Leu Lys Gly
1               5                   10                  15

Val Gln Cys

<210> SEQ ID NO 13
<211> LENGTH: 57
<212> TYPE: DNA
<213> ORGANISM: Artificial Sequence
<220> FEATURE:
<223> OTHER INFORMATION: DNA sequence of humanized antibody light chain
      signal peptide

<400> SEQUENCE: 13
atggagtttg ggctgagctg ggttttcctt gttgctatat taaaaggtgt ccagtgt       57

<210> SEQ ID NO 14
<211> LENGTH: 22
<212> TYPE: PRT
<213> ORGANISM: Artificial Sequence
<220> FEATURE:
<223> OTHER INFORMATION: Amino acid sequence of humanized antibody light
      chain signal peptide

```
<400> SEQUENCE: 14

Met Asp Met Arg Val Leu Ala Gln Leu Leu Gly Leu Leu Leu Leu Cys
1               5                   10                  15

Phe Pro Gly Ala Arg Cys
            20

<210> SEQ ID NO 15
<211> LENGTH: 66
<212> TYPE: DNA
<213> ORGANISM: Artificial Sequence
<220> FEATURE:
<223> OTHER INFORMATION: DNA sequence of humanized antibody light chain
      signal peptide

<400> SEQUENCE: 15
atggacatga gggtgctggc ccagctgctg ggactgctgc tgctgtgctt cccaggcgcc    60
agatgc                                                               66

<210> SEQ ID NO 16
<211> LENGTH: 19
<212> TYPE: PRT
<213> ORGANISM: Artificial Sequence
<220> FEATURE:
<223> OTHER INFORMATION: Amino acid sequence of mouse anti-human TIGIT
      antibody light chain signal peptide

<400> SEQUENCE: 16

Met Lys Leu Pro Val Arg Leu Leu Val Leu Met Phe Trp Ile Pro Ala
1               5                   10                  15

Ser Ser Ser

<210> SEQ ID NO 17
<211> LENGTH: 60
<212> TYPE: DNA
<213> ORGANISM: Artificial Sequence
<220> FEATURE:
<223> OTHER INFORMATION: DNA sequence of mouse anti-human TIGIT antibody
      light chain signal peptide

<400> SEQUENCE: 17
atggagacag acacactcct gctatgggta ctgctgctct gggttccagg ttccactggt    60

<210> SEQ ID NO 18
<211> LENGTH: 19
<212> TYPE: PRT
<213> ORGANISM: Artificial Sequence
<220> FEATURE:
<223> OTHER INFORMATION: Amino acid sequence of mouse anti-human TIGIT
      antibody heavy chain signal peptide

<400> SEQUENCE: 18

Met Glu Arg His Trp Ile Phe Leu Phe Leu Phe Ser Val Thr Ala Gly
1               5                   10                  15

Val His Ser

<210> SEQ ID NO 19
<211> LENGTH: 57
<212> TYPE: DNA
<213> ORGANISM: Artificial Sequence
<220> FEATURE:
<223> OTHER INFORMATION: DNA sequence of mouse anti-human TIGIT antibody
      heavy chain signal peptide

<400> SEQUENCE: 19
```

```
atggagcggc actggatctt cctgttcctg ttctccgtga ccgccggcgt gcactcc          57
```

<210> SEQ ID NO 20
<211> LENGTH: 119
<212> TYPE: PRT
<213> ORGANISM: Artificial Sequence
<220> FEATURE:
<223> OTHER INFORMATION: Amino acid sequence of mouse anti-human TIGIT
      antibody m10D8 heavy chain variable region

<400> SEQUENCE: 20

Glu Val Lys Leu Gln Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Asn Pro Asp Lys Arg Leu Glu Leu Val
        35                  40                  45

Ala Thr Ile Asn Ser Asn Gly Gly Ser Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Leu Gly Thr Gly Thr Leu Gly Phe Ala Tyr Trp Gly Gln Gly
            100                 105                 110

Thr Leu Val Thr Val Ser Ser
        115

<210> SEQ ID NO 21
<211> LENGTH: 6
<212> TYPE: PRT
<213> ORGANISM: Artificial Sequence
<220> FEATURE:
<223> OTHER INFORMATION: m10D8 HCDR1

<400> SEQUENCE: 21

Ser Ser Tyr Gly Met Ser
1               5

<210> SEQ ID NO 22
<211> LENGTH: 17
<212> TYPE: PRT
<213> ORGANISM: Artificial Sequence
<220> FEATURE:
<223> OTHER INFORMATION: m10D8 HCDR2

<400> SEQUENCE: 22

Thr Ile Asn Ser Asn Gly Gly Ser Thr Tyr Tyr Pro Asp Ser Val Lys
1               5                   10                  15

Gly

<210> SEQ ID NO 23
<211> LENGTH: 10
<212> TYPE: PRT
<213> ORGANISM: Artificial Sequence
<220> FEATURE:
<223> OTHER INFORMATION: m10D8 HCDR3

<400> SEQUENCE: 23

Leu Gly Thr Gly Thr Leu Gly Phe Ala Tyr
1               5                   10

<210> SEQ ID NO 24
<211> LENGTH: 108
<212> TYPE: PRT
<213> ORGANISM: Artificial Sequence
<220> FEATURE:
<223> OTHER INFORMATION: Amino acid sequence of mouse anti-human TIGIT
      antibody m10D8 light chain variable region

<400> SEQUENCE: 24

Asp Ile Val Met Thr Gln Ala His Lys Phe Met Ser Thr Ser Gly Gly
1               5                   10                  15

Asp Arg Val Ser Ile Thr Cys Lys Ala Ser Gln Asp Val Lys Thr Ala
            20                  25                  30

Val Ser Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ser Thr Pro Trp
                85                  90                  95

Thr Phe Gly Gly Gly Thr Lys Leu Glu Ile Lys Arg
            100                 105

<210> SEQ ID NO 25
<211> LENGTH: 11
<212> TYPE: PRT
<213> ORGANISM: Artificial Sequence
<220> FEATURE:
<223> OTHER INFORMATION: m10D8 LCDR1

<400> SEQUENCE: 25

Lys Ala Ser Gln Asp Val Lys Thr Ala Val Ser
1               5                   10

<210> SEQ ID NO 26
<211> LENGTH: 7
<212> TYPE: PRT
<213> ORGANISM: Artificial Sequence
<220> FEATURE:
<223> OTHER INFORMATION: m10D8 LCDR2

<400> SEQUENCE: 26

Trp Ala Ser Thr Arg His Thr
1               5

<210> SEQ ID NO 27
<211> LENGTH: 9
<212> TYPE: PRT
<213> ORGANISM: Artificial Sequence
<220> FEATURE:
<223> OTHER INFORMATION: m10D8 LCDR3

<400> SEQUENCE: 27

Gln Gln His Tyr Ser Thr Pro Trp Thr
1               5

<210> SEQ ID NO 28
<211> LENGTH: 330
<212> TYPE: PRT
<213> ORGANISM: Artificial Sequence
<220> FEATURE:
<223> OTHER INFORMATION: Amino acid sequence of human IgG1 heavy chain
      constant region

```
<400> SEQUENCE: 28

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 29
<211> LENGTH: 330
<212> TYPE: PRT
<213> ORGANISM: Artificial Sequence
<220> FEATURE:
<223> OTHER INFORMATION: Amino acid sequence 2 of human IgG1 heavy chain
      constant region

<400> SEQUENCE: 29

Ala Ser Thr Lys Gly Pro Ser Val Phe Pro Leu Ala Pro Ser Ser Lys
1               5                   10                  15
```

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330
```

<210> SEQ ID NO 30
<211> LENGTH: 107
<212> TYPE: PRT
<213> ORGANISM: Artificial Sequence
<220> FEATURE:
<223> OTHER INFORMATION: Amino acid sequence of human IgG1 light chain
      constant region

<400> SEQUENCE: 30

```
Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45
```

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 31
<211> LENGTH: 330
<212> TYPE: PRT
<213> ORGANISM: Artificial Sequence
<220> FEATURE:
<223> OTHER INFORMATION: Amino acid sequence of mouse IgG2a heavy chain
      constant region

<400> SEQUENCE: 31

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
                20                  25                  30

Phe Pro Glu Pro Val Thr Leu Thr Trp Asn Ser Gly Ser Leu Ser Ser
            35                  40                  45

Gly Val His Thr Phe Pro Ala Val Leu Gln Ser Asp Leu Tyr Thr Leu
        50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn

```
                290                 295                 300
Ser Tyr Ser Cys Ser Val Val His Glu Gly Leu His Asn His His Thr
305                 310                 315                 320

Thr Lys Ser Phe Ser Arg Thr Pro Gly Lys
                325                 330
```

<210> SEQ ID NO 32
<211> LENGTH: 107
<212> TYPE: PRT
<213> ORGANISM: Artificial Sequence
<220> FEATURE:
<223> OTHER INFORMATION: Amino acid sequence of mouse IgG2a light chain
      constant region

<400> SEQUENCE: 32

```
Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105
```

<210> SEQ ID NO 33
<211> LENGTH: 119
<212> TYPE: PRT
<213> ORGANISM: Artificial Sequence
<220> FEATURE:
<223> OTHER INFORMATION: h10D8V1 heavy chain V region

<400> SEQUENCE: 33

```
Gln Val Gln Leu Gln Glu Ser Gly Gly Glu Leu Gly Lys Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Leu Val
        35                  40                  45

Ala Thr Ile Asn Ser Asn Gly Gly Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Tyr Cys
                85                  90                  95

Ala Arg Leu Gly Thr Gly Thr Leu Gly Phe Ala Tyr Trp Gly Gln Gly
            100                 105                 110

Thr Leu Val Thr Val Ser Ser
        115
```

<210> SEQ ID NO 34
<211> LENGTH: 107
<212> TYPE: PRT
<213> ORGANISM: Artificial Sequence

```
<220> FEATURE:
<223> OTHER INFORMATION: h10D8V1 light chain V region

<400> SEQUENCE: 34

Asp Ile Gln Met Thr Gln Ser Pro Ser Thr Leu Ser Ala Phe Val Gly
1               5                   10                  15

Asp Thr Ile Thr Ile Thr Cys Lys Ala Ser Gln Asp Val Lys Thr Ala
            20                  25                  30

Val Ser Trp Tyr Gln Gln Lys Pro Gly Gln Pro Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Tyr Thr Leu Thr Ile Ser Ser Leu Gln Ala
65              70                  75                  80

Glu Asp Val Ala Val Tyr Tyr Cys Gln Gln His Tyr Ser Thr Pro Trp
                85                  90                  95

Thr Phe Gly Gln Gly Thr Lys Val Asp Ile Lys
            100                 105

<210> SEQ ID NO 35
<211> LENGTH: 119
<212> TYPE: PRT
<213> ORGANISM: Artificial Sequence
<220> FEATURE:
<223> OTHER INFORMATION: h10D8OF heavy chain V region sequence

<400> SEQUENCE: 35

Gln Val Gln Leu Val Glu Ser Gly Gly Gly Val Val Gln Pro Gly Arg
1               5                   10                  15

Ser Leu Arg Leu Asp Cys Lys Ala Ser Gly Phe Thr Phe Ser Ser Tyr
            20                  25                  30

Gly Met Ser Trp Val Arg Gln Ala Pro Gly Lys Gly Leu Glu Leu Val
        35                  40                  45

Ala Thr Ile Asn Ser Asn Gly Ser Thr Tyr Tyr Pro Asp Ser Val
    50                  55                  60

Lys Gly Arg Phe Thr Ile Ser Arg Asp Asn Ser Lys Asn Thr Leu Phe
65              70                  75                  80

Leu Gln Met Asn Ser Leu Arg Ala Glu Asp Thr Ala Val Tyr Tyr Cys
                85                  90                  95

Ala Arg Leu Gly Thr Gly Thr Leu Gly Phe Ala Tyr Trp Gly Gln Gly
            100                 105                 110

Thr Leu Val Thr Val Ser Ser
        115

<210> SEQ ID NO 36
<211> LENGTH: 107
<212> TYPE: PRT
<213> ORGANISM: Artificial Sequence
<220> FEATURE:
<223> OTHER INFORMATION: h10D8OF light chain V region

<400> SEQUENCE: 36

Glu Ile Val Met Thr Gln Ser Pro Ala Thr Leu Ser Leu Ser Pro Gly
1               5                   10                  15

Glu Arg Ala Thr Leu Ser Cys Lys Ala Ser Gln Asp Val Lys Thr Ala
            20                  25                  30

Val Ser Trp Tyr Gln Gln Lys Pro Gly Gln Ala Pro Arg Leu Leu Ile
        35                  40                  45
```

Tyr Trp Ala Ser Thr Arg Ala Thr Gly Ile Pro Ala Arg Phe Ser Gly
                50                  55                  60

Ser Gly Ser Gly Thr Asp Tyr Thr Leu Thr Ile Ser Ser Leu Glu Pro
 65                  70                  75                  80

Glu Asp Phe Ala Val Tyr Tyr Cys Gln Gln His Tyr Ser Thr Pro Trp
                    85                  90                  95

Thr Phe Gly Gln Gly Thr Lys Val Glu Ile Lys
                100                 105

<210> SEQ ID NO 37
<211> LENGTH: 119
<212> TYPE: PRT
<213> ORGANISM: Artificial Sequence
<220> FEATURE:
<223> OTHER INFORMATION: h10D8V3 heavy chain V region

<400> SEQUENCE: 37

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Gly Met Ser Trp Val Arg Gln Ala Pro Gly Lys Gly Leu Glu Leu Val
                35                  40                  45

Ala Thr Ile Asn Ser Asn Gly Gly Ser Thr Tyr Tyr Pro Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Leu Gly Thr Gly Thr Leu Gly Phe Ala Tyr Trp Gly Gln Gly
                100                 105                 110

Thr Leu Val Thr Val Ser Ser
        115

<210> SEQ ID NO 38
<211> LENGTH: 107
<212> TYPE: PRT
<213> ORGANISM: Artificial Sequence
<220> FEATURE:
<223> OTHER INFORMATION: h10D8V3 light chain V region

<400> SEQUENCE: 38

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Lys Thr Ala
                20                  25                  30

Val Ser Trp Tyr Gln Gln Lys Pro Gly Lys Ala Pro Lys Leu Leu Ile
                35                  40                  45

Tyr Trp Ala Ser Thr Arg His Thr Gly Val Pro Ser Arg Phe Ser Gly
                50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln His Tyr Ser Thr Pro Trp
                    85                  90                  95

Thr Phe Gly Gly Gly Thr Lys Val Glu Ile Lys
                100                 105

<210> SEQ ID NO 39

<211> LENGTH: 119
<212> TYPE: PRT
<213> ORGANISM: Artificial Sequence
<220> FEATURE:
<223> OTHER INFORMATION: h10D8V4 heavy chain V region

<400> SEQUENCE: 39

Gln Val Gln Leu Gln Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Gly Met Ser Trp Val Arg Gln Ala Pro Gly Lys Gly Leu Glu Leu Val
        35                  40                  45
Ala Thr Ile Asn Ser Asn Gly Gly Ser Thr Tyr Tyr Pro Asp Ser Val
    50                  55                  60
Lys Gly Arg Phe Thr Ile Ser Arg Asp Asn Ala Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Leu Gly Thr Gly Thr Leu Gly Phe Ala Tyr Trp Gly Gln Gly
            100                 105                 110
Thr Leu Val Thr Val Ser Ser
        115

<210> SEQ ID NO 40
<211> LENGTH: 107
<212> TYPE: PRT
<213> ORGANISM: Artificial Sequence
<220> FEATURE:
<223> OTHER INFORMATION: h10D8V4 light chain V region

<400> SEQUENCE: 40

Asp Ile Val Met Thr Gln Ser Pro Ser Thr Leu Ser Ala Ser Val Gly
1               5                   10                  15
Asp Arg Val Thr Ile Thr Cys Lys Ala Ser Gln Asp Val Lys Thr Ala
            20                  25                  30
Val Ser Trp Tyr Gln Gln Lys Pro Gly Gln Pro Pro Lys Leu Leu Ile
        35                  40                  45
Tyr Trp Ala Ser Thr Arg His Thr Gly Val Pro Asp Arg Phe Ser Gly
    50                  55                  60
Ser Gly Ser Gly Thr Asp Tyr Thr Leu Thr Ile Ser Ser Leu Gln Ala
65                  70                  75                  80
Glu Asp Val Ala Val Tyr Tyr Cys Gln Gln His Tyr Ser Thr Pro Trp
                85                  90                  95
Thr Phe Gly Gln Gly Thr Lys Val Glu Ile Lys
            100                 105

<210> SEQ ID NO 41
<211> LENGTH: 119
<212> TYPE: PRT
<213> ORGANISM: Artificial Sequence
<220> FEATURE:
<223> OTHER INFORMATION: h10D8V5 heavy chain V region

<400> SEQUENCE: 41

Gln Val Gln Leu Gln Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30

```
Gly Met Ser Trp Val Arg Gln Asn Pro Asp Lys Arg Leu Glu Leu Val
            35                  40                  45

Ala Thr Ile Asn Ser Asn Gly Gly Ser Thr Tyr Tyr Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Leu Gly Thr Gly Thr Leu Gly Phe Ala Tyr Trp Gly Gln Gly
            100                 105                 110

Thr Leu Val Thr Val Ser Ser
        115

<210> SEQ ID NO 42
<211> LENGTH: 107
<212> TYPE: PRT
<213> ORGANISM: Artificial Sequence
<220> FEATURE:
<223> OTHER INFORMATION: h10D8V5 light chain V region

<400> SEQUENCE: 42

Asp Ile Val Met Thr Gln Ser Pro Lys Thr Leu Ser Ala Ser Val Gly
1               5                   10                  15

Asp Arg Val Thr Ile Thr Cys Lys Ala Ser Gln Asp Val Lys Thr Ala
            20                  25                  30

Val Ser Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Tyr Thr Leu Thr Ile Ser Ser Leu Gln Ala
65                  70                  75                  80

Glu Asp Val Ala Leu Tyr Tyr Cys Gln Gln His Tyr Ser Thr Pro Trp
                85                  90                  95

Thr Phe Gly Gly Gly Thr Lys Val Glu Ile Lys
            100                 105

<210> SEQ ID NO 43
<211> LENGTH: 7
<212> TYPE: PRT
<213> ORGANISM: Artificial Sequence
<220> FEATURE:
<223> OTHER INFORMATION: LCDR2 mutant

<400> SEQUENCE: 43

Trp Ala Ser Thr Arg Ala Thr
1               5

<210> SEQ ID NO 44
<211> LENGTH: 449
<212> TYPE: PRT
<213> ORGANISM: Artificial Sequence
<220> FEATURE:
<223> OTHER INFORMATION: h10D8OF heavy chain

<400> SEQUENCE: 44

Gln Val Gln Leu Val Glu Ser Gly Gly Gly Val Val Gln Pro Gly Arg
1               5                   10                  15

Ser Leu Arg Leu Asp Cys Lys Ala Ser Gly Phe Thr Phe Ser Ser Tyr
            20                  25                  30

Gly Met Ser Trp Val Arg Gln Ala Pro Gly Lys Gly Leu Glu Leu Val
```

```
                35                  40                  45
Ala Thr Ile Asn Ser Asn Gly Gly Ser Thr Tyr Tyr Pro Asp Ser Val
 50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Arg Leu Gly Thr Gly Thr Leu Gly Phe Ala Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys
```

```
<210> SEQ ID NO 45
<211> LENGTH: 214
<212> TYPE: PRT
<213> ORGANISM: Artificial Sequence
<220> FEATURE:
<223> OTHER INFORMATION: h10D8OF light chain

<400> SEQUENCE: 45

Glu Ile Val Met Thr Gln Ser Pro Ala Thr Leu Ser Leu Ser Pro Gly
1               5                   10                  15

Glu Arg Ala Thr Leu Ser Cys Lys Ala Ser Gln Asp Val Lys Thr Ala
            20                  25                  30

Val Ser Trp Tyr Gln Gln Lys Pro Gly Gln Ala Pro Arg Leu Leu Ile
        35                  40                  45

Tyr Trp Ala Ser Thr Arg Ala Thr Gly Ile Pro Ala Arg Phe Ser Gly
    50                  55                  60

Ser Gly Ser Gly Thr Asp Tyr Thr Leu Thr Ile Ser Ser Leu Glu Pro
65                  70                  75                  80

Glu Asp Phe Ala Val Tyr Tyr Cys Gln Gln His Tyr Ser Thr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 46
<211> LENGTH: 1350
<212> TYPE: DNA
<213> ORGANISM: Artificial Sequence
<220> FEATURE:
<223> OTHER INFORMATION: Nucleotide sequence of h10D8OF heavy chain

<400> SEQUENCE: 46
caggtgcagc tggtggagtc cggcggcgga gtggtgcagc tggaaggtc cctgagactg      60 gactgtaagg ccagcggctt cacctttagc agctacggca tgagctgggt gagacaggcc    120
cctggcaagg gcctggagct ggtggctacc atcaatagca tggcggcag cacctactac    180 cccgacagcg tgaagggcag attcactatc agcagagaca actccaagaa taccctgttc    240
ctgcagatga atagcctgag agccgaggac accgccgtgt actactgcgc caggctgggc    300
accggcaccc tgggatttgc ctactggggc cagggtaccc tggttaccgt tagcagcgcg    360
agcaccaaag gcccgagcgt gtttccgctg ggccccgagca gcaaaagcac cagcggtggc    420
accgcagcgc tgggttgcct ggtgaaagat tatttcccgg aaccggtgac ggtgtcgtgg    480
aactcaggcg ccctgaccag cggcgtgcac accttcccgg ctgtcctaca gtcctcagga    540
```

-continued

```
ctctactccc tcagcagcgt ggtgaccgtg ccctccagca gcttgggcac ccagacctac      600
atctgcaacg tgaatcacaa gcccagcaac accaaggtgg acaagaaagt tgagcccaaa      660
tcttgtgaca aaactcacac atgcccaccg tgcccagcac ctgaactcct ggggggaccg      720
tcagtcttcc tcttccccc aaaacccaag gacaccctca tgatctcccg gacccctgag       780
gtcacatgcg tggtggtgga cgtgagccac gaagaccctg aggtcaagtt caactggtac      840
gtggacggcg tggaggtgca taatgccaag acaaagccgc gggaggagca gtacaacagc      900
acgtaccgtg tggtcagcgt cctcaccgtc ctgcaccagg actggctgaa tggcaaggag      960
tacaagtgca aggtctccaa caaagccctc ccagccccca tcgagaaaac catctccaaa     1020
gccaaagggc agccccgaga accacaggtg tacaccctgc ccccatcccg ggatgagctg     1080
accaagaacc aggtcagcct gacctgcctg gtcaaaggct tctatcccag cgacatcgcc     1140
gtggagtggg agagcaatgg gcagccggag aacaactaca agaccacgcc tcccgtgctg     1200
gactccgacg gctccttctt cctctacagc aagctcaccg tggacaagag caggtggcag     1260
caggggaacg tcttctcatg ctccgtgatg catgaggctc tgcacaacca ctacacgcag     1320
aagagcctct ccctgtctcc gggtaaatga                                      1350
```

<210> SEQ ID NO 47
<211> LENGTH: 645
<212> TYPE: DNA
<213> ORGANISM: Artificial Sequence
<220> FEATURE:
<223> OTHER INFORMATION: Nucleotide sequence of h10D8OF light chain

<400> SEQUENCE: 47

```
gagatcgtga tgacccagag ccccgccacc ctgtccctga gcccaggaga gagagccacc       60
ctgagctgca aggcctccca ggacgtgaag accgccgtga gctggtatca acagaagcct      120
ggccaggccc ccagactgct gatctactgg gcctccacca gggccaccgg catccctgct      180
agattcagcg gctccggctc cggcaccgat tacaccctga ccatcagcag cctggagcct      240
gaggatttcg ccgtgtacta ctgtcagcag cactactcca ccccttggac cttcggccag      300
ggcaccaagg tggagatcaa gcgtacggtg gctgcaccat ctgtcttcat cttcccgcca      360
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gttga                     645
```

<210> SEQ ID NO 48
<211> LENGTH: 423
<212> TYPE: DNA
<213> ORGANISM: Artificial Sequence
<220> FEATURE:
<223> OTHER INFORMATION: Nucleotide sequence of human TIGIT

<400> SEQUENCE: 48

```
atgcgctggt gtctgctgct gatttgggcc caggactga dacaggctcc tctggcttca       60
ggaatgatga ccggcaccat cgagaccacc ggaaacatca gcgccgagaa gggaggaagc      120
atcatcctcc agtgccacct gagtagcaca accgcacagg tcacccaggt caattgggag      180
cagcaggacc agctgctggc catttgcaac gccgatctgg gttggcacat ctctcctagc      240
```

```
ttcaaggaca gagtggcccc aggaccagga ctgggactga cactgcagag tctgaccgtg    300
aacgacaccg gcgagtactt ctgcatctac cacacctacc cagacggcac ctacacagga    360
cggatcttcc tggaggtgct ggagtctagc gtggcagagc acggagccag attccagatc    420
cct                                                                  423
```

<210> SEQ ID NO 49
<211> LENGTH: 990
<212> TYPE: DNA
<213> ORGANISM: Artificial Sequence
<220> FEATURE:
<223> OTHER INFORMATION: Nucleotide sequence of mouse IgG2a heavy chain
      constant region

<400> SEQUENCE: 49

```
gccaagacca ccgcccctag cgtgtaccct ctggcccctg tgtgtggcga taccaccggc     60
tcctccgtga ccctgggctg tctggtgaag ggctacttcc ctgagcccgt gaccctgacc    120
tggaatagcg gcagcctgag cagcggcgtg cacaccttcc cgccgtgct gcagtccgac    180 ctgtacaccc tgtcctccag cgtgaccgtg acctcctcca cctggcctag ccagagcatc    240
acctgcaacg tggctcaccc cgctagcagc accaaggtgg acaagaagat cgagcccagg    300
ggccctacca tcaagccttg ccctccctgc aagtgccccg ctcctaacct gctgggcggc    360
ccaagcgtgt tcatctttcc ccccaagatc aaggatgtgc tgatgatcag cctgagcccc    420
atcgtgacct gtgtggtggt ggacgtgtcc gaggatgatc cgatgtgca gatcagctgg    480 ttcgtgaaca acgtggaggt gcacaccgct cagacccaga cccaccggga ggactataat    540
agcaccctga gggtggtgag cgctctgcct atccagcacc aggactggat gtccggcaag    600
gagtttaagt gtaaggtgaa caacaaggat ctgcccgccc catcgagcg gaccatcagc    660 aagcccaagg gcagcgtgcg ggcccctcag gtttatgtgc tgccccccc tgaggaggag    720 atgaccaaga gcaggtgac cctgacatgc atggtgaccg actttatgcc cgaggatatc    780
tacgtggagt ggaccaacaa tggcaagacc gagctgaact acaagaacac cgagcccgtg    840
ctggattccg acggcagcta tttcatgtac tccaagctgc gggtggagaa gaagaactgg    900
gtggagcgga acagctatag ctgctccgtg gtgcacgagg cctgcacaa ccaccacacc    960 accaagagct tttcccggac ccccggtaaa                                    990
```

<210> SEQ ID NO 50
<211> LENGTH: 321
<212> TYPE: DNA
<213> ORGANISM: Artificial Sequence
<220> FEATURE:
<223> OTHER INFORMATION: Nucleotide sequence of mouse IgG2a light chain
      constant region

<400> SEQUENCE: 50

```
cgtgctgacg ccgcccctac cgtgagcatc tttcctccct ccagcgagca gctgaccagc     60
ggcggagcct ccgtggtgtg ctttctgaac aactttatc ctaaggacat caatgtgaag    120
tggaagatcg atggctccga gaggcagaat ggcgtgctga actcctggac cgatcaggac    180
tccaaggact ccacctactc catgtccagc accctgaccc tgaccaagga tgagtatgag    240
cggcacaatt cctatacctg tgaggctacc cacaagacca gcacctcccc tatcgtgaag    300
agcttcaata ggaacgagtg t                                             321
```

<210> SEQ ID NO 51
<211> LENGTH: 366

```
<212> TYPE: DNA
<213> ORGANISM: Artificial Sequence
<220> FEATURE:
<223> OTHER INFORMATION: Heavy chain variable region of mouse anti-human
      CD3 single-chain antibody

<400> SEQUENCE: 51
gtgctagccc aggtccagct gcagcagtct ggggctgaac tggcaagacc tggggcctca      60
gtgaagatgt cctgcaaggc ttctggctac acctttacta ggtacacgat gcactgggta     120
aaacagaggc ctggacaggg tctggaatgg attggataca ttaatcctag ccgtggttat     180
actaattaca atcagaagtt caaggacaag gccacattga ctacagacaa atcctccagc     240
acagcctaca tgcaactgag cagcctgaca tctgaggact ctgcagtcta ttactgtgca     300
agatattatg atgatcatta ctgccttgac tactggggcc aaggcaccac ggtgaccgtg     360
agcgcc                                                                366

<210> SEQ ID NO 52
<211> LENGTH: 45
<212> TYPE: DNA
<213> ORGANISM: Artificial Sequence
<220> FEATURE:
<223> OTHER INFORMATION: Linker

<400> SEQUENCE: 52
gggggaggtg gcagcggggg aggtggcagc ggcggcggga gctcc                      45

<210> SEQ ID NO 53
<211> LENGTH: 381
<212> TYPE: DNA
<213> ORGANISM: Artificial Sequence
<220> FEATURE:
<223> OTHER INFORMATION: Light chain variable region of mouse anti-human
      CD3 single-chain antibody

<400> SEQUENCE: 53
gggggaggtg gcagcggggg aggtggcagc ggcggcggga gctcccaaat tgttctcacc      60
cagtctccag caatcatgtc tgcatctcca ggggagaagg tcaccatgac ctgcagtgcc     120
agctcaagtg taagttacat gaactggtac cagcagaagt caggcacctc ccccaaaaga     180
tggatttatg acacatccaa actggcttct ggagtccctg ctcacttcag gggcagtggg     240
tctgggacct cttactctct cacaatcagc ggcatggagg ctgaagatgc tgccacttat     300
tactgccagc agtggagtag taacccattc acgttcggct cggggacaaa gttggaaata     360
aaccggggcg gtggggatcc c                                                381

<210> SEQ ID NO 54
<211> LENGTH: 1254
<212> TYPE: DNA
<213> ORGANISM: Artificial Sequence
<220> FEATURE:
<223> OTHER INFORMATION: Full-length PVR nucleotide sequence

<400> SEQUENCE: 54
atggctagag ctatggctgc tgcttggcca ctgctgctgg tggccctgct ggtgctgtct      60 tggcccccctc caggaaccgg cgacgtgtg gtgcaggctc aacccaggt gcctggcttc     120 ctgggcgatt ccgtgacact gccttgctac ctgcaggtgc aaacatgga ggtgacacac     180 gtgagccagc tgcatgggc tagacatgga gagtctggct ccatgccgt gttccaccag     240 acccagggcc ctagctactc tgagtccaag cgcctggagt tgtggctgc tagactggga     300
```

```
gctgagctga ggaatgcttc cctgcggatg tttggcctga gagtggagga cgagggcaat      360
tatacatgcc tgttcgtgac ctttccacag ggcagccggt ctgtggatat ctggctgaga      420
gtgctggcca agccccagaa cacagctgag gtgcagaagg tgcagctgac aggagagcct      480
gtgccaatgg ctagatgcgt gtccacaggc ggcaggcccc ctgctcagat cacctggcac      540
tctgacctgg gcggcatgcc caatacatct caggtcccag gcttcctgtc cggcaccgtg      600
acagtgacca gcctgtggat tctggtgcct tccagccagg tggatggcaa gaacgtgacc      660
tgcaaggtgg agcatgagag cttgagaag ccacagctgc tgacagtgaa tctgaccgtg      720
tactatccac ccgaggtgtc catcagcggc tacgacaaca attggtatct gggccagaat      780
gaggccacac tgacctgtga tgctaggtct aaccctgagc caaccggcta taattggtcc      840
accacaatgg gcccactgcc tccattcgct gtggctcagg gagctcagct gctgatcaga      900
ccagtggaca agcccatcaa caccacactg atctgtaacg tgacaaatgc tctgggcgcc      960
agacaggctg agctgaccgt gcaggtgaag gagggccctc catctgagca ttccggcatc     1020
agccgcaatg ccattatctt cctggtgctg ggcatcctgg tgttcctgat cctgctggga     1080
atcggcatct acttctactg gtccaagtgc tccaggaggg tgctgtggca ttgccatctg     1140
tgcccttcct ccaccgagca tgcttctgct tccgctaacg ccacgtgtc ttactccgct     1200 gtgtccagag agaactcctc ctcccaggac cctcagacag agggcaccag gtga           1254

<210> SEQ ID NO 55
<211> LENGTH: 735
<212> TYPE: DNA
<213> ORGANISM: Artificial Sequence
<220> FEATURE:
<223> OTHER INFORMATION: Full-length human TIGIT nucleotide sequence

<400> SEQUENCE: 55
atgcgctggt gtctgctgct gatttgggcc cagggactga cacaggctcc tctggcttca       60
ggaatgatga ccggcaccat cgagaccacc ggaaacatca cgccgagaa ggaggaagc       120 atcatcctcc agtgccacct gagtagcaca accgcacagg tcacccaggt caattgggag      180
cagcaggacc agctgctggc catttgcaac gccgatctgg gttggcacat ctctcctagc      240
ttcaaggaca gagtggcccc aggaccagga ctgggactga cactgcagag tctgaccgtg      300
aacgacaccg cgagtactt ctgcatctac cacacctacc cagacggcac ctacacagga      360
cggatcttcc tggaggtgct ggagtctagc gtggcagagc acggagccag attccagatc      420
cctctgctgg gagctatggc agctacactg gtcgtgatct gcaccgcagt gatcgtggtc      480
gtggctctga cacggaagaa gaaggcctg agaatccaca gcgtggaggg agacctgaga      540
agaaagagcg ccggacagga ggagtggtct cctagcgctc cttctcctcc aggctcttgt      600
gtgcaggcag aagcagctcc agcaggtctc tgcggagaac agagaggaga ggattgcgcc      660
gagctgcacg actacttcaa cgtgctgagc taccggagcc tgggcaattg cagcttcttc      720
accgagaccg gatga                                                      735

<210> SEQ ID NO 56
<211> LENGTH: 1011
<212> TYPE: DNA
<213> ORGANISM: Artificial Sequence
<220> FEATURE:
<223> OTHER INFORMATION: Full-length human CD226 nucleotide sequence

<400> SEQUENCE: 56
atggactacc ccaccctgct gctggccctg ctgcacgtgt acagggccct gtgcgaggag       60
```

```
gtgctgtggc acacaagcgt gcctttcgcc gagaacatga gcctggagtg cgtgtaccct      120
agcatgggca tcctgaccca ggtggagtgg ttcaagatcg gcacccagca ggattccatc      180
gccatcttta gccccacaca cggcatggtg atcaggaagc cttacgccga gagagtgtac      240
ttcctgaata gcaccatggc cagcaataat atgaccctgt tctttagaaa cgcctccgag      300
gatgacgtgg gctactactc ctgttccctg tacacctacc ctcagggcac ctggcagaag      360
gtgatccagg tggtgcagtc cgatagcttt gaggccgccg tgccttccaa ctcccacatc      420
gtgagcgagc ccggcaagaa tgtgacactg acatgccagc ccagatgac ctggcccgtg       480 caggccgtga ggtgggagaa gatccagcct aggcagatcg atctgctgac ctactgtaat      540
ctggtgcacg gcagaaactt caccagcaag ttccccagac agatcgtgtc caattgttcc      600
cacggcaggt ggagcgtgat cgtgatccct gatgtgacag tgtccgactc cggcctgtac      660
agatgctacc tgcaggccag cgccggcgag aacgagacct tcgtgatgag actgaccgtg      720
gccgagggca agaccgacaa tcagtacaca ctgtttgtgg ccggcggcac agtgctgctg      780
ctgctgttcg tgatcagcat caccacaatc atcgtgatct ttctgaatag aagaaggaga      840
agagagagga gagatctgtt cacagagagc tgggataccc agaaggcccc taataactac      900
aggtccccta tctccacatc ccagcctacc aatcagtcca tggatgatac aagggaggac      960
atctacgtga attaccctac attcagcaga agacctaaga ccagagtgtg a              1011

<210> SEQ ID NO 57
<211> LENGTH: 384
<212> TYPE: DNA
<213> ORGANISM: Artificial Sequence
<220> FEATURE:
<223> OTHER INFORMATION: IL-2 response element nucleotide sequence

<400> SEQUENCE: 57
ggtaccattt tctgagttac ttttgtatcc ccaccccctt aaagaaagga ggaaaaactg       60
tttcatacag aaggcgttaa ttgcatgaat tagagctatc acctaagtgt gggctaatgt      120
aacaaagagg gatttcacct catccattc agtcagtctt tgggggttta aagaaattcc      180
aaagagtcat cagaagagga aaaatgaagg taatgttttt tcagacaggt aaagtctttg      240
aaaatatgtg taatatgtaa aacattttga cacccccata atattttttcc agaattaaca      300 gtataaattg catctcttgt tcaagagttc cctatcactc tctttaatca ctactcacag      360
taacctcaac tcctgccaaa gctt                                              384
```

ANTI-TIGIT IMMUNOSUPPRESSANT AND APPLICATION THEREOF

CROSS REFERENCE TO RELATED APPLICATIONS

This application is a U.S. National Stage Application under 35 U.S.C. 371 of International Application No. PCT/CN2020/113200, filed Sep. 3, 2020, which claims priority to Application No. PCT/CN2019/104258, filed Sep. 3, 2019, the content of each of which is incorporated by reference in its entirety into the present disclosure.

SEQUENCE LISTING

The instant application contains a Sequence Listing which has been submitted electronically in ASCII format and is hereby incorporated by reference in its entirety. Said ASCII copy, created on Mar. 2, 2022, is named 349175US_ST25.txt and is 61.0 KB in size.

TECHNICAL FIELD

The present invention relates to the technical field of immunology, and in particular, to an immune checkpoint antibody, a method for preparing the same and use in immunology thereof.

BACKGROUND

TIGIT (T cell immunoreceptor with Ig and ITIM domains) is a T cell immunoreceptor with immunoglobulin (Ig) and immunoreceptor tyrosine inhibitor motif (ITIM) domains, and is expressed predominantly on activated T cells and NK cells (Yu, X., et al. (2009). "The surface protein TIGIT suppresses T cell activation by promoting the generation of mature immunoregulatory dendritic cells." *Nature immunology* 10(1): 48-57. ). TIGIT, also known as VSIG9, VSTM3 and WUCAM, is shown to structurally comprise an extracellular immunoglobulin domain, a type 1 transmembrane region and two ITIMs. TIGIT is a portion of a co-stimulatory network consisting essentially of an activating receptor CD226 and an inhibitory receptor TIGIT on T cells, and the ligands CD155 (also known as PVR, a poliovirus receptor protein encoded by the PVR gene in humans) and CD112 expressed on the surfaces of APCs, tumor cells and infected cells. Binding of TIGIT to PVR or CD112 results in phosphorylation of Tyr225 in TIGIT cytoplasm, and binding of TIGIT to cell adaptive growth factor receptor-bound protein 2 (GRB2). GRB2 recruits SHIP1 to inhibit phosphatidylinositol 3-kinase (PI3K) and mitogen-activated protein kinase (MAPK) signals. In addition, phosphorylated TIGIT recruits SHIP1 through beta arrestin2 (β-arrestin2) and disrupts nuclear factor κB (NF-κB) activation by blocking self-ubiquitination of TNF receptor-associated factor 6 (TRAF6). A series of signaling ultimately results in the inhibition of T cell or NK cell functions, and the inhibition of cytokine production. PVR is a ligand of TIGIT and CD226 molecules, and the affinity of CD226 and PVR molecules is 119 nM. Upon binding to CD112 or CD155, Ser329 and Tyr322 of the intracellular domain of CD226 were phosphorylated. Ser329 phosphorylation promotes activation of protein kinase C (PKC) and the binding of CD226 to lymphocyte function-associated antigen 1 (LFA1). LFA1 is then used for TYN-mediated Tyr322 phosphorylation and CD226-mediated downstream signaling. A series of signaling ultimately leads to activation of T cell or NK cell functions, promoting cytokine production. Interaction also occurs between TIGIT and CD226 molecules present on the surface of T cells or NK cells in that TIGIT molecules can directly perturb CD226 dimerization, thereby disrupting the normal physiological function of CD226. Therefore, TIGIT and CD226 are like two ends of a balance scale, and ingeniously regulate the immune function of the body via the co-stimulatory and co-inhibitory signaling through the fulcrum PVR.

A study exploring the correlation of TIGIT to natural killer (NK) cell dysfunction indicated that TIGIT is associated with NK cell depletion in tumor-bearing mice and in patients with colon cancer. Blocking TIGIT in several tumor-bearing mouse models could prevent NK cell apoptosis and promote NK cell-dependent tumor immunity. Furthermore, blocking TIGIT results in potent tumor-specific T cell immunity in an NK cell-dependent manner, enhancing anti-PD-L1 antibody efficacy and maintaining immunological memory in tumor re-challenge models. The work suggested that TIGIT constitutes an immune checkpoint on the surface of NK cells that is previously disregarded, and targeting TIGIT alone or in combination with other checkpoint receptors is a promising anti-cancer therapeutic strategy (Zhang, Q., et al. (2018). "Blockade of the checkpoint receptor TIGIT prevents NK cell exhaustion and elicits potent anti-tumor immunity." *Nature Immunology*). Since TIGIT is highly expressed on surfaces of both T cells and NK cells, and other immune checkpoints such as PD-1 and CTLA-4 are only expressed on the surfaces of T cells, TIGIT is superior as a therapeutic target, leading to therapeutic and marketing prospects for developing antibody drugs for this target.

SUMMARY

The present invention provides an anti-TIGIT antibody with high affinity for human TIGIT protein. In some embodiments, the anti-TIGIT antibody disclosed herein is an isolated anti-TIGIT antibody. In some embodiments, the anti-TIGIT antibody disclosed herein can effectively block the binding of TIGIT to PVR and can effectively activate lymphocytes to release cytokines. In some embodiments, the anti-TIGIT antibody disclosed herein has high affinity for human TIGIT and has suitable ADCC (antibody-dependent cellular cytotoxicity) activity. In some embodiments, the anti-TIGIT antibody disclosed herein can be used for therapeutic purposes such as treating various cancers and infections, and for diagnosis and prognosis.

In some embodiments, the present invention provides an antibody or an antigen-binding fragment thereof specifically binding to a T cell immunoreceptor with immunoglobulin and immunoreceptor tyrosine-based inhibitory motif domains (TIGIT), comprising one, two, three, four, five, or all of the following sequences:
  (a) a VH CDR1, comprising an amino acid sequence set forth in SEQ ID NO: 21, or an amino acid sequence with a substitution, deletion or insertion at a single site;
  (b) a VH CDR2, comprising an amino acid sequence set forth in SEQ ID NO: 22, or an amino acid sequence with a substitution, deletion or insertion at a single site;
  (c) a VH CDR3, comprising an amino acid sequence set forth in SEQ ID NO: 23, or an amino acid sequence with a substitution, deletion or insertion at a single site;
  (d) a VL CDR1, comprising an amino acid sequence set forth in SEQ ID NO: 25, or an amino acid sequence with a substitution, deletion or insertion at a single site;

(e) a VL CDR2, comprising an amino acid sequence set forth in SEQ ID NO: 26 or 43, or an amino acid sequence with a substitution, deletion or insertion at a single site; and (f) a VL CDR3, comprising an amino acid sequence set forth in SEQ ID NO: 27, or an amino acid sequence with a substitution, deletion or insertion at a single site.

In some embodiments, the present invention provides an isolated antibody or a fragment thereof specifically binding to a T cell immunoreceptor with immunoglobulin and immunoreceptor tyrosine-based inhibitory motif domains (TIGIT), comprising:

(a) a VH CDR1, comprising an amino acid sequence set forth in SEQ ID NO: 21, or an amino acid sequence with a substitution, deletion or insertion at a single site;

(b) a VH CDR2, comprising an amino acid sequence set forth in SEQ ID NO: 22, or an amino acid sequence with a substitution, deletion or insertion at a single site;

(c) a VH CDR3, comprising an amino acid sequence set forth in SEQ ID NO: 23, or an amino acid sequence with a substitution, deletion or insertion at a single site;

(d) a VL CDR1, comprising an amino acid sequence set forth in SEQ ID NO: 25, or an amino acid sequence with a substitution, deletion or insertion at a single site;

(e) a VL CDR2, comprising an amino acid sequence set forth in SEQ ID NO: 43, or an amino acid sequence with a substitution, deletion or insertion at a single site; and (f) a VL CDR3, comprising an amino acid sequence set forth in SEQ ID NO: 27, or an amino acid sequence with a substitution, deletion or insertion at a single site.

In some embodiments, the present invention provides an antibody or an antigen-binding fragment thereof specifically binding to a T cell immunoreceptor with immunoglobulin and immunoreceptor tyrosine-based inhibitory motif domains (TIGIT), comprising one, two, three, four, five, or all of a VH CDR1 set forth in SEQ ID NO: 21, a VH CDR2 set forth in SEQ ID NO: 22, a VH CDR3 set forth in SEQ ID NO: 23, a VL CDR1 set forth in SEQ ID NO: 25, a VL CDR2 set forth in SEQ ID NO: 26 or 43, and a VL CDR3 set forth in SEQ ID NO: 27.

In some embodiments, the present invention provides an antibody or an antigen-binding fragment thereof specifically binding to a T cell immunoreceptor with immunoglobulin and immunoreceptor tyrosine-based inhibitory motif domains (TIGIT), comprising a VH CDR1 set forth in SEQ ID NO: 21, a VH CDR2 set forth in SEQ ID NO: 22, a VH CDR3 set forth in SEQ ID NO: 23, a VL CDR1 set forth in SEQ ID NO: 25, a VL CDR2 set forth in SEQ ID NO: 26 or 43, and a VL CDR3 set forth in SEQ ID NO: 27.

In some embodiments, the present invention provides an antibody or an antigen-binding fragment thereof specifically binding to a T cell immunoreceptor with immunoglobulin and immunoreceptor tyrosine-based inhibitory motif domains (TIGIT), comprising a VH CDR1 set forth in SEQ ID NO: 21, a VH CDR2 set forth in SEQ ID NO: 22, a VH CDR3 set forth in SEQ ID NO: 23, a VL CDR1 set forth in SEQ ID NO: 25, a VL CDR2 set forth in SEQ ID NO: 26, and a VL CDR3 set forth in SEQ ID NO: 27.

In some embodiments, the present invention provides an antibody or an antigen-binding fragment thereof specifically binding to a T cell immunoreceptor with immunoglobulin and immunoreceptor tyrosine-based inhibitory motif domains (TIGIT), comprising a VH CDR1 set forth in SEQ ID NO: 21, a VH CDR2 set forth in SEQ ID NO: 22, a VH CDR3 set forth in SEQ ID NO: 23, a VL CDR1 set forth in SEQ ID NO: 25, a VL CDR2 set forth in SEQ ID NO: 43, and a VL CDR3 set forth in SEQ ID NO: 27.

In some embodiments, the antibody or the fragment thereof further comprises a heavy chain constant region, a light chain constant region, an Fc region, or a combination thereof. In some embodiments, the light chain is of kappa (κ) or lambda (λ) type. In some embodiments, the light chain constant region is a κ or λ chain constant region. In some embodiments, the light chain constant region is a κ chain constant region. In some embodiments, the light chain variable region is a κ or λ chain variable region. In some embodiments, the light chain variable region is a κ chain variable region. In some embodiments, the antibody or the fragment thereof is of one of the isotypes IgG, IgM, IgA, IgE or IgD. In some embodiments, the isotype is IgG1, IgG2, IgG3 or IgG4. In some embodiments, the antibody or the fragment thereof is a chimeric antibody, a humanized antibody, or a fully human antibody. In some embodiments, the antibody or the fragment thereof is a humanized antibody.

In some embodiments, the antibody or the fragment thereof further comprises a heavy chain constant region, a light chain constant region, an Fc region, or a combination thereof. In some embodiments, the Fc region is a human Fc region. In some embodiments, a heavy chain of the human Fc region comprises an amino acid E at position 356 (EU numbering system). In some embodiments, the heavy chain of the human Fc region comprises an amino acid M at position 386 (EU numbering system). In some embodiments, the heavy chain comprises an amino acid sequence set forth in SEQ ID NO: 28 or 29. In some embodiments, the light chain comprises an amino acid sequence set forth in SEQ ID NO: 30.

In some embodiments, the antibody or the fragment thereof comprises a heavy chain variable region comprising an amino acid sequence selected from the group consisting of SEQ ID NOs: 20. 33, 35, 37, 39 and 41, or a peptide chain having at least 90% sequence homology to an amino acid sequence selected from the group consisting of SEQ ID NOs: 20. 33, 35, 37, 39 and 41. In some embodiments, the antibody or the fragment thereof comprises a light chain variable region comprising an amino acid sequence selected from the group consisting of SEQ ID NOs: 24. 34, 36, 38, 40 and 42, or a peptide chain having at least 90% sequence homology to an amino acid sequence selected from the group consisting of SEQ ID NOs: 24. 34, 36, 38, 40 and 42.

In some embodiments, the antibody or the fragment thereof comprises a heavy chain variable region having an amino acid sequence set forth in SEQ ID NO: 35 and a light chain variable region having an amino acid sequence set forth in SEQ ID NO: 36.

In some embodiments, the antibody or the fragment thereof can effectively block the binding of TIGIT to PVR. In some embodiments, the antibody or the fragment thereof can activate lymphocytes to release cytokines.

In some embodiments, the antibody or the fragment thereof has an affinity value $K_D \leq 100$ pM for human TIGIT. In some embodiments, the antibody or the fragment thereof has an affinity value $K_D \leq 5$ nM for human TIGIT.

In some embodiments, the antibody or the fragment thereof has ADCC activity. In some embodiments, the antibody or the fragment thereof binds to fucose. In some embodiments, the antibody or the fragment thereof does not bind to fucose.

In another aspect, the present invention further describes a bispecific antibody comprising the antibody fragment disclosed herein and a second antigen-binding fragment specific for a molecule on an immune cell. The molecule includes PD-1, CTLA-4, LAG-3, CD28, CD122, 4-1BB, TIM3, OX-40, OX40L, CD40, CD40L, LIGHT, ICOS, ICOSL, GITR, GITRL, CD27, VISTA, B7H3, B7H4, HEVM, BTLA, KIR and CD47.

In another aspect, the present invention further provides a composition comprising the antibody or the fragment thereof disclosed herein, wherein the composition further comprises a pharmaceutically acceptable carrier. In some embodiments, no more than 50% of the antibody or the fragment thereof in the composition binds to fucose. In some embodiments, no more than 30% of the antibody or the fragment thereof in the composition binds to fucose. In some embodiments, no more than 20% of the antibody or the fragment thereof in the composition binds to fucose. In some embodiments, no more than 10% of the antibody or the fragment thereof in the composition binds to fucose. In some embodiments, no more than 5% of the antibody or the fragment thereof in the composition binds to fucose. In some embodiments, no more than 1% of the antibody or the fragment thereof in the composition binds to fucose.

In another aspect, the present invention further provides a polynucleotide encoding the antibody or the fragment thereof. In some embodiments, a sequence of the polynucleotide encoding the heavy chain of the antibody is set forth in SEQ ID NO 46; in some embodiments, a sequence of the polynucleotide encoding the light chain of the antibody is set forth in SEQ ID NO 47.

In another aspect, the present invention further provides a cell comprising one or more polynucleotides encoding the antibody or the fragment thereof disclosed herein.

In another aspect, the present invention further provides a method for preparing the antibody or the fragment thereof disclosed herein, comprising: culturing a cell comprising a polynucleotide encoding the antibody or the fragment thereof to express the antibody or the fragment thereof. In some embodiments, the cell is a CHO cell, a HEK293 cell, a Cost cell, a Cos7 cell, a CV1 cell or a murine L cell.

In another aspect, the present invention further provides therapeutic methods and use. In some embodiments, the present invention provides a method for treating a cancer or an infection in a patient in need, comprising administering to the patient an effective dose of the antibody or the fragment thereof disclosed herein. In some embodiments, the cancer is a solid tumor. In some embodiments, the cancer is bladder cancer, liver cancer, colon cancer, rectal cancer, endometrial cancer, leukemia, lymphoma, pancreatic cancer, small cell lung cancer, non-small cell lung cancer, breast cancer, urethral carcinoma, head and neck cancer, gastrointestinal cancer, gastric cancer, esophageal cancer, ovarian cancer, renal cancer, melanoma, prostate cancer and thyroid cancer. In some embodiments, the cancer may be bladder cancer, liver cancer, pancreatic cancer, non-small cell lung cancer, breast cancer, urethral carcinoma, colorectal cancer, head and neck cancer, squamous cell carcinoma, Merkel cell carcinoma, gastrointestinal cancer, gastric cancer, esophageal cancer, ovarian cancer, renal cancer, and small cell lung cancer. In some embodiments, the method further comprises administering to the patient a second cancer therapeutic agent. In some embodiments, the infection is a viral infection, a bacterial infection, a fungal infection, or a parasitic infection.

In some embodiments, the present invention provides a method for treating a cancer or an infection in a patient in need, comprising: (a) treating a cell with the antibody or the fragment thereof disclosed herein in vitro; and (b) administering the treated cell to the patient. In some embodiments, the method further comprises isolating the cell from an individual prior to step (a). In some embodiments, the cell is isolated from the patient. In some embodiments, the cell is isolated from a donor individual distinct from the patient. In some embodiments, the cell is a T cell, non-limiting examples of which include a tumor infiltrating T lymphocyte, a CD4+ T cell, a CD8+ T cell, or a combination thereof.

In some embodiments, the present invention further provides use of an anti-TIGIT antibody or a fragment thereof in preparing a medicament for treating a cancer or an infection in a patient in need. In some embodiments, the cancer is a solid tumor. In some embodiments, the cancer is selected from bladder cancer, liver cancer, colon cancer, rectal cancer, endometrial cancer, leukemia, lymphoma, pancreatic cancer, small cell lung cancer, non-small cell lung cancer, breast cancer, urethral carcinoma, head and neck cancer, gastrointestinal cancer, gastric cancer, esophageal cancer, ovarian cancer, renal cancer, melanoma, prostate cancer and thyroid cancer. In some embodiments, the use further comprises administering to the patient a second cancer therapeutic agent. In some embodiments, the infection is a viral infection, a bacterial infection, a fungal infection, or a parasitic infection.

In some embodiments, the present invention further provides use of a cell in preparing a medicament for treating a cancer or an infection, comprising: (a) treating the cell with an antibody or a fragment thereof in vitro, and (b) administering the treated cell to a patient. In some embodiments, the method further comprises isolating the cell from an individual prior to step (a). In some embodiments, the cell is isolated from the patient. In some embodiments, the cell is isolated from a donor individual different from the patient. In some embodiments, the cell is a T cell. In some embodiments, the T cell is a tumor infiltrating T lymphocyte, a CD4+ T cell, a CD8+ T cell, or a combination thereof.

In another aspect, the present invention further provides diagnostic methods and use. In some embodiments, the present invention provides a method for detecting TIGIT expression in a sample, comprising contacting the sample with an antibody or a fragment thereof in a certain condition such that the antibody or the fragment thereof binds to TIGIT, and detecting the binding, i.e., expression of TIGIT in the sample. In some embodiments, the sample includes a tumor cell, a tumor tissue, an infected tissue, or a blood sample.

BRIEF DESCRIPTION OF THE DRAWINGS

In order to more clearly illustrate the technical schemes in the embodiments of the present application, the drawings required for the embodiments are briefly described below. It is obvious that the drawings in the following description are only some embodiments described in the present application, wherein.

DETAILED DESCRIPTION

Definitions

Figure 1:
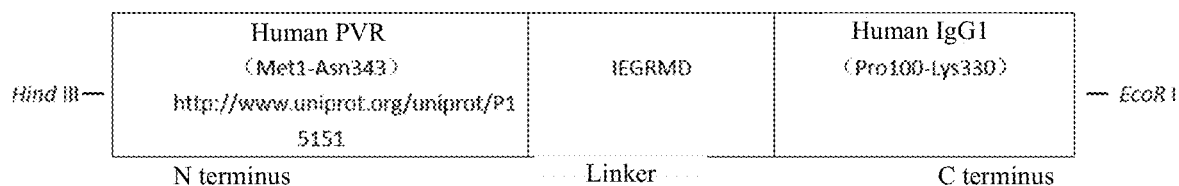
FIG. 1: A schematic diagram of the construction of PVR-FC fusion protein.

It should be noted that the term "an" entity refers to one or more of the entities. For example, "an antibody" should be interpreted as one or more antibodies. As such, the terms "a" (or "an"), "one or more" and "at least one" can be used interchangeably herein.

"Amino acid" refers to an organic compound containing both an amino group and a carboxyl group, such as an alpha-amino acid that can be encoded by a nucleic acid, either directly or in the form of a precursor. A single amino acid is encoded by a nucleic acid consisting of three nucleotides (also referred to as codon or base triplet). Each amino acid is encoded by at least one codon. An amino acid may be encoded by different codons, which is known as "codon degeneracy". Amino acids include natural amino acids and non-natural amino acids. Natural amino acids include alanine (three-letter symbol: Ala, one-letter symbol: A), arginine (Arg, R), asparagine (Asn, N), aspartic acid (Asp, D), cysteine (Cys, C), glutamine (Gln, Q), glutamic acid (Glu, E), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V).

"Conservative amino acid substitution" refers to the replacement of one amino acid residue with another amino acid residue having a side chain (R group) of similar chemical nature (e.g., charge or hydrophobicity). Generally, conservative amino acid substitutions do not substantially alter the functional properties of the protein. Examples of amino acid classes with a side chain of similar chemical nature include: 1) an aliphatic side chain: glycine, alanine, valine, leucine and isoleucine; 2) an aliphatic hydroxyl side chain: serine and threonine; 3) an amide-containing side chain: asparagine and glutamine; 4) an aromatic side chain: phenylalanine, tyrosine and tryptophan; 5) a basic side chain: lysine, arginine and histidine; and 6) an acidic side chain: aspartic acid and glutamic acid.

As used herein, the term "polypeptide" is intended to encompass both the singular form "polypeptide" and the plural form "polypeptides", and refers to a molecule consisting of monomers (amino acids) linearly linked by amide bonds (or peptide bonds). The term "polypeptide" refers to any single chain or multiple chains consisting of two or more amino acids and does not refer to a particular length of the product. Thus, included within the definition of "polypeptide" are peptides, dipeptides, tripeptides, oligopeptides, "proteins", "amino acid chains", or any other term used to refer to chains of two or more amino acids, and the term "polypeptide" may be used in place of, or interchangeably with, any of the above terms. The term "polypeptide" is also intended to refer to a product of post-expression polypeptide modification, including but not limited to glycosylation, acetylation, phosphorylation, amidation, derivatization by known protecting/blocking groups, proteolytic cleavage or non-naturally occurring amino acid modification. The polypeptide may be derived from a natural biological source or produced by recombinant techniques, but it is not necessarily translated from a specified nucleic acid sequence. It may be produced in any manner including chemical synthesis.

The term "isolated" as used herein with respect to antibodies, cells, nucleic acids, e.g., "isolated" DNA or RNA, refers to molecules that are separated from other DNA or RNA, respectively, that are present in the natural source of the macromolecule. The term "isolated" as used herein also refers to nucleic acids or peptides that are substantially free of cellular materials, viral materials or cell culture media when produced by recombinant DNA techniques, or of chemical precursors or other chemicals when chemically synthesized. In addition, "isolated nucleic acid" is intended to include nucleic acid fragments that do not and will not occur in nature. The term "isolated" is also used herein to refer to cells or polypeptides that are separated from other cellular proteins or tissues. Isolated polypeptides are intended to include both purified and recombinant polypeptides.

As used herein, the term "recombinant", with regard to a polypeptide or polynucleotide, is intended to refer to a polypeptide or polynucleotide that does not occur in nature, and non-limiting examples can be combined to produce a polynucleotide or polypeptide that does not normally occur.

"Homology" or "identity" or "similarity" refers to sequence similarity between two peptides or between two nucleic acid molecules. Homology can be determined by comparing the positions that can be aligned in the sequences. When a position of the compared sequences is occupied by the same base or amino acid, then the molecules are homologous at that position. The degree of homology between the sequences is a function of the number of matching or homologous positions shared by the sequences. The term "unrelated" or "non-homologous" refers to sequences having less than 40% identity, such as less than 25% identity to one of the sequences disclosed herein.

A polynucleotide or polynucleotide region (or a polypeptide or polypeptide region) having a certain percentage (e.g., 60%, 65%, 70%, 75%, 80%, 85%, 90%, 95%, 98%, or 99%) "sequence identity" to another sequence means that the percentage of bases (or amino acids) are identical between the two sequences compared when the sequences are aligned. This alignment and the percentage homology or sequence identity can be determined using software programs known in the art, such as the software programs described in Ausubel et al. eds., (2007), Current Protocols in Molecular Biology. Preferably, the alignment is performed using default parameters. One alignment program is BLAST using default parameters. Specifically, the programs are BLASTN and BLASTP, both using the following default parameters: Genetic code=standard; filter=none; strand=both; cutoff=60; expect=10; Matrix=BLOSUM62; Descriptions=50 sequences; sort by=HIGH SCORE; Databases=non-redundant; GenBank+EMBL+DDBJ+PDB+GenBank CDS translations+SwissProtein+SPupdate+PIR. Biologically equivalent polynucleotides are polynucleotides having the above specified percentage homology and encoding polypeptides having identical or similar biological activity.

The term "equivalent nucleic acid or polynucleotide" refers to a nucleic acid having a nucleotide sequence with a certain degree of homology or sequence identity to the nucleotide sequence of the nucleic acid or a complement thereof. A homologue of a double-stranded nucleic acid is intended to include a nucleic acid having a nucleotide sequence with a certain homology to the double-stranded nucleic acid or a complementary sequence thereof. In one aspect, a homologue of a nucleic acid is capable of hybridizing to a nucleic acid or a complement thereof. Likewise, an "equivalent polypeptide" refers to a polypeptide having a certain homology or sequence identity to the amino acid sequence of a reference polypeptide. In certain aspects, the sequence identity is at least about 70%, 75%, 80%, 85%, 90%, 95%, 98%, or 99%. In certain aspects, the equivalent polypeptide or polynucleotide has 1, 2, 3, 4 or 5 additions, deletions, substitutions, and combinations thereof, as compared to the reference polypeptide or polynucleotide. In certain aspects, an equivalent sequence retains the activity (e.g., epitope binding) or structure (e.g., salt bridge) of the reference sequence.

Hybridization reactions can be performed in conditions of different "stringencies". Hybridization reactions of a low stringency are typically performed in about 10×SSC or a solution of similar ionic strength/temperature at about 40° C. Hybridization reactions of a moderate stringency are typically performed in about 6×SSC at about 50° C. Hybridization reactions of a high stringency are typically performed in about 1×SSC at about 60° C. The hybridization reaction can also be performed in "physiological conditions" well known to those skilled in the art. Non-limiting examples of physiological conditions are temperature, ionic strength, pH and $Mg^{2+}$ concentration which are typically present in a cell.

A polynucleotide consists of a specific sequence of four nucleotide bases: adenine (A), cytosine (C), guanine (G), thymine (T)/uracil (U, instead of thymine when the polynucleotide is RNA). Thus, the term "polynucleotide sequence" is a letter representation of a polynucleotide molecule. The letter representation can be input into a database in a computer with a central processing unit and used for bioinformatics applications, such as for functional genomics and homology searches. The term "polymorphism" refers to the coexistence of more than one form of a gene or a portion thereof. The portion of the gene having at least two different forms (i.e., two different nucleotide sequences) is referred to as a "polymorphic region of the gene". The polymorphic region may be a single nucleotide, which has different identities in different alleles.

The terms "polynucleotide" and "oligonucleotide" are used interchangeably to refer to a polymeric form of nucleotides of any length, whether deoxyribonucleotides or ribonucleotides or analogs thereof. The polynucleotide may have any three-dimensional structure and may perform any function, known or unknown. The following are non-limiting examples of polynucleotides: genes or gene fragments (such as probes, primers, EST or SAGE tags), exons, introns, messenger RNA (mRNA), transport RNA, ribosomal RNA, ribozymes, cDNA, dsRNA, siRNA, miRNA, recombinant polynucleotides, branched polynucleotides, plasmids, vectors, isolated DNA of any sequence, isolated RNA of any sequence, nucleic acid probes and primers. Polynucleotides can include modified nucleotides, such as methylated nucleotides and nucleotide analogs. If present, structural modifications to the nucleotide can be made before or after the assembly of the polynucleotide. The sequence of nucleotides can be interrupted by non-nucleotide components. The polynucleotide may be further modified after polymerization, such as by conjugation with a labeling component. This term also refers to double-stranded and single-stranded molecules. Unless otherwise stated or required, embodiments of any polynucleotide disclosed herein include a double-stranded form and each of the two complementary single-stranded forms known or predicted to constitute the double-stranded form.

The term "encoding" as applied to a polynucleotide refers to a polynucleotide known to "encode" a polypeptide. When in its native state or manipulated by methods well known to those skilled in the art, the polynucleotide can be transcribed and/or translated to produce the polypeptide and/or mRNA for fragments thereof. An antisense strand is a complement sequence of such a nucleic acid. The coding sequence of the antisense strand can be deduced from the nucleic acid.

As used herein, "antibody" or "antigen-binding polypeptide" refers to a polypeptide or polypeptide complex that specifically recognizes and binds to an antigen. The antibody may be an intact antibody and any antigen-binding fragment or single chain thereof. The term "antibody" thus includes any protein or peptide comprising at least a portion of an immunoglobulin molecule that has biological activity for binding to an antigen. Examples include, but are not limited to, complementarity determining regions (CDRs) of a heavy or light chain or a ligand binding portion thereof, heavy chain variable regions (VHs) or light chain variable regions (VLs), heavy chain constant regions (CHs) or light chain constant regions (CLs), framework regions (FRs) or any portion thereof, or at least a portion of a binding protein. The CDRs include light chain CDRs (LCDRs) and heavy chain CDRs (HCDRs).

As used herein, the term "antibody fragment" or "antigen-binding fragment" is a part of an antibody, such as $F(ab')_2$, $F(ab)_2$, Fab', Fab, Fv, scFv, etc. Regardless of its structure, the antibody fragment binds to the same antigen recognized by an intact antibody. The term "antibody fragment" includes aptamers, mirror isomers, and bivalent antibodies. The term "antibody fragment" also includes any synthetic or genetically engineered protein that functions as an antibody by binding to a specific antigen to form a complex.

"Single chain variable fragment" or "scFv" refers to a fusion protein of a heavy chain variable region (VH) and a light chain variable region (VL) of an immunoglobulin. In some aspects, the regions are linked by a short linker peptide of 10 to about 25 amino acids. The linker may be enriched with glycine to improve flexibility, and enriched with serine or threonine to improve solubility, and may link the N terminus of VH and the C terminus of VL, or vice versa. Although the protein has the constant region removed and the linker introduced, it retains the specificity of the original immunoglobulin. ScFv molecules known in the art are described in, for example, U.S. Pat. No. 5,892,019.

The term "antibody" includes a wide variety of polypeptides that can be biochemically distinguished. Those skilled in the art will appreciate that the classes of heavy chains include gamma, mu, alpha, delta, or epsilon ($\gamma$, $\mu$, $\alpha$, $\delta$, or $\epsilon$), and some subclasses (e.g., $\gamma 1$-$\gamma 4$). The nature of this chain determines the "type" of the antibody as IgG, IgM, IgA, IgD or IgE. Immunoglobulin subclasses (isotypes), such as IgG1, IgG2, IgG3, IgG4, etc., have been well characterized and the functional specificity imparted is also known. Each modified form of these classes and isotypes will readily conceivable for those of ordinary skills in the art and therefore fall within the scope of the present disclosure, and all immunoglobulin classes are clearly within the scope of the present disclosure. With respect to IgG, a standard immunoglobulin molecule comprises two identical light chain polypeptides having a molecular weight of about 23,000 Daltons and two identical heavy chain polypeptides having a molecular weight of about 53,000-70,000 Daltons. Generally, these four chains are connected in a "Y" configuration through disulfide bonds, wherein the light chains start at the opening of "Y" configuration and extend through the variable region to surround the heavy chains.

Antibodies, antigen-binding fragments, or derivatives disclosed herein include, but are not limited to, polyclonal, monoclonal, multispecific, fully human, humanized, primatized or chimeric antibodies, single chain antibodies, epitope-binding fragments such as Fab, Fab' and $F(ab')_2$, Fd, Fv, single chain Fv (scFv), single chain antibody, disulfide-linked Fv (sdFv), fragments comprising VK or VH domains, fragments produced from Fab expression libraries, and anti-idiotype (anti-Id) antibodies (including, for example, anti-Id antibodies of the LIGHT antibody disclosed herein). The immunoglobulin or antibody molecules disclosed herein can be of any type (e.g., IgG, IgE, IgM, IgD, IgA and IgY) or class (e.g., IgG1, IgG2, IgG3, IgG4, IgA1 and IgA2) or subclass of immunoglobulin.

Light chains can be classified into kappa or lambda ($\kappa$ or $\lambda$). Each heavy chain may be connected with a $\kappa$ or $\lambda$ light chain. In general, when an immunoglobulin is produced by a hybridoma, a B cell or a genetically engineered host cell, the light and heavy chains are connected by covalent bonds, and the "tail" portions of the two heavy chains are connected by covalent disulfide bonds or non-covalent bonds. In the heavy chains, the amino acid sequence extends from the N terminus at the forked end of the Y configuration to the C terminus at the bottom of each chain. The immunoglobulin $\kappa$ light chain variable region is V$\kappa$; the immunoglobulin $\lambda$ light chain variable region is V$\lambda$.

Both the light and heavy chains are divided into structurally and functionally homologous regions. The terms "constant" and "variable" are used in accordance with function. In this regard, it should be understood that the light chain variable region (VL) and heavy chain variable region (VH) determine the antigen recognition and specificity. In contrast, the light chain constant region (CL) and heavy chain constant regions (CH1, CH2 or CH3) impart important biological properties such as secretion, transplacental movement, Fc receptor binding, and complement binding. By convention, the numbering of amino acids in the constant regions increases as they become further away from the antigen-binding site of the antibody or amino terminus. The N-terminal portion is the variable region, and the C-terminal portion is the constant region; the CH3 and CL domains comprise the carboxyl termini of the heavy chain and light chain, respectively.

As described above, the variable regions enable the antibody to selectively recognize and specifically bind to an epitope on the antigen. That is, the VL domain and VH domain of an antibody, or a subset of complementarity determining regions (CDRs), combine to form a variable region defining a three-dimensional antigen-binding site. The antibody quaternary structure forms the antigen-binding site present at the end of each arm of the Y configuration. More specifically, the antigen-binding site is defined by three CDRs in each of the VH and VL domains (i.e., HCDR1, HCDR2, HCDR3, LCDR1, LCDR2 and LCDR3). In certain cases, such as certain camelid-derived immunoglobulin molecules or camelid immunoglobulin-based engineered immunoglobulin molecules, an intact immunoglobulin molecule may consist of only heavy chains, without light chains. See, e.g., Hamers-Casterman et al., Nature 363:446-448 (1993).

In naturally occurring antibodies, the six "complementarity determining regions" or "CDRs" present in each antigen-binding domain are short, non-contiguous amino acid sequences that are specifically positioned to form the antigen-binding domain, assuming that the antibody is present in its three-dimensional configuration in an aqueous environment. The remaining amino acids in the antigen-binding domain, referred to as the "framework" region, exhibit little intermolecular variability. Most of the framework regions adopt a β-sheet conformation, with the CDRs forming a loop structure connected to, or in some cases forming part of, the β-sheet structure. Thus, the framework regions position the CDRs in a correct orientation by interchain non-covalent interactions through forming a scaffold. The antigen-binding domain formed by the specifically positioned CDRs defines a surface complementary to an epitope on the immunoreactive antigen that facilitates the non-covalent binding of the antibody to its cognate epitope. For any given heavy or light chain variable region, amino acids comprising the CDRs and the framework regions may be identified by one of ordinary skills in the art according to common definitions (see, e.g., Sequences of Proteins of Immunological Interest, Kabat, E., et al., U.S. Department of Health and Human Services, (1983) and Chothia and Lesk, J. Mol. Biol., 196:901-917 (1987)).

CDRs defined according to Kabat and Chothia systems include overlaps or subsets of amino acid residues when compared to each other. Nevertheless, it is within the scope of the terms defined and used herein to apply either definition to refer to the CDRs of an antibody or an antigen-binding fragment thereof. The exact number of residues comprising a specific CDR will vary according to the sequence and size of the CDR. One skilled in the art can conventionally determine which residues comprise the specific CDR based on the variable region amino acid sequence of the antibody.

Kabat et al. also defines a numbering system applicable to the variable region sequence of any antibody. One of ordinary skills in the art could undoubtedly apply the "Kabat numbering" system to any variable region sequence without depending on any experimental data beyond the sequence itself. As used herein, "Kabat numbering" refers to the numbering system proposed by Kabat et al., U.S. Dept. of Health and Human Services in Sequence of Proteins of Immunological Interest (1983).

The Kabat numbering system describes the CDRs as follows: HCDR1 begins around the $31^{st}$ amino acid (i.e., about 9 residues after the first cysteine residue), comprises about 5-7 amino acids, and ends at the next tryptophan residue. HCDR2 begins at the $15^{th}$ residue after the end of HCDR1, comprises about 16-19 amino acid residues, and ends at the next arginine or lysine residue. HCDR3 begins around the $33^{rd}$ amino acid residue after the end of HCDR2, comprises 3-25 amino acids, and ends with a sequence W-G-X-G, wherein X refers to any amino acid. LCDR1 begins around the $24^{th}$ residue (i.e., after a cysteine residue), comprises about 10-17 residues, and ends at the next tryptophan residue. LCDR2 begins around the $16^{th}$ residue after the end of LCDR1, and comprises about 7 residues. LCDR3 begins around the $33^{rd}$ residue after the end of LCDR2 (i.e., after a cysteine residue), comprises about 7-11 residues, and ends with a sequence F or W-G-X-G, where X refers to any amino acid.

The antibodies disclosed herein may be derived from any animal, including birds and mammals. Preferably, the antibody is derived from a human, a mouse, a donkey, a rabbit, a goat, a guinea pig, a camel, a llama, a horse, or a chicken source. In another embodiment, the variable region may be derived from a condricthoid source (e.g., from a shark).

A "light chain-heavy chain pair" refers to a collection of light and heavy chains that can form dimers through disulfide bonds between the CL domain of the light chain and the CH1 domain of the heavy chain.

As described above, the structures and three-dimensional configurations of the subunits in the constant regions of various immunoglobulin classes are well known. As used herein, the term "VH domain" includes the variable domain at the amino terminus of an immunoglobulin heavy chain and the term "CH1 domain" includes the first constant region (mostly at the amino terminus) of an immunoglobulin heavy chain. The CH1 domain is adjacent to the VH domain, and the CH1 domain is linked to the amino terminus of the hinge region of the immunoglobulin heavy chain molecule.

As used herein, the term "CH2 domain" includes that portion of the heavy chain molecule which extends from around the $244^{th}$ residue to the $360^{th}$ residue of the antibody using conventional numbering schemes ($244^{th}$-$360^{th}$ residues, Kabat numbering system; $231^{st}$-$340^{th}$ residues, EU numbering system; see Kabat et al., U.S. Dept. of Health and Human Services, Sequence of Proteins of Immunological Interest (1983)). The CH2 domain is unique in that it is not closely paired with other domains, but rather two N-linked branched carbohydrate chains are inserted between the two CH2 domains of an intact native IgG molecule. It is also documented that the CH3 domain extends from the CH2 domain to the C terminus of the IgG molecule, and comprises about 108 residues.

As used herein, the term "hinge region" includes a portion of the heavy chain connecting the CH1 domain and the CH2 domain. The hinge region comprises about 25 residues and is flexible, thereby enabling independent movement of the two N-terminal antigen-binding regions. The hinge region can be subdivided into three distinct domains: upper, middle and lower hinge domains (Roux et al., J. Immunol., 161: 4083 (1998)).

As used herein, the term "disulfide bond" includes a covalent bond formed between two sulfur atoms. Cysteine contains a thiol group which can form a disulfide bond or bridge with a second thiol group. In most naturally occurring IgG molecules, the CH1 and CL regions are connected by disulfide bonds, and the two heavy chains are connected by two disulfide bonds at corresponding positions 239 and 242 in the Kabat numbering system (or positions 226 and 229 in the EU numbering system).

As used herein, the term "chimeric antibody" is intended to refer to any antibody of which the immunoreactive region or site is obtained or derived from a first species, and the constant region (which may be intact, partial or modified in the present invention) is derived from a second species. In some embodiments, the target binding region or site is from a non-human source (e.g., mouse or primate) and the constant region is of a human source.

"Specifically bind to" generally refers to that an antibody binds to an epitope of an antigen via its antigen-binding domain, and that the binding requires complementarity between the antigen-binding domain and the epitope. By this definition, an antibody is said to "specifically bind to" an epitope when it binds to the epitope more readily through its antigen-binding domain than it binds to a random, irrelevant epitope. The term "specificity" is used herein to define the relative affinity of a specific antibody for binding to a specific epitope.

As used herein, the term "treatment" refers to both therapeutic treatment and prophylactic or preventative measures, the object of which is to prevent or slow (reduce) an undesirable physiological change or disorder, such as the progression of cancer. Beneficial or desired clinical results include, but are not limited to, relieved or eliminated symptoms, diminished extent of disease, stabilized (i.e., not worsening) state of disease, delayed or slowed disease progression, ameliorated or palliated state of disease, and alleviation or elimination (partial or total), whether detectable or undetectable. "Treatment" is also intended to refer to an extended survival compared to the survival expected for those not receiving the treatment. Those in need of the treatment include those with the condition or disorder, as well as those susceptible to the condition or disorder, or those in whom the condition or disorder is to be prevented.

"Subject" or "individual" or "animal" or "patient" or "mammal" generally refers to any subject, particularly a mammalian subject, in need of diagnosis, prognosis or treatment. Mammalian subjects include humans, dogs, cats, guinea pigs, rabbits, rats, mice, horses, bovines, etc.

As used herein, phrases such as "a patient in need of the treatment" or "a subject in need of the treatment" include subjects, e.g., mammalian subjects, that benefit from administration of the antibodies or compositions disclosed herein for detection, diagnostic process and/or treatment.

Anti-TIGIT Antibodies

The present invention provides anti-TIGIT antibodies having high affinity for human TIGIT protein. The test antibodies exhibit potent binding and inhibitory activity and are useful for therapeutic and diagnostic purposes. For example, as shown in the examples, these antibodies can effectively block the binding of TIGIT to PVR and can also effectively activate lymphocytes to release cytokines. These antibodies have high affinity for human TIGIT and suitable ADCC activity.

Accordingly, the present invention provides anti-TIGIT antibodies or fragments thereof that can specifically bind to TIGIT protein.

In some embodiments, the present invention provides an antibody comprising heavy and light chain variable domains having CDRs as shown in Table 2.1. As shown in the experiments in the examples, antibodies comprising these CDRs, whether murine or humanized, have activities for effectively binding and inhibiting TIGIT.

In some embodiments, the anti-TIGIT antibody disclosed herein comprises a VH set forth in SEQ ID NOs: 20, 33, 35, 37, 39 and/or 41 or a sequence having 80%, 85%, 90%, 95%, 98% or 99% sequence identity to the VH, and a VL set forth in SEQ ID NOs: 24, 34, 36, 38, 40 and/or 42 or a sequence having 80%, 85%, 90%, 95%, 98% or 99% sequence identity to the VL. In some embodiments, a VH having 80%, 85%, 90%, 95%, 98% or 99% overall sequence identity retains the CDRs (SEQ ID NOs: 21-23, 25-27 and 43, or an amino acid sequence with a substitution, deletion or insertion at a single site). In one embodiment, the VH has an amino acid sequence set forth in SEQ ID NO: 35, and the VL has an amino acid sequence set forth in SEQ ID NO: 36.

In some embodiments, the anti-TIGIT antibody disclosed herein comprises a human Fc region. The constant region sequences of the heavy and light chains may be, for example, SEQ ID NOs: 28 (or 29) and 30, respectively. Comparing to SEQ ID NO: 28, SEQ ID NO: 29 has a substitution of amino acid D by E at position 239 (position 356 according to EU numbering, or position 377 according to Kabat numbering), and a substitution of amino acid L by M at position 241 (position 358 according to EU numbering, or position 381 according to Kabat numbering).

In some embodiments, the anti-TIGIT antibody disclosed herein has a heavy chain with a sequence set forth in SEQ ID NO: 44 and a light chain with a sequence set forth in SEQ ID NO: 45.

It will also be appreciated by those of ordinary skills in the art that the antibody disclosed herein may be modified to have an amino acid sequence that differs from the amino acid sequence of the naturally occurring binding polypeptide from which the antibody is derived. For example, a polypeptide or an amino acid sequence derived from a given protein may be similar to the original sequence, for example, having a certain proportion of identity to the original sequence, e.g., 60%, 70%, 75%, 80%, 85%, 90%, 95%, 98% or 99% identity to the original sequence.

In some embodiments, the antibody comprises an amino acid sequence and one or more groups generally irrelevant to an antibody. Representative modifications are described in more detail below. For example, the antibody disclosed herein may comprise a flexible linker sequence, or may be modified to add a functional group (e.g., PEG, a drug, a toxin, or a tag).

In some embodiments, the antibody or the fragment thereof does not bind to fucose. In some embodiments, the antibody or the fragment thereof has up to three (or up to two or one) amino acid residues modified by fucose. In some embodiments, no more than 0.01%, 0.1%, 1%, 2%, 3%, 4% or 5% of protein molecules in a preparation comprising the antibody or the fragment thereof are modified by fucose. In some embodiments, an antibody with reduced or eliminated fucose modification has stronger ADCC effect and is suitable for certain therapeutic use.

The antibodies, the variants or the derivatives thereof disclosed herein include modified derivatives, i.e., modified by covalent attachment of any type of molecule to the antibody, wherein the covalent attachment does not prevent the antibody from binding to the epitope. Including, but not limited to, the following examples, antibodies can be modified by, for example, glycosylation, acetylation, pegylation, phosphorylation, amidation, derivatization by known protecting/blocking groups, proteolytic cleavage, attachment to cellular ligands or other proteins. Any of a number of chemical modifications may be made by techniques in the prior art, including but not limited to specific chemical cleavage, acetylation, formylation, metabolic synthesis of tunicamycin, and the like. In addition, the antibody may comprises one or more non-classical amino acids.

In some embodiments, the antibody may be conjugated with a therapeutic agent, a prodrug, a peptide, a protein, an enzyme, a virus, a lipid, a biological response modifier, an agent, or PEG.

The antibody may be conjugated or fused with a therapeutic agent, which may comprise a detectable label, such as a radiolabel, an immunomodulator, a hormone, an enzyme, an oligonucleotide and a photoactive therapeutic or diagnostic agent, a cytotoxic agent which may be a drug or a toxin, an ultrasound enhancing agent, a nonradioactive label, and compositions thereof, and other such agents known in the art.

The antibody may be detectably labeled by coupling to a chemiluminescent compound. The presence of the chemiluminescent-labeled antibody is then determined by detecting the luminescence that occurs during the course of chemical reactions. Examples of particularly useful chemiluminescent-labeled compounds include luminol, isoluminol, aromatic acridinium esters, imidazole, acridinium salts and oxalate esters.

Bifunctional Molecules

TIGIT is an immunoreceptor and a tumor antigen. As a tumor antigen targeting molecule, an antibody or an antigen-binding fragment that specifically binds to TIGIT can be combined with another antigen-binding fragment with immune cell specificity to produce a bispecific antibody.

In some embodiments, the immune cell is selected from the group consisting of a T cell, a B cell, a monocyte, a macrophage, a neutrophil, a dendritic cell, a phagocyte, a natural killer cell, an eosinophil, a basophil and a mast cell. Targeting molecules on immune cells include, for example, CD3, CD16, CD19, CD28 and CD64. Other examples include PD-1, CTLA-4, LAG-3 (also known as CD223), CD28, CD122, 4-1BB (also known as CD137), TIM3, OX-40 or OX40L, CD40 or CD40L, LIGHT, ICOS/ICOSL, GITR/GITRL, TIGIT, CD27, VISTA, B7H3, B7H4, HEVM or BTLA (also known as CD272), killer-cell immunoglobulin-like receptors (KIRs) and CD47. Specific examples of bispecificity include, but are not limited to, TIGIT/PD-1, TIGIT/LAG3, and TIGIT/CD47. As shown in the examples, the TIGIT antibodies disclosed herein have a synergistic effect with PD-L1 antibodies.

In some embodiments, the antibody or the antigen-binding fragment that specifically binds to TIGIT can also be combined with another antigen-binding fragment with tumor antigen specificity to produce a bispecific antibody. The "tumor antigen" is an antigenic substance produced by tumor cells, i.e., that induces an immune response in a host. The tumor antigen can be used for identifying tumor cells and can be used as a candidate target for treating cancers. Normal proteins in the body are not antigenic. Certain proteins are produced or overexpressed during tumorigenesis and are therefore "foreign" to the body. Such proteins may include normal proteins well-sequestered by the immune system, proteins that are usually produced in very small quantities, proteins that are usually produced only at certain stages of development, or proteins that are structurally modified due to mutations.

A large number of tumor antigens have been discovered in the art and new tumor antigens can be readily identified by screening. Non-limiting examples of tumor antigens include: EGFR, Her2, EpCAM, CD20, CD30, CD33, CD47, CD52, CD133, CD73, CEA, gpA33, mucin, TAG-72, CDC, PSMA, folate-binding protein, GD2, GD3, GM2, VEGF, VEGFR, integrin, αVβ3, α5β1, ERBB2, ERBB3, MET, IGF1R, EPHA3, TRAILR1, TRAILR2, RANKL, FAP and tenascin.

In certain aspects, a monovalent unit is specific for a protein overexpressed on a tumor cell compared to that on a corresponding non-tumor cell. As used herein, the "corresponding non-tumor cell" refers to a non-tumor cell that is of the same cell type as the origin of the tumor cell. It is noted that such proteins are not necessarily distinct from tumor antigens, and non-limiting examples include: carcinoembryonic antigen (CEA), which is overexpressed in most colon cancers, rectal cancers, breast cancers, lung cancers, pancreatic cancers and gastrointestinal cancers; neuregulin receptor (HER-2, neu or c-erbB-2), which is usually overexpressed in breast cancers, ovarian cancers, colon cancers, lung cancers, prostate cancers and cervical cancers; epidermal growth factor receptor (EGFR), which is highly expressed in a series of solid tumors including breast cancers, head and neck cancers, non-small cell lung cancers and prostate cancers; asialoglycoprotein receptor; transferrin receptor; serine protease inhibitor complex receptor, which is expressed on hepatocytes; fibroblast growth factor receptor (FGFR), which is overexpressed on pancreatic ductal adenocarcinoma cells; vascular endothelial growth factor receptor (VEGFR) for use in anti-angiogenic gene therapy; folate receptor, which is selectively overexpressed in 90% of non-adhesive ovarian cancers; cell surface glycocalyx; carbohydrate receptor; and polymeric immunoglobulin receptor, which mainly delivers genes to respiratory epithelial cells and is potentially attractive for treatment of, for example, cystic fibrosis. Non-limiting examples of bispecificity in this respect include: TIGIT/EGFR, TIGIT/Her2, TIGIT/CD33, TIGIT/CD133, TIGIT/CEA and TIGIT/VEGF.

The present invention also discloses different forms of bispecific antibodies. In some embodiments, the anti-TIGIT fragment and the another fragment are each selected from a Fab fragment, a single chain variable fragment (scFv) and a single domain antibody. In some embodiments, the bispecific antibody further comprises an Fc fragment.

The present invention further discloses bifunctional molecules other than antibodies or antigen-binding fragments. As a tumor antigen targeting molecule, the antibody or the antigen-binding fragment disclosed herein that specifically binds to TIGIT can be optionally linked to an immunocytokine or a ligand via a peptide linker. The linked immunocytokines or ligands include, but are not limited to: IL-2, IL-3, IL-4, IL-5, IL-6, IL-7, IL-10, IL-12, IL-13, IL 15, GM-CSF, TNF-α, CD40L, OX40L, CD27L, CD30L, 4-1BBL, LIGHT and GITRL. Such bifunctional molecules can combine the immune checkpoint blockade effects with local immune modulation at the tumor site.

Polynucleotides Encoding Antibodies and Methods for Preparing Antibodies

The present invention further discloses isolated polynucleotide or nucleic acid molecules encoding the antibodies and the antigen-binding fragments or derivatives thereof disclosed herein. The polynucleotides disclosed herein can encode the entire heavy chain variable region and light chain variable region of the above antibodies or the antigen-binding fragments or derivatives. In addition, the polynucleotides disclosed herein can encode a portion of the heavy chain variable region and light chain variable region of the above antibodies or the antigen-binding fragments or derivatives.

In some embodiments, the sequence of the polynucleotide encoding anti-TIGIT antibody h10D8OF is set forth in SEQ ID NOs: 46 and 47, wherein the sequence SEQ ID NO: 46 can encode the heavy chain of anti-TIGIT antibody h10D8OF and the sequence SEQ ID NO: 47 can encode the light chain of anti-TIGIT antibody h10D8OF.

The sequence of SEQ ID NO: 46 is as follows:

caggtgcagctggtggagtccggcggcggagtggtgcagcctggaaggtc cctgagactggactgtaaggccagcggcttcacctttagcagctacggca tgagctgggtgagacaggccctggcaagggcctggagctggtggctacc atcaatagcaatggcggcagcacctactaccccgacagcgtgaagggcag attcactatcagcagagacaactccaagaatacctgttcctgcagatga atagcctgagagccgaggacaccgccgtgtactactgcgccaggctgggc accggcaccctgggatttgcctactggggccagggtacctggttaccgt tagcagcgcgagcaccaaaggcccgagcgtgtttccgctggccccgagca gcaaaagcaccagcggtggcaccgcagcgctgggttgcctggtgaaagat tattccggaaccggtgacggtgtcgtggaactcaggcgccctgaccag cggcgtgcacaccttcccggctgtcctacagtcctcaggactctactccc tcagcagcgtggtgaccgtgccctccagcagcttgggcacccagacctac atctgcaacgtgaatcacaagcccagcaacaccaaggtggacaagaaagt tgagcccaaatcttgtgacaaaactcacacatgcccaccgtgcccagcac ctgaactcctgggggaccgtcagtcttcctcttcccccaaaacccaag gacaccctcatgatctcccggacccctgaggtcacatgcgtggtggtgga cgtgagccacgaagaccctgaggtcaagttcaactggtacgtggacggcg tggaggtgcataatgccaagacaaagccgcgggaggagcagtacaacagc acgtaccgtgtggtcagcgtcctcaccgtcctgcaccaggactggctgaa tggcaaggagtacaagtgcaaggtctccaacaaagccctcccagccccca tcgagaaaaccatctccaaagccaaagggcagccccgagaaccacaggtg tacaccctgcccccatcccgggatgagctgaccaagaaccaggtcagcct gacctgcctggtcaaaggcttctatcccagcgacatcgccgtggagtggg agagcaatgggcagccggagaacaactacaagaccacgcctcccgtgctg gactccgacggctccttcttcctctacagcaagctcaccgtggacaagag caggtggcagcagggggaacgtcttctcatgctccgtgatgcatgaggctc tgcacaaccactacacgcagaagagcctctccctgtctccgggtaaatga The sequence of SEQ ID NO: 47 is as follows:

gagatcgtgatgacccagagcccgccaccctgtccctgagcccaggaga gagagccaccctgagctgcaaggcctccaggacgtgaagaccgccgtga gctggtatcaacagaagcctggccaggccccagactgctgatctactgg gcctccaccagggccaccggcatccctgctagattcagcggctccggctc cggcaccgattacaccctgaccatcagcagcctggagcctgaggatttcg ccgtgtactactgtcagcagcactactccacccttggaccttcggccag ggcaccaaggtggagatcaagcgtacggtggctgcaccatctgtcttcat cttcccgccatctgatgagcagttgaaatctggaactgcctctgttgtgt gcctgctgaataacttctatcccagagaggccaaagtacagtggaaggtg gataacgccctccaatcgggtaactcccaggagagtgtcacagagcagga cagcaaggacagcacctacagcctcagcagcaccctgacgctgagcaaag cagactacgagaaacacaaagtctacgcctgcgaagtcacccatcagggc ctgagctcgcccgtcacaaagagcttcaacaggggagagtgttga In some embodiments, the anti-TIGIT antibody or the antigen-binding fragment thereof disclosed herein is prepared by using hybridoma techniques. For preparing monoclonal antibodies using, for example, hybridoma methods, see, e.g., those described by Kohler and Milstein, *Nature*, 256:495 (1975). In the hybridoma method, a mouse, a hamster or other appropriate host animal, is typically immunized with an immunizing agent to elicit production of lymphocytes or production of antibodies that can specifically bind to the immunizing agent.

The immunizing agent will generally include a protein antigen, a fragment thereof or a fusion protein thereof. Generally, if a human cell is desired, a peripheral blood lymphocyte is used; if a cell of non-human mammalian origin is desired, a spleen lymphocyte or lymph node cell is used. In some embodiments, a spleen lymphocyte is used. The lymphocyte is then fused with an immortalized cell line using a suitable fusing agent, such as polyethylene glycol, to form a hybridoma cell (Goding, *Monoclonal Antibodies: Principles and Practice*, Academic Press, (1986) pp. 59-103). The immortalized cell line is generally a transformed mammalian cell, particularly a myeloma cell of rodent, bovine or human origin. Generally, rat or mouse myeloma cell lines are used. In some embodiments, a spleen lymphocyte and a mouse myeloma cell are used for fusion. The hybridoma cell may be cultured in a suitable culture medium preferably containing one or more substances that inhibit the growth or survival of unfused immortalized cells. For example, if the parent cells lack hypoxanthine-guanine phosphoribosyltransferase (HGPRT or HPRT), the culture medium for the hybridoma generally contains hypoxanthine, aminopterin and thymine ("HAT medium"), which prevent the growth of HGPRT-deficient cells. In some embodiments, the binding specificity of the monoclonal antibody produced by the hybridoma cells is determined by immunoprecipitation or an in vitro binding assay, such as radioimmunoassay (RIA) or enzyme-linked immunosorbent assay (ELISA). Such techniques and assays are known in the art. The binding affinity of the monoclonal antibody can be determined, for example, by Scatchard analysis described by Munson and Pollard, *Anal. Biochem.*, 107:220 (1980). Furthermore, in the therapeutic application of the monoclonal antibody, it is important to identify antibodies with high specificity and high binding affinity for the target antigen.

After the desired hybridoma cells are identified, the clones can be subcloned using dilution cloning procedures and grown by standard methods. (see Goding, *Monoclonal Antibodies: Principles and Practice*, Academic Press, (1986) pp. 59-103). Suitable media for this purpose include, for example, Dulbecco's modified Eagle's Medium and RPMI-1640 medium.

In some embodiments, the monoclonal antibody secreted by the subclone can be isolated or purified by conventional techniques, such as protein A-sepharose, hydroxyapatite chromatography, gel electrophoresis, dialysis, or affinity chromatography.

The monoclonal antibody can also be prepared by recombinant DNA methods, such as those described in U.S. Pat. No. 4,816,567. DNA encoding the monoclonal antibody disclosed herein can be readily isolated and sequenced using conventional methods (e.g., by using oligonucleotide probes that can specifically bind to genes encoding the heavy and light chains of murine antibodies). The hybridoma cell described herein serves as a preferred source of such DNA. DNA encoding the antibody disclosed herein can also be synthesized by conventional methods based on antibody sequence design. The isolated or synthetic DNA is inserted into an expression vector, and then transfected into a host cell such as a Chinese hamster ovary (CHO) cell, a human embryonic kidney (HEK) 293 cell, a simian COS cell, a PER. NS0 cell, a SP2/0 cell, a YB2/0 cell or a myeloma cell that does not otherwise produce immunoglobulins, thereby obtaining a synthetic monoclonal antibody in the recombinant host cell.

In some embodiments, the anti-TIGIT antibody or the antigen-binding fragment thereof disclosed herein is prepared by hybridoma techniques. A fusion protein comprising a TIGIT extracellular region is used to immunize a mouse; spleen lymphocytes of the immunized mouse are fused with myeloma cells; the hybridoma cells are screened through the fusion protein comprising the TIGIT extracellular region; the positive hybridoma cells are subjected to dilution cloning and further subcloning; and the binding capacity of the hybridoma cell strains to the fusion protein comprising the TIGIT extracellular region is identified again for producing the anti-TIGIT antibody. In some embodiments, the fusion protein comprising the TIGIT extracellular region is TIGIT-Fc. In some embodiments, the mouse is a female Balb/c mouse aged 6-8 weeks.

Methods of making antibodies are well known in the art and are described herein. In some embodiments, the variable and constant regions of the antibody or the antigen-binding fragment thereof disclosed herein are both fully human. The fully human antibody can be prepared using techniques known in the art and disclosed herein. For example, a fully human antibody against a specific antigen can be prepared by administering the antigen to transgenic animals that have been modified to produce the antibody in response to antigen challenge, but whose endogenous loci have been disabled. Exemplary techniques that can be used to prepare such antibodies are found in U.S. Pat. Nos. 6,150,584, 6,458,592 and 6,420,140, which are incorporated herein by reference in their entireties.

In some embodiments, the produced antibody does not elicit a deleterious immune response in the animal, e.g., human, to be treated. In some embodiments, the antibody or the antigen-binding fragment or derivative thereof disclosed herein is modified using techniques well known in the art to reduce the immunogenicity. For example, the antibody can be humanized, primatized or deimmunized, or a chimeric antibody can be prepared. Such antibodies are derived from non-human antibodies, typically murine or primate antibodies, which retain or substantially retain the antigen-binding properties of the parent antibody but are less immunogenic in humans. This can be accomplished by a variety of methods, including: (a) grafting an entire variable region of a non-human origin to a constant region of a human origin to produce a chimeric antibody; (b) grafting at least a portion of one or more non-human complementarity determining regions (CDRs) to framework regions and a constant region of a human origin, with or without retention of critical framework residues; or (c) grafting an entire variable region of a non-human origin, but "hiding" the surface residues by replacing them with portions of a human-like origin.

Deimmunization may also be used to reduce the immunogenicity of the antibody. "Deimmunization" includes altering the antibody to modify the T cell epitopes (see, e.g., International Application Publication Nos. WO/9852976A1 and WO/0034317A2). For example, the sequences of the heavy and light chain variable regions from the original antibody are analyzed, and a "map" of human T cell epitopes from each V region is generated, showing the positions of the epitopes relative to the complementarity determining regions (CDRs) and other critical residues within the sequence. Individual T cell epitopes from the T cell epitope maps are analyzed to identify alternative amino acid substitutions with a lower risk of altering the final antibody activity. A series of alternative heavy and light chain variable region sequences comprising combinations of amino acid substitutions are designed and subsequently incorporated into a series of binding polypeptides. Typically, 12 to 24 variants of the antibody are generated and tested for the binding capacity and/or function. The genes of intact heavy and light chains comprising the modified variable regions and human constant regions are cloned into an expression vector, and the plasmid is then transferred into a cell line to produce an intact antibody. The antibodies are compared in appropriate biochemical and biological experiments to identify the best variant.

The binding specificity of the antibody or the antigen-binding fragment disclosed herein can be detected by an in vitro assay, such as co-immunoprecipitation, radioimmunoassay (RIA) or enzyme-linked immunosorbent assay (ELISA).

Examples of techniques that can be used to produce a single chain Fv (scFv) and an antibody include, for example, those described in U.S. Pat. Nos. 4,946,778 and 5,258,498, and Huston et al., *Methods in Enzymology,* 203:46-88 (1991), Shu et al., *Proc. Natl. Sci. USA,* 90:1995-1999 (1993) and Skerra et al., *Science,* 240:1038-1040 (1988), and other known methods.

For certain use, including in vivo use of antibodies in humans and in vitro detection assays, a chimeric antibody, a humanized antibody or a fully human antibody may be preferred. Chimeric antibodies are molecules in which different portions of the antibody are derived from different animal species, such as antibodies having variable regions of a murine monoclonal antibody and constant regions of a human immunoglobulin. Methods for producing chimeric antibodies are known in the art, see Morrison, *Science,* 229:1202 (1985), Oi et al., *BioTechniques,* 4:214 (1986), Gillies et al., *J. Immunol. Methods,* 125:191-202 (1989), and U.S. Pat. Nos. 5,807,715, 4,816,567 and 4,816,397, which are incorporated herein by reference in their entireties.

Humanized antibodies are antibody molecules derived from non-human antibodies capable of binding the antigen of interest, wherein the antibodies have one or more complementarity determining regions (CDRs) of a non-human origin in combination with framework regions from a human immunoglobulin molecule. Generally, certain framework residues in the human framework regions will be substituted by corresponding residues from the CDR donor antibody, preferably residues that may improve the antigen binding. Such framework substitutions can be identified by methods well known in the art, for example, by modeling the interaction of the CDR and framework residues to identify framework residues that play an important role in antigen binding and by sequence alignment to identify aberrant framework residues at particular positions. (see Queen et al., U.S. Pat. No. 5,585,089 and Riechmann et al., *Nature* 332:323 (1988), which are incorporated herein by reference in their entireties). Antibodies can be humanized by a variety of techniques well known in the art, such as CDR grafting (Pat. No. EP239,400, PCT Publication No. WO91/09967, and U.S. Pat. Nos. 5,225,539, 5,530,101 and 5,585,089), repair or surface rearrangement (Pat. Nos. EP592,106 and EP519,596, and Padlan, *Molecular Immunology* 28(4/5): 489-498 (1991), Studnicka et al., *Protein Engineering* 7(6): 805-814 (1994), and Roguska. et al., *Proc. Natl. Sci. USA* 91:969-973 (1994)), and chain rearrangement (U.S. Pat. No. 5,565,332), which are incorporated herein by reference in their entireties.

Fully human antibodies are particularly desirable for treating human patients. Fully human antibodies can be prepared by a variety of methods known in the art, including phage display methods using antibody libraries from human immunoglobulin sequences. Reference may also be made to U.S. Pat. Nos. 4,444,887 and 4,716,111, and PCT Publication Nos. WO98/46645, WO98/50433, WO98/24893, WO98/16654, WO96/34096, WO96/33735 and WO91/10741, each of which is incorporated herein by reference in its entirety.

Human antibodies can also be produced by transgenic mice that cannot express functional endogenous immunoglobulins but express human immunoglobulin genes. For example, human heavy and light chain immunoglobulin gene complexes can be introduced randomly or by homologous recombination into mouse embryonic stem cells. Alternatively, in addition to the human heavy and light chain genes, human variable, constant and diversity regions can be introduced into mouse embryonic stem cells. Mouse heavy and light chain immunoglobulin genes can be disabled by homologous recombination separately or simultaneously through introducing human immunoglobulin loci. In particular, homozygous deletion of the JH region can prevent the production of endogenous antibodies. The modified embryonic stem cells are expanded and microinjected into blastocysts to produce chimeric mice. The chimeric mice are then bred to produce homozygous progeny that express human antibodies. The transgenic mice are immunized by conventional methods with selected antigens, e.g., all or part of the desired polypeptide targets. Antigen-targeting monoclonal antibodies can be obtained from the immunized transgenic mice using conventional hybridoma techniques. The human immunoglobulin transgenes carried by the transgenic mice rearrange during B cell differentiation, resulting in class switch and somatic mutation. Accordingly, using this technique, IgG, IgA, IgM, and IgE antibodies that are useful for therapy can be produced. For a review related to this technique for producing fully human antibodies, see Lonberg and Huszar, *Int. Rev. Immunol.* 73:65-93 (1995). For a detailed discussion of this technique for producing fully human antibodies and human monoclonal antibodies and procedures for producing such antibodies, see PCT Publication Nos. WO98/24893, WO96/34096 and WO96/33735, and U.S. Pat. Nos. 5,413,923, 5,625,126, 5,633,425, 5,569,825, 5,661,016, 5,545,806, 5,814,318 and 5,939,598, which are incorporated herein by reference in their entireties. In addition, companies such as Abgenix (Freemont, Calif.) and GenPharm (San Jose, Calif.) can provide fully human antibodies against selected antigens using similar techniques to those described above.

Fully human antibodies recognizing selective epitopes can also be produced using a technique known as "guided selection". In this method, a selected non-human monoclonal antibody, such as a mouse antibody, is used to guide the screening of fully human antibodies that recognize the same epitope. (Jespers et al., *Bio/Technology* 72:899-903 (1988) and U.S. Pat. No. 5,565,332, which are incorporated herein by reference in their entireties).

In other embodiments, DNA encoding the desired monoclonal antibody can be readily isolated and sequenced using conventional methods (e.g., using oligonucleotide probes that can specifically bind to genes encoding the heavy and light chains of a murine antibody). Isolated and subcloned hybridoma cells are preferred sources of such DNA. Once isolated, the DNA can be inserted into an expression vector and then transfected into prokaryotic or eukaryotic host cells such as *E. coli* cells, simian COS cells, Chinese hamster ovary (CHO) cells, or myeloma cells that do not otherwise produce immunoglobulins. More specifically, the isolated DNA (which may be synthetic as described herein) can be used to clone sequences for preparing the constant and variable regions of an antibody, as described in Newman et al. and U.S. Pat. No. 5,658,570 published on Jan. 25, 1995, which are incorporated herein by reference in their entireties. Essentially, this requires extraction of RNA from the selected cells and conversion to cDNA, followed by amplification by PCR using Ig-specific primers. Suitable probes for this purpose are also described in U.S. Pat. No. 5,658,570. As will be discussed in more detail below, transformed cells expressing the desired antibodies can be cultured in relatively larger batches to satisfy the clinical and commercial needs of immunoglobulins.

In addition, using conventional recombinant DNA techniques, one or more CDRs of the antibody or the antigen-binding fragment disclosed herein can be inserted into framework regions, e.g., into human framework regions to construct a humanized non-fully human antibody. The framework regions may be naturally occurring or consensus framework regions, preferably human framework regions (see Chothia et al., *J. Mol. Biol.* 278:457-479 (1998), in which a range of human framework regions are listed). Preferably, polynucleotides produced by combination of framework regions and the CDRs encode antibodies that specifically bind to at least one epitope of the desired polypeptide (e.g., LIGHT). Preferably, one or more amino acid substitutions are made within the framework regions, preferably amino acid substitutions capable of improving the binding of the antibody to its antigen.

Additionally, substitution or deletion of one or more cysteine residues in the variable regions involved in interchain disulfide bond formation can be made in this manner, thereby producing an antibody molecule lacking one or more interchain disulfide bonds. Other alterations to the polynucleotides made within the technology scope of the art are also encompassed by the present invention.

Furthermore, the chimeric antibody technique (Morrison et al., *Proc. Natl. Acad. Sci. USA*:851-855 (1984), Neuberger et al., *Nature* 372:604-608 (1984) and Takeda et al., *Nature* 314:452-454 (1985)) by splicing genes of murine antibody molecules with appropriate antigen specificity and genes of human antibody molecules with appropriate biological activity can be used. In the present invention, chimeric antibodies are molecules in which different portions are derived from different animal species, such as chimeric antibodies having variable regions from a murine monoclonal antibody and constant regions of a human immunoglobulin.

In addition, another efficient method for producing recombinant antibodies, which in particular is capable of producing primate antibodies comprising monkey variable region and human constant region sequences, is disclosed in Newman, *Biotechnology* 10:1455-1460 (1992), which is incorporated herein by reference in its entirety. Furthermore, this technique is also described in commonly assigned U.S.

Pat. Nos. 5,658,570, 5,693,780 and 5,756,096, each of which is incorporated herein by reference in its entirety.

Antibodies can be prepared by using conventional recombinant DNA techniques. Vectors and cell lines for antibody production can be selected, constructed and cultured using techniques well known to those skilled in the art. These techniques are described in various laboratory manuals and main publications, such as Recombinant DNA Technology for Production of Protein Therapeutics in Cultured Mammalian Cells, D. L. Hacker, F. M. Wurm, *Reference Module in Life Sciences,* 2017, which is incorporated by reference in its entirety, including the supplements.

In some embodiments, the DNA encoding the antibody described herein can be synthesized according to antibody amino acid sequence design by conventional methods, inserted into an expression vector, and transfected into a host cell. The transfected host cell is then cultured in a medium to produce the monoclonal antibody. In some embodiments, the vector expressing the antibody comprises at least one promoter element, an antibody coding sequence, a transcription termination signal and a poly-A tail. Other elements include enhancers, Kozak sequences, and donor and recipient sites flanking the inserted sequence for RNA splicing. Efficient transcription can be obtained by early and late promoters of SV40, long terminal repeats from retroviruses such as RSV, HTLV1 and HIVI, and early promoters of cytomegalovirus, and promoters from other cells such as actin promoter can also be used. Suitable expression vectors may include pIRES1neo, pRetro-Off, pRetro-On, PLXSN, or Plncx, pcDNA3.1 (+/−), pcDNA/Zeo (+/−), pcDNA3.1/Hygro(+/−), PSVL, PMSG, pRSVcat, pSV2dhfr, pBC12MI, pCS2, etc. Commonly used mammalian host cells include 293 cells, Cos1 cells, Cos7 cells, CV1 cells, murine L cells, CHO cells, etc.

In some embodiments, the inserted gene fragment should comprise a screening label, common ones of which include screening genes such as dihydrofolate reductase, glutamine synthetase, neomycin resistance and hygromycin resistance, to facilitate the screening and separation of cells that have been successfully transfected. The constructed plasmid is transfected to a host cell without the above genes, and the successfully transfected cells are cultured in a large quantity in a selective culture medium to produce the desired target protein.

In addition, mutations can be introduced in the nucleotide sequence encoding the antibody disclosed herein using standard techniques known to those skilled in the art, including but not limited to site-directed mutations resulting in amino acid substitutions and PCR-mediated mutations. Preferably, the variant (including derivative) encodes a substitution of less than 50 amino acids, a substitution of less than 40 amino acids, a substitution of less than 30 amino acids, a substitution of less than 25 amino acids, a substitution of less than 20 amino acids, a substitution of less than 15 amino acids, a substitution of less than 10 amino acids, a substitution of less than 5 amino acids, a substitution of less than 4 amino acids, a substitution of less than 3 amino acids or a substitution of less than 2 amino acids relative to the HCDR1, HCDR2 and HCDR3 of the reference heavy chain variable region and the LCDR1, LCDR2 and LCDR3 of the reference light chain variable region. Alternatively, mutations can be introduced randomly along all or part of the coding sequence, for example by saturation mutagenesis, and the resulting mutants can be screened for the biological activity to identify mutants that retain the activity.

Cancer Treatment

In the present invention, the antibody, antigen-binding fragment or derivative disclosed herein can be used in certain therapeutic and diagnostic methods.

The present invention will further describe an antibody-based therapy administering the antibody disclosed herein to a patient, e.g., an animal, a mammal and a human, to treat one or more disorders or conditions described herein. The therapeutic compounds disclosed herein include, but are not limited to, the antibodies disclosed herein (including the antigen-binding fragments and derivatives disclosed herein) and nucleic acids or polynucleotides encoding the antibodies disclosed herein (including the antigen-binding fragments and derivatives disclosed herein).

The antibody disclosed herein may also be used to treat or inhibit cancers. TIGIT can be overexpressed in tumor cells. TIGIT from tumors can bind to PD-1 on immune cells, thereby limiting the immunity of anti-tumor T cells. Results of using small molecule inhibitors or monoclonal antibodies targeting TIGIT in mouse tumor models indicate that therapies targeting TIGIT are important alternatives and realistic approaches to effectively control tumor growth. As demonstrated in the examples, anti-TIGIT antibodies can activate the adaptive immune response mechanism, thereby increasing the survival rate of cancer patients.

Accordingly, in some embodiments, a method for treating a cancer in a patient in need is provided. In one embodiment, the method entails administering to the patient an effective dose of the antibody disclosed herein. In some embodiments, at least one cancer cell (e.g., stromal cell) in the patient expresses or overexpresses TIGIT, or expresses TIGIT upon induction. For example, induction of TIGIT expression can be accomplished by administering a tumor vaccine or a radiation therapy.

Tumors expressing TIGIT protein include bladder cancer, non-small cell lung cancer, renal cancer, breast cancer, urethral carcinoma, colon cancer, head and neck cancer, squamous cell carcinoma, Merkel cell carcinoma, gastrointestinal cancer, gastric cancer, esophageal cancer, ovarian cancer and small cell lung cancer. Accordingly, the antibody disclosed herein can be used to treat any one or more of such cancers.

Also provided herein are cell therapies, such as chimeric antigen receptor (CAR) T cell therapies. Suitable cells can be used to contact the anti-TIGIT antibody disclosed herein (or alternatively, be engineered to express the anti-TIGIT antibody disclosed herein). After such contacting or engineering, the cells can be introduced into a cancer patient in need. The cancer patient may have any type of cancer described herein. The cells (e.g., T cells) include, but are not limited to, the following types such as tumor-infiltrating T lymphocytes, CD4+ T cells, CD8+ T cells, and combinations thereof.

In some embodiments, the cell is isolated from the cancer patient. In some embodiments, the cell is provided by a donor or a cell bank. Adverse immune response can be minimized when the cell is isolated from the cancer patient.

The antibody or the antigen-binding fragment or derivative thereof disclosed herein can be used to treat, prevent, diagnose and/or prognose other diseases or conditions associated with increased cell viability, including, but not limited to, the progression or metastasis of malignancies and/or associated disorders, the disorders including leukemia {including acute leukemia [e.g., acute lymphocytic leukemia, acute myeloid leukemia (including myeloblastic, promyelocytic, myelomonocytic, monocytic and erythroleukemia)] and chronic leukemia [e.g., chronic myelocytic (granulocytic) leukemia and chronic lymphocytic leukemia]

}, polycythemia vera, lymphoma (e.g., Hodgkin's lymphoma and non-Hodgkin's lymphoma), multiple myeloma, Waldenstrom's macroglobulinemia, heavy chain disease, and solid tumors, including, but not limited to, sarcomas and cancers such as fibrosarcoma, myxosarcoma, liposarcoma, chondrosarcoma, osteogenic sarcoma, chordoma, angiosarcoma, endotheliosarcoma, lymphangiosarcoma, lymphangioendothelial sarcoma, synovioma, mesothelioma, Ewing's tumor, leiomyosarcoma, rhabdomyosarcoma, colon cancer, pancreatic cancer, breast cancer, thyroid cancer, endometrial cancer, melanoma, ovarian cancer, prostate cancer, squamous cell carcinoma, basal cell carcinoma, adenocarcinoma, sweat gland carcinoma, sebaceous carcinoma, papillary carcinoma, papillary adenocarcinoma, cystadenocarcinoma, medullary carcinoma, bronchial carcinoma, renal cell carcinoma, liver cancer, bile duct cancer, choriocarcinoma, seminoma, embryonal carcinoma, Wilms' tumor, cervical cancer, testicular tumor, lung cancer, small cell lung cancer, bladder cancer, epithelial cancer, glioma, astrocytoma, medulloblastoma, craniopharyngioma, ependymoma, pinealoma, hemangioblastoma, acoustic neuroma, oligodendroglioma, meningioma, neuroblastoma and retinoblastoma.

Combination Therapies

In other embodiments, the composition disclosed herein is administered in combination with an antineoplastic agent, an antiviral agent, an antibacterial agent, an antibiotic agent or an antifungal agent. Any of such agents known in the art may be administered in the compositions disclosed herein.

In other embodiments, the composition disclosed herein is administered in combination with a chemotherapeutic agent. Chemotherapeutic agents that can be administered with the composition disclosed herein include, but are not limited to, antibiotic derivatives (e.g., doxorubicin, bleomycin, daunorubicin and actinomycin D), antiestrogens (e.g., tamoxifen), antimetabolites (e.g., fluorouracil, 5-FU, methotrexate, floxuridine, interferon α-2b, glutamic acid, mithramycin, mercaptopurine and 6-thioguanine), cytotoxic agents (e.g., carmustine, BCNU, lomustine, CCNU, cytarabine, cyclophosphamide, estramustine, hydroxyurea, procarbazine, mitomycin, busulfan, cisplatin and vincristine sulfate), hormones (e.g., medroxyprogesterone, estramustine sodium phosphate, ethinylestradiol, estradiol, megestrol acetate, methyltestosterone, stilbestrol diphosphate, chlorotrianisene and testolactone), nitrogen mustard derivatives (e.g., melphalan, chlorambucil, dichloromethyl diethylamine (mechlorethamine) and thiotepa), steroids and combinations thereof (e.g., betamethasone sodium phosphate), and other compounds (such as dacarbazine, asparaginase, mitotane, vincristine sulfate, vinblastine sulfate and etoposide).

In some embodiments, the composition disclosed herein is administered in combination with a cytokine. Cytokines that can be administered with the composition disclosed herein include, but are not limited to, IL-2, IL-3, IL-4, IL-5, IL-6, IL-7, IL-10, IL-12, IL-13, IL-15, CD40, CD40L and TNF-α.

In some embodiments, the composition disclosed herein is administered in combination with other therapeutic or prophylactic regimens, such as radiotherapy.

The present invention further provides a combination therapy comprising use of one or more anti-TIGIT antibodies disclosed herein and a second anti-cancer agent (chemotherapeutic agent). Examples of the chemotherapeutic agents include immunotherapeutic agents, including but not limited to therapeutic antibodies suitable for treating a patient. Some examples of the therapeutic antibodies include simtuzumab, abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, narnatumab, naptumomab, necitumumab, nimotuzumab, nofetumomab, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49 and 3F8. Rituximab can be used for treating indolent B-cell cancers, including marginal zone lymphoma, WM, CLL and small cell lymphocytic lymphoma. The combination of rituximab and chemotherapeutic agents is particularly effective.

In some embodiments, the compound and the composition disclosed herein may be used or combined with one or more other therapeutic agents. The one or more therapeutic agents include, but are not limited to, Ab1 inhibitors, activated CDC kinase (ACK), adenosine A2B receptor (A2B), apoptosis signal-regulating kinase (ASK), Auroa kinase, Bruton's tyrosine kinase (BTK), BET-bromodomains (BRDs) such as BRD4, c-Kit, c-Met, CDK activating kinase (CAK), calmodulin-dependent protein kinase (CaMK), cyclin-dependent kinase (CDK), casein kinase (CK), discoidin domain receptor (DDR), epidermal growth factor receptor (EGFR), focal adhesion kinase (FAK), Flt-3, FYN, glycogen synthase kinase (GSK), HCK, histone deacetylase (HDAC), IKKs such as IKKβε, isocitrate dehydrogenases (IDHs) such as IDH1, Janus kinase (JAK), KDR, lymphocyte-specific protein tyrosine kinase (LCK), lysyl oxidase protein, lysyl oxidase-like (LOXL) protein, LYN, matrix metalloproteinase (MMP), MEK, mitogen-activated protein kinase (MAPK), NEK9, NPM-ALK, p38 kinase, platelet-derived growth factor (PDGF), phosphorylase kinase (PK), polo-like kinase (PLK), phosphatidylinositol 3-kinase (PI3K), protein kinases (PKs) such as protein kinases A, B and/or C, PYK, spleen tyrosine kinase (SYK), serine/threonine kinase TPL2, serine/threonine kinase STK, signal transducer and activator of transcription (STAT), SRC, serine/threonine protein kinases (TBKs) such as TBK1, TIE, tyrosine kinase (TK), vascular endothelial growth factor receptor (VEGFR), or any combination thereof.

In some embodiments, the anti-TIGIT antibody disclosed herein can be used with immune checkpoint inhibitors Immune checkpoints are a class of molecules in the immune system that can be either an up-regulating signal (a co-stimulatory molecule) or a down-regulating signal (a co-inhibitory molecule). Many cancers protect themselves from attacks of the immune system by inhibiting T cell signaling through agonists of co-inhibitory molecules or antagonists of co-stimulatory molecules Immune checkpoint agonists or antagonists may help to prevent this protective mechanism. The immune checkpoint agonist or antagonist may target any one or more of the following checkpoint molecules: PD-L1, PD-1, CTLA-4, LAG-3 (also known as CD223), CD28, CD122, 4-1BB (also known as CD137), TIM3, OX-40/OX40L, CD40/CD40L, LIGHT, ICOS/ICOSL, GITR/GITRL, TIGIT, CD27, VISTA, B7H3, B7H4, HEVM or BTLA (also known as CD272). In some embodiments, the immune checkpoint inhibitor is an anti-PD-1 antibody or an anti-PD-L1 antibody. In some embodiments, the anti-PD-1 antibody is one or more of pembrolizumab, nivolumab, toripalimab, sintilimab, tislelizumab, camrelizumab and genolimzumab. In some embodiments, the anti-PD-1 antibody is pembrolizumab. In some embodiments, the anti-PD-L1 antibody is one or more of atezolizumab, avelumab, durvalumab, envafolimab and cosibelimab. In some embodiments, the anti-PD-L1 antibody is atezolizumab.

For any of the above combination therapies, the anti-TIGIT antibody may be administered simultaneously or separately with the other anti-cancer agent. When administered separately, the anti-TIGIT antibody can be administered before or after administration of the other anti-cancer agent.

Infection Treatment

As demonstrated in the experimental examples, the antibodies disclosed herein can activate an immune response and thus be used for treating infections.

Infections are invasion of pathogenic factors in tissues, their reproduction, and the response of the host tissues to these factors and their toxins. Infections may be caused by infectious agents, such as viruses, viroids, prions, bacteria, nematodes such as parasitic ascarids and pinworms, arthropods such as ticks, mites, fleas and lice, fungi such as tinea, and other macroparasites such as cestodes and other worms. In a certain aspect, the infectious agent is a bacterium, such as a gram-negative bacterium. In a certain aspect, the infectious agent is a virus, such as a DNA virus, an RNA virus, and a retrovirus. Non-limiting examples of viruses include adenovirus, coxsackievirus, Epstein-Barr virus, hepatitis A virus, hepatitis B virus, hepatitis C virus, herpes simplex virus type 1, herpes simplex virus type 2, cytomegalovirus, human herpes virus type 8, HIV, influenza virus, measles virus, mumps virus, human papilloma virus, parainfluenza virus, poliovirus, rabies virus, respiratory syncytial virus, rubella virus and varicella-zoster virus.

The antibodies disclosed herein can also be used for treating infectious diseases caused by microorganisms, or for killing microorganisms by targeted binding of the microorganisms to immune cells for the purpose of eliminating the microorganisms. In a certain aspect, the microorganism is a virus, including RNA and DNA viruses, a gram-positive bacterium, a gram-negative bacterium, a protozoan or a fungus. Table 4 provides non-limiting examples of infectious diseases and related microorganisms.

Therapeutic Methods

The specific dosage and regimen for any particular patient will depend upon a variety of factors including the particular antibody and the antigen-binding fragment or derivative thereof used, the age and body weight of the patient, general health condition, sex and diet, and the time of administration, frequency of excretion, drug combination and the severity of the particular disease being treated. These factors are judged by medical caregivers included within the scope of those of ordinary skills in the art. The dosage will also depend on the individual patient to be treated, the route of administration, the type of the formulation, the nature of the compound used, the severity of the disease and the efficacy desired. The dosage employed can be determined by pharmacological and pharmacokinetic principles well known in the art.

The modes of administration for the antibodies and the antigen-binding fragments thereof include, but are not limited to, intradermal, intramuscular, intraperitoneal, intravenous, subcutaneous, nasal and epidural injections and oral administration. The antibody or composition can be administered by any convenient route, for example by infusion or bolus injection, or epithelial or mucocutaneous absorption (e.g., through oral mucosa, rectal and intestinal mucosa), and can be co-administered with other biologically active agents. Thus, the pharmaceutical composition comprising the antibody disclosed herein can be administered orally, rectally, parenterally, intracisternally, intravaginally, intraperitoneally, topically (e.g. by powder, ointment, drop or transdermal patch) or buccally, or by oral or nasal spray.

The term "parenteral" as used herein refers to modes of administration including intravenous, intramuscular, intraperitoneal, intrasternal, subcutaneous and intraarticular injections and infusions.

The mode of administration may be systemic or local. In addition, it may be desirable to introduce the antibody disclosed herein into the central nervous system by any suitable route, including intraventricular and intrathecal injections; intraventricular injection may be assisted by an intraventricular catheter connected to, for example, a reservoir (which may be an Ommaya reservoir). Pulmonary administration is also possible, for example by use of an inhaler or nebulizer, and by use of nebulized formulations.

It may be desirable to administer the antibody polypeptide or the composition disclosed herein locally to an area in need of treatment, which may be done by, but is not limited to, the following: local infusion during surgery, for example topical application in combination with a post-operative wound dressing, achieved by injection, a catheter, a suppository or an implant which is a porous, non-porous or gelatinous material, including membranes (e.g. silicone rubber membranes) or fibers. Preferably, when the protein disclosed herein (including antibodies) is administered, care must be taken to use materials that do not absorb the protein.

In some embodiments, the composition disclosed herein comprises a nucleic acid or a polynucleotide encoding a protein, which can be administered in vivo to facilitate expression of the encoded protein by constructing the nucleic acid or the polynucleotide as part of a suitable nucleic acid expression vector, which can then be made intracellular by administering that part of the vector through, for example, the following methods: by using a retroviral vector (see U.S. Pat. No. 4,980,286), by direct injection, by using microprojectile bombardment (e.g., gene gun; Biolistic, Dupont), by coating with lipids or cell surface receptors or transfection reagents, or by ligation with homeobox-like peptides with known capability of entering the nucleus (see, e.g., Joliot et al., 1991, Proc. Natl. Acad. Sci. USA 88:1864-1868). Alternatively, the nucleic acid can be introduced into the cell and integrated into the host cell DNA for expression by homologous recombination.

The dose of the antibody disclosed herein that will be effective in treating, inhibiting and preventing an inflammatory, immune or malignant disease, disorder or condition can be determined by standard clinical techniques. In addition, in vitro experiments may optionally be employed to help the determination of optimal dose ranges. The exact dose for the formulation to be used will also depend on the route of administration and the severity of the disease, disorder or condition, and will be decided according to the judgment of the physician and the situation of each patient. Effective doses can be extrapolated from dose-response curves obtained in vitro or in animal model test systems.

In some embodiments, the antibody disclosed herein is generally administered to a patient at a dose of 0.1 mg/kg to 100 mg/kg, 0.1 mg/kg to 20 mg/kg, or 1 mg/kg to 10 mg/kg. Generally, human antibodies have a longer half-life in humans than antibodies from other species due to the immune response to foreign polypeptides. Thus, for human antibody, lower doses and dosing frequencies are generally feasible. In addition, the dose and frequency for administration of the antibody disclosed herein can be reduced by enhancing the uptake and tissue penetration ability (e.g., into the brain) of the antibody through modifications such as lipidation.

Methods for treating infectious or malignant diseases, disorders or conditions comprising administering the antibody, the antigen-binding fragment or derivative disclosed herein are generally tested in vitro, followed by in vivo tests for desired therapeutic or prophylactic activities in an acceptable animal model, and finally administration in human. Suitable animal models (including transgenic animals) are well known to those of ordinary skills in the art. For example, in vitro assays for demonstrating therapeutic use of the antibody or the antigen-binding fragment disclosed herein include the effect of the antibody or the antigen-binding fragment on a cell line or a patient tissue sample. The effect of the antibody or the antigen-binding fragment on the cell line and/or the tissue sample can be detected using techniques known to those skilled in the art, such as the techniques disclosed elsewhere herein. In accordance with the teachings of the present invention, in vitro assays that can be used to determine whether to administer a specific antibody or antigen-binding fragment include in vitro cell culture experiments, wherein a patient tissue sample is cultured in a culture medium and is exposed to or otherwise administered with a compound, and the effect of the compound on the tissue sample is observed.

Various delivery systems are known and can be used to administer the antibody disclosed herein or the polynucleotide encoding the antibody disclosed herein, e.g., encapsulation in liposomes, microparticles, microcapsules, recombinant cells capable of expressing the compound, receptor-mediated endocytosis (see, e.g., Wu and Wu, 1987, *J. Biol. Chem.* 262:4429-4432), construction of nucleic acids as part of a retrovirus or other vectors.

Diagnostic Methods

Overexpression of TIGIT is observed in certain tumor samples, and patients with cells overexpressing TIGIT are likely to respond to treatment with the anti-TIGIT antibody disclosed herein. Thus, the antibody disclosed herein may also be used for diagnosis and prognosis.

Preferably, a sample comprising cells may be obtained from a patient, which may be a cancer patient or a patient to be diagnosed. The cells are cells of a tumor tissue or tumor mass, a blood sample, a urine sample, or any sample from the patient. After an optional pretreatment of the sample, the sample can be incubated with the antibody disclosed herein in a condition that allows the antibody to interact with TIGIT protein that may be present in the sample. By methods such as ELISA, the presence of TIGIT protein in the sample can be detected using the anti-TIGIT antibody.

The presence of TIGIT protein (at any amount or concentration) in a sample can be used to diagnose a cancer, which may be an indication that the patient is eligible for an antibody therapy, or an indication that the patient has (or has not) responded to a cancer therapy. For prognostic methods, one, two or more tests may be performed at a particular stage at the beginning of a cancer therapy to indicate the progress of the treatment.

Compositions

The present invention further provides pharmaceutical compositions. Such composition comprises an effective dose of an antibody and an acceptable carrier. In some embodiments, the composition further comprises a second anti-cancer agent (e.g., an immune checkpoint inhibitor).

In one specific embodiment, the term "pharmaceutically acceptable" refers to materials listed in pharmacopoeia for use in animals, in particular in humans. In addition, the "pharmaceutically acceptable carrier" will generally be any type of non-toxic solid, semi-solid or liquid filler, diluent, encapsulating material, or formulation additive.

The term "carrier" refers to a diluent, adjuvant, excipient, or vehicle that is administered with an active ingredient for treatment. Such pharmaceutical carriers may be sterile liquids, such as water and oils, including oils originated from petroleum, animal, plant or synthesis, such as peanut oil, soybean oil, mineral oil and sesame oil. Water is a preferred carrier when the pharmaceutical composition is administered intravenously. Saline and solutions of glucose in water or glycerol can also be used as a liquid carrier, particularly for injection. Suitable pharmaceutical excipients include starch, glucose, lactose, sucrose, gelatin, malt, rice, flour, chalk, silica gel, sodium stearate, glycerol monostearate, talc, sodium chloride, skimmed milk powder, glycerol, propylene, glycol, water, ethanol and the like. If desired, the composition may also comprise a small amount of a wetting agent, an emulsifier, or a pH buffering agent such as acetates, citrates or phosphates. Antibacterials such as benzyl alcohol or methylparaben, antioxidants such as ascorbic acid or sodium bisulfite, chelating agents such as ethylenediamine tetraacetic acid, and tonicity adjusting agents such as sodium chloride or dextrose are also contemplated. Such compositions may be in the form of solutions, suspensions, emulsions, tablets, pills, capsules, pulvises, sustained-release formulations and the like. The composition may be formulated as a suppository using conventional binders and carriers such as triglycerides. Oral formulations may comprise standard carriers such as mannitol, lactose, starch, magnesium stearate, sodium saccharin, cellulose and magnesium carbonate of pharmaceutical grade. Examples of suitable pharmaceutical carriers are described in *Remington's Pharmaceutical Sciences* by E. W. Martin, which is incorporated herein by reference. Such composition will comprise a clinically effective dose of an antibody, preferably in purified form, together with a suitable amount of a carrier to provide a dosing form suitable for the patient. The formulation should be suitable for the administration mode. The parent formulation may be enclosed in ampoules, disposable syringes or multiple dose vials made of glass or plastic.

In some embodiments, the composition is formulated into a pharmaceutical composition suitable for intravenous injection into a human body according to conventional procedures. Typically, a composition for intravenous administration is a solution in a sterile isotonic aqueous buffer. When necessary, the composition may also comprise a solubilizer and a local anesthetic such as lidocaine, to alleviate a pain at the injection site. In general, the active ingredients are provided in a unit dosage form individually or as a mixture, for example, being encapsulated in sealed containers (such as ampoules or sachets) that can indicate the amount of the active agent, in the form of a lyophilized powder or an anhydrous concentrate. Where the composition is administered by infusion, the composition can be dispensed in infusion bottles containing sterile water or saline of pharmaceutical grade. Where the composition is administrated by injection, an ampoule for sterile water or saline for injection can be used, such that the active ingredients can be mixed before administration.

The compound disclosed herein may be formulated in a neutral or salt form. Pharmaceutically acceptable salts include salts formed with anions derived from acids such as hydrochloric acid, phosphoric acid, acetic acid, oxalic acid and tartaric acid, and salts formed with cations derived from, e.g., sodium, potassium, ammonium, calcium or iron hydroxide, isopropylamine, triethylamine, 2-ethylaminoethanol, histidine, and procaine.

In the following examples, reagents and instruments used are those conventional in the art and commercially available unless otherwise specified; the methods used are all conventional in the art, and those skilled in the art can undoubtedly implement the examples and obtain the corresponding results according to the description of the examples.

Construction of a Portion of the Cells:

Reference were made to Yu, X., et al. (2009). "The surface protein TIGIT suppresses T cell activation by promoting the generation of mature immunoregulatory dendritic cells", *Nature Immunology* 10(1):48-57 and Neumann, F., et al. (1995). "Human ribosomal protein L7 inhibits cell-free translation in reticulocyte lysates and affects the expression of nuclear proteins upon stable transfection into Jurkat T-lymphoma cells", *Nucleic Acids Research* 23(2):195-202 for techniques for constructing Jurkat cells, sAPC cells, and CTI-Jurkat cells overexpressing human TIGIT.

Construction of sAPC cells: a nucleotide sequence encoding the heavy chain variable region of a mouse anti-human CD3 single-chain antibody (SEQ ID NO: 51), a nucleotide sequence encoding a linker (SEQ ID NO: 52), a nucleotide sequence encoding the light chain variable region of a mouse anti-human CD3 single-chain antibody (SEQ ID NO: 53) and a nucleotide sequence encoding PVR (SEQ ID NO: 54) were transfected into CHO-K1 cells (ATCC, CCL-61) to obtain a sAPC cell line stably expressing human PVR on the cell membrane and the mouse anti-human CD3 single-chain antibody.

Construction of CTI-Jurkat cells: a full-length human TIGIT gene (SEQ ID NO: 55), a full-length human CD226 gene (SEQ ID NO: 56), an IL-2 response element (SEQ ID NO: 57) and a luciferase reporter gene plasmid pNFκB-TA-luc (Beyotime, D2207) were transfected into a Jurkat cell line (ATCC, Clone E6-1, TIB-152™) to obtain a CTI-Jurkat cell line capable of stably expressing human TIGIT and human CD226 molecules.

Construction of Jurkat cells overexpressing human TIGIT: a full-length human TIGIT gene (SEQ ID NO: 55) was transfected into a Jurkat cell line (ATCC, Clone E6-1, TIB-152™) to obtain a Jurkat-hTIGIT 2E6 cell line capable of stably expressing human TIGIT.

| SEQ ID NO: 51 | Heavy chain variable region of mouse anti-human CD3 single-chain antibody | gtgctagcccaggtccagctgcagcagtctggggctgaactggcaagacctggggcctcagtgaagatgtcctgcaag gcttctggctacacctttactaggtacacgatgcactgggtaaaacagaggcctggacagggtctggaatggattggatac attaatcctagccgtggttatactaattacaatcagaagttcaaggacaaggccacattgactacagacaaatcctccagca cagcctacatgcaactgagcagcctgacatctgaggactctgcagtctattactgtgcaagatattatgatgatcattactgc cttgactactggggccaaggcaccacggtgaccgtgagcgcc |
| --- | --- | --- |
| SEQ ID NO: 52 | Linker | gggggaggtggcagcggggaggtggcagcggcggcgggagctcc |
| SEQ ID NO: 53 | Light chain variable region of mouse anti-human CD3 single-chain antibody | gggggaggtggcagcggggaggtggcagcggcggcgggagctcccaaattgttctcacccagtctccagcaatcat gtctgcatctccaggggagaaggtcaccatgacctgcagtgccagctcaagtgtaagttacatgaactggtaccagcaga agtcaggcacctcccccaaaagatggatttatgacacatccaaactggcttctggagtccctgctcacttcaggggcagtg ggtctgggacctcttactctctcacaatcagcggcatggaggctgaagatgctgccacttattactgccagcagtggagta gtaacccattcacgttcggctcggggacaaagttggaaataaaccggggcggtggggatccc |
| SEQ ID NO: 54 | Full-length PVR nucleotide sequence | atggctagagctatggctgctgcttggccactgctgctggtggccctgctggtgctgtcttggcccctccaggaaccggc gacgtggtggtgcaggctccaacccaggtgcctggcttcctgggcgattccgtgacactgccttgctacctgcaggtgcc aaacatggaggtgacacacgtgagccagctgacatgggctagacatggagagtctggctccatggccgtgttccaccag acccagggcccctagctactctgagtccaagcgcctggagtttgtggctgctagactgggagctgagctgaggaatgcttc cctgcggatgtttggcctgagagtggaggacgagggcaattatacatgcctgttcgtgaccttccacagggcagccggt ctgtggatatctggctgagagtgctggccaagcccagaacacagctgaggtgcagaaggtgcagctgacaggagag cctgtgccaatggctagatgcgtgtccacaggcggcaggcccctgctcagatcacctggcactctgacctgggcggca tgcccaatacatctcaggtcccaggcttcctgtccggcaccgtgacagtgaccagcctgtggattctggtgccttccagcc aggtggatggcaagaacgtgacctgcaaggtggagcatgagagctttgagaagccacagctgctgacagtgaatctga ccgtgtactatccacccgaggtgtccatcagcggctacgacaacaattggtatctgggccagaatgaggccacactgacc tgtgatgctaggtctaaccctgagccaaccggctataattggtccaccacaatgggccactgcctccattcgctgtggctc agggagctcagctgctgatcagaccagtggacaagcccatcaacaccacactgatctgtaacgtgacaaatgctctggg cgccagacaggctgagctgaccgtgcaggtgaaggaggggcctccatctgagcattccggcatcagccgcaatgccat tatcttcctggtgctgggcatcctggtgttcctgatcctgctgggaatcggcatctacttctactggtccaagtgctccaggg aggtgctgtggcattgccatctgtgccttcctccaccgagcatgcttctgcttccgctaacggccacgtgtcttactccgct gtgtccagagagaactcctcctcccaggaccctcagacagagggcaccaggtga |
| SEQ ID NO: 57 | IL-2 response element nucleotide sequence | ggtaccattttctgagttactttgtatccccacccccttaaagaaaggag- gaaaaactgtttcatacagaaggcgttaattgc atgaattagagctatcacctaagtgtgggctaatgtaacaaagagggatttcacctacatccattcagtcagtctttggggt ttaaagaaattccaaagagtcatcagaagaggaaaaatgaaggtaatgttttttcagacaggtaaagtctttgaaaatatgtg taatatgtaaaacattttgacacccccataatattttccagaattaacagtataaattgcatctcttgttcaagagttccct atcactctcttaatcactactcacagtaacctcaactcctgccaaagctt |

| SEQ ID NO: 55 | Full-length human TIGIT nucleotide sequence | atgcgctggtgtctgctgctgatttgggcccagggactgagacaggctcctctggcttcaggaatgatgaccggcaccat<br>cgagaccaccggaaacatcagcgccgagaagggaggaagcatcatcctccagtgccacctgagtagcacaaccgcac<br>aggtcacccaggtcaattgggagcagcaggaccagctgctggccatttgcaacgccgatctgggttggcacatctctcct<br>agcttcaaggacagagtggccccaggaccaggactgggactgacactgcagagtctgaccgtgaacgacaccggcga<br>gtacttctgcatctaccacacctacccagacggcacctacacaggacggatcttcctggaggtgctggagtctagcgtgg<br>cagagcacggagccagattccagatccctctgctgggagctatggcagctacactggtcgtgatctgcaccgcagtgatc<br>gtggtcgtggctctgacacggaagaagaaggccctgagaatccacagcgtggagggagacctgagaagaaagagcg<br>ccggacaggaggagtggtctcctagcgctccttctcctccaggctcttgtgtgcaggcagaagcagctccagcaggtctc<br>tgcggagaacagagaggagaggattgcgccgagctgcacgactacttcaacgtgctgagctaccggagcctgggcaat<br>tgcagcttcttcaccgagaccggatga |
|---|---|---|
| SEQ ID NO: 56 | Full-length human CD226 nucleotide sequence | atggactaccccaccctgctgctggccctgctgcacgtgtacagggccctgtgcgaggaggtgctgtggcacacaagc<br>gtgcctttcgccgagaacatgagcctggagtgcgtgtaccctagcatgggcatcctgacccaggtggagtggttcaagat<br>cggcacccagcaggattccatcgccatctttagcccacacacgcatggtgatcaggaagccttacgccgagagagtg<br>tacttcctgaatagcaccatggccagcaataatatgaccctgttctttagaaacgcctccgaggatgacgtgggctactact<br>cctgttccctgtacacctaccctcagggcacctggcagaaggtgatccaggtggtgcagtccgatagctttgaggccgcc<br>gtgccttccaactcccacatcgtgagcgagcccgccaagaatgtgacactgacatgccagccccagatgacctggcc<br>gtgcaggccgtgaggtgggagaagatccagcctaggcagatcgatctgctgacctactgtaatctggtgcacggcagaa<br>acttcaccagcaagttccccagacagatcgtgtccaattgtcccacggcaggtggagcgtgatcgtgatccctgatgtga<br>cagtgtccgactccggcctgtacagatgctacctgcaggccagcgccggcgagaacgagaccttcgtgatgagactga<br>ccgtggccgagggcaagaccgacaatcagtacacactgtttgtggccggcggcacagtgctgctgctgctgttcgtgatc<br>agcatcaccacaatcatcgtgatctttctgaatagaagaaggagaagagagaggagagatctgttcacagagagctggg<br>atacccagaaggcccctaataactacaggtcccctatctccacatcccagcctaccaatcagtccatggatgatacaagg<br>gaggacatctacgtgaattaccctacattcagcagaagacctaagaccagagtgtga |

EXAMPLES

Example 1. Expression and Purification of PVR-Fc and TIGIT-Fc Fusion Proteins

The amino acid residue sequence of PVR extracellular region (SEQ ID NO: 1) was optimized according to human codon usage bias to obtain an optimized nucleotide sequence SEQ ID NO: 2. An enzymatic digestion site was added to and fused with a human IgG1 constant region sequence (SEQ ID NO: 28, with nucleotide sequence shown in underlined portion of SEQ ID NO: 46) by a linker (SEQ ID NOs: 6 and 7), as shown in the schematically in FIG. 1. The fused sequence was inserted into a pCDNA3.1+ vector (Invitrogen, V790-20), followed by transient transfection into 293F cells. The cell supernatant after the culture was purified by Protein A affinity chromatography, and the fusion protein obtained by the purification was named PVR-Fc.

Figure 2:
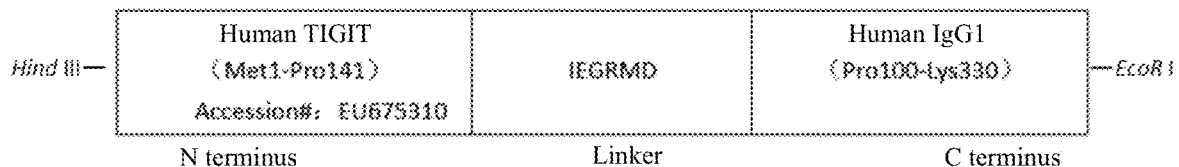
FIG. 2: A schematic diagram of the construction of TIGIT-FC fusion protein.

The amino acid residue sequence of TIGIT extracellular region (SEQ ID NO: 3) was optimized according to human codon usage bias to obtain an optimized nucleotide sequence SEQ ID NO: 48. An enzymatic digestion site was added to and fused with a human IgG1 constant region sequence (SEQ ID NO: 28, with nucleotide sequence shown in underlined portion of SEQ ID NO: 46) by a linker (SEQ ID NOs: 6 and 7), as shown in the schematically in FIG. 2. The fused sequence was inserted into a pCDNA3.1+ vector, followed by transient transfection into 293F cells. The cell supernatant after the culture was purified by Protein A affinity chromatography, and the fusion protein obtained by the purification was named TIGIT-Fc.

TABLE 1.1

Related sequences of the obtained antibodies

| Name | Sequence | SEQ ID NO: |
|---|---|---|
| Amino acid sequence of the extracellular region of human PVR (CD155), with the predicted signal peptide sequence underlined | <u>MARAMAAAWPLLLVALLVLSWPPP</u>GTGDVVVQAPTQVPGFLGDSVTL<br>PCYLQVPNMEVTHVSQLTWARHGESGSMAVFHQTQGPSYSESKRLEF<br>VAARLGAELRNASLRMFGLRVEDEGNYTCLFVTFPQGSRSVDIWLRV<br>LAKPQNTAEVQKVQLTGEPVPMARCVSTGGRPPAQITWHSDLGGMPN<br>TSQVPGFLSGTVTVTSLWILVPSSQVDGKNVTCKVEHESPEKPQLLT<br>VNLTVYYPPEVSISGYDNNWYLGQNEATLTCDARSNPEPTGYNWSTT<br>MGPLPPFAVAQGAQLLIRPVDKPINTTLICNVTNALGARQAELTVQV<br>KEGPPSEHSGISRN | 1 |
| DNA sequence of the extracellular region of human PVR (CD155), with the predicted signal peptide sequence underlined | <u>atggctagagctatggctgctgcttggccactgctgctggtggccctgct<br>ggtgctgtcttggcccc</u>ctccaggaaccggcgacgtggtggtgcaggctc<br>caacccaggtgcctggcttcctgggcgattccgtgacactgccttgctac<br>ctgcaggtgccaaacatggaggtgacacacgtgagccagctgacatgggc<br>tagacatggagagtctgcctccatggccgtgttccaccagacccagggcc<br>ctagctactctgagtccaagcgcctggagtttgtggctgctagactggga<br>gctgagctgaggaatgcttccctgcggatgtttggcctgagagtggagga<br>cgagggcaattatacatgcctgttcgtgacctttccacagggcagccggt<br>ctgtggatatctggctgagagtgctggccaagccccagaacacagctgag<br>gtgcagaaggtgcagctgacaggagagcctgtgccaatggctagatgcgt<br>gtccacaggcggcaggccccctgctcagatcacctggcactctgacctgg<br>gcggcatgcccaatacatctcaggtcccaggcttcctgtccggcaccgtg<br>acagtgaccagcctgtggattctggtgccttccagccaggtggatggcaa<br>gaacgtgacctgcaaggtggagcatgagagctttgagaagccacagctgc | 2 |

TABLE 1.1-continued

Related sequences of the obtained antibodies

| Name | Sequence | SEQ ID NO: |
|---|---|---|
| | tgacagtgaatctgaccgtgtactatccacccgaggtgtccatcagcggc tacgacaacaattggtatctgggccagaatgaggccacactgacctgtga tgctaggtctaaccctgagccaaccggctataattggtccaccacaatgg gcccactgcctccattcgctgtggctcagggagctcagctgctgatcaga ccagtggacaagcccatcaacaccacactgatctgtaacgtgacaaatgc tctgggcgccagacaggctgagctgaccgtgcaggtgaaggagggccctc catctgagcattccggcatcagccgcaat | |
| Human TIGIT sequence, with predicted signal peptide sequence underlined | <u>MRWCLLLIWAQGLRQAPLASG</u>MMTGTIETTGNISAEKGGSIILQCHL SSTTAQVTQVNWEQQDQLLAICNADLGWHISPSFKDRVAPGPGLGLT LQSLTVNDTGEYFCIYHTYPDGTYTGRIFLEVLESSVAEHGARFQIP | 3 |
| Human TIGIT nucleotide sequence, with predicted signal peptide sequence underlined | <u>atgcgctggtgtctgctgctgatttgggcccagggactgagacaggctcc tctggcttcagg</u>aatgatgaccggcaccatcgagaccaccggaaacatca gcgccgagaagggaggaagcatcatcctccagtgccacctgagtagcaca accgcacaggtcacccaggtcaattgggagcagcaggaccagctgctggc catttgcaacgccgatctgggttggcacatctctcctagcttcaaggaca gagtggccccaggaccaggactgggactgacactgcagagtctgaccgtg aacgacaccggcgagtacttctgcatctaccacacctacccagacggcac ctacacaggacggatcttcctggaggtgctggagtctagcgtggcagagc acggagccagattccagatccct | 48 |
| Monkey TIGIT sequence, with predicted signal peptide sequence underlined | <u>MRWCLFLIWAQGLRQAPLASG</u>MMTGTIETTGNISAKKGGSVILQCHL SSTMAQVTQVNWEQHDHSLLAIRNAELGWHIYPAFKDRVAPGPGLGL TLQSLTMNDTGEYFCTYHTYPDGTYRGRIFLEVLESSVAEHSARFQI PLLGAMAMMLVVICIAVIVVVVLARKKKSLRIHSVESGLQRKSTGQE EQIPSAPSPPGSCVQAEAAPAGLCGEQQGDDCAELHDYFNVLSYRSL GSCSFFTETG | 4 |
| Mouse TIGIT sequence, with predicted signal peptide sequence underlined | <u>MHGWLLLVWVQGLIQAAFLATAIG</u>ATAGTIDTKRNISAEEGGSVILQ CHFSSDTAEVTQVDWKQQDQLLAIYSVDLGWHVASVFSDRVVPGPSL GLTFQSLTMNDTGEYFCTYHTYPGGIYKGRIFLKVQESSDDRNGLAQ FQTAPLGGTMAAVLGLICLMVTGVTVLARKDKSIRMHSIESGLGRTE AEPQEWNLRSLSSPGSPVQTQTAPAGPCGEQAEDDYADPQEYFNVLS YRSLESFIAVSKTG | 5 |
| Fusion protein linker | IEGRMD | 6 |
| DNA sequence of fusion protein linker | ATTGAAGGTAGAATGGAT | 7 |
| Heavy chain variable region of positive control antibody (Tiragolumab) | EVQLQQSGPGLVKPSQTLSLTCAISGDSVSSNSAAWNWIRQSPSRGLEWL GKTYYRFKWYSDYAVSVKGRITINPDTSKNQFSLQLNSVTPEDTAVFYCT RESTTYDLLAGPFDYWGQGTLVTVSS | 8 |
| Light chain variable region of positive control antibody (Tiragolumab) | DIVMTQSPDSLAVSLGERATINCKSSQTVLYSSNNKKYLAWYQQKPGQPP NLLIYWASTRESGVPDRFSGSGSGTDFTLTISSLQAEDVAVYYCQQYYST PFTFGPGTKVEIK | 9 |
| Heavy chain variable region of positive anti-TIGIT antibody (10A7) | EVQLVESGGGLTQPGKSLKLSCEASGFTFSSFTMHWVRQSPGKGLEWVAF IRSGSGIVFYADAVRGRFTISRDNAKNLLFLQMNDLKSEDTAMYYCARRP LGHNTFDSWGQGTLVTVSS | 10 |
| Light chain variable region of positive anti-TIGIT antibody (10A7) | DIVMTQSPSSLAVSPGEKVTMTCKSSQSLYYSGVKENLLAWYQQKPGQSP KLLIYYASIRFTGVPDRFTGSGSGTDYTLTITSVQAEDMGQYFCQQGINN PLTFGDGTKLEIKR | 11 |
| Humanized antibody heavy chain signal peptide | MEFGLSWVFLVAILKGVQC | 12 |

TABLE 1.1-continued

Related sequences of the obtained antibodies

| Name | Sequence | SEQ ID NO: |
|---|---|---|
| DNA sequence of humanized antibody light chain signal peptide | ATGGAGTTTGGGCTGAGCTGGGTTTTCCTTGTTGCTATATTAAAAGG TGTCCAGTGT | 13 |
| Amino acid sequence of humanized antibody light chain signal peptide | MDMRVLAQLLGLLLLCFPGARC | 14 |
| DNA sequence of humanized antibody light chain signal peptide | ATGGACATGAGGGTGCTGGCCCAGCTGCTGGGACTGCTGCTGCTGTG CTTCCCAGGCGCCAGATGC | 15 |
| Amino acid sequence of mouse anti-human TIGIT antibody light chain signal peptide | MKLPVRLLVLMFWIPASSS | 16 |
| DNA sequence of mouse anti-human TIGIT antibody light chain signal peptide | ATGGAGACAGACACACTCCTGCTATGGGTACTGCTGCTCTGGGTTCC AGGTTCCACTGGT | 17 |
| Amino acid sequence of mouse anti-human TIGIT antibody heavy chain signal peptide | MERHWIFLFLFSVTAGVHS | 18 |
| DNA sequence of mouse anti-human TIGIT antibody heavy chain signal peptide | ATGGAGCGGCACTGGATCTTCCTGTTCCTGTTCTCCGTGACCGCCGG CGTGCACTCC | 19 |

Example 2. Production of Mouse Anti-Human TIGIT Antibody

Female Balb/c mice (Guangdong Medical Laboratory Animal Center) aged 6-8 weeks were immunized with a fusion protein of human TIGIT extracellular region and human IgG-Fc, i.e., the TIGIT-Fc described in Example 1. A secondary immunization was performed 2-3 weeks after the primary immunization, and a booster dose was given about 3 weeks after that. Spleen lymphocytes were collected from excised spleen, and were fused with myeloma cells (Sp2/0 cells, Cell Bank of Type Culture Collection Committee of the Chinese Academy of Sciences, Cat. No. TCM18). Hybridoma cells were screened by detecting the presence of an effective binding to TIGIT-Fc. Positive hybridoma cells were further subcloned by dilution cloning, and screened again by identifying the binding capacity to TIGIT-Fc and the ability to block the binding between TIGIT-Fc and PVR-Fc. 6 monoclonal hybridoma cell strains were obtained, in which 1 monoclonal hybridoma strain 10D8 demonstrated superior characteristics and properties in various aspects.

By the method described in Bradbury, A., (2010) "Cloning Hybridoma cDNA by RACE", Antibody Engineering, edited by R. Kontermann and S. Dilbel, Berlin, Heidelberg, Springer Berlin Heidelberg, pp. 15-20, specific primers were synthesized and the target gene of the antibody of the hybridoma cells was cloned. The hybridoma sequencing process was as follows: 1) the hybridoma cells were thawed, placed into T25 cell culture flasks containing RPMI1640 culture medium (containing 10% of FBS), and cultured for 2 generations; 2) 5 million hybridoma cells were harvested and the RNA was extracted with the EasyPure RNA kit (Beijing TransGen Biotech Co. Ltd., Cat. No.: ER101); 3) with extracted RNA as the template, the cDNA was synthesized using a reverse transcription kit (Beijing TransGen Biotech Co. Ltd., Cat. No.: AT321); 4) with the cDNA as the template, an antibody sequence was amplified using a synthesized specific primer to obtain a target band. Fastpfu (Beijing TransGen Biotech Co. Ltd., Cat. No.: AP221) was used to ensure that no mutation occurred during the amplification; 5) the amplified target fragments of the heavy chain and the light chain were cloned into blunt-ended cloning vectors (Beijing TransGen Biotech Co. Ltd., Cat. No.:

CB111), and were used to coat plates; 6) after the clones were well cultured, 5 heavy chain clones and 5 light chain clones were selected and sent to Sangon Biotech (Shanghai) Co., Ltd. for sequencing; 7) the sequencing result was analyzed by using NCBI blast Tool, NCBI IGBlast Tool and other analysis programs to find out the heavy chain variable region sequence and the light chain variable region sequence of the antibody; 8) the variable region sequences of the mouse anti-human TIGIT antibody were subjected to codon optimization based on mouse codon usage bias and to sequence synthesis. The synthesized variable region sequences were fused with the mouse IgG2a heavy chain constant region frameworks (SEQ ID NO: 31, SEQ ID NO: 49) and the mouse κ light chain constant region frameworks (SEQ ID NO: 32, SEQ ID NO: 50) and the fused sequences were cloned into pCDNA3.1+ vectors. The heavy and light chain plasmids were transiently transfected into CHO-S cells (Bibco, Cat. No.: A29133) in a ratio of 1:1, and the resulting antibody was the recombinant mouse anti-human TIGIT antibody designated m10D8.

The sequence of the heavy chain V region of m10D8 is set forth in SEQ ID NO: 20, and the sequence of the light chain V region is set forth in SEQ ID NO: 24. The m10D8 antibody HCDR1 sequence was SSYGMS (SEQ ID NO: 21), the HCDR2 sequence was TINSNGGSTYYPDSVKG (SEQ ID NO: 22), and the HCDR3 sequence was LGTGTLGFAY (SEQ ID NO: 23); the LCDR1 sequence was KASQDVKTAVS (SEQ ID NO: 25), the LCDR2 sequence was WASTRHT (SEQ ID NO: 26), and the LCDR3 sequence was QQHYSTPWT (SEQ ID NO: 27).

Figure 3:
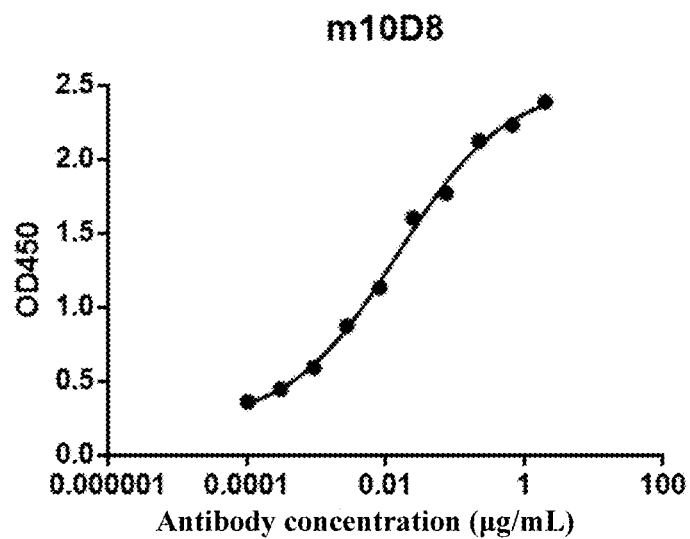
FIG. 3: ELISA results of m10D8 antibody and human TIGIT.
Figure 4:
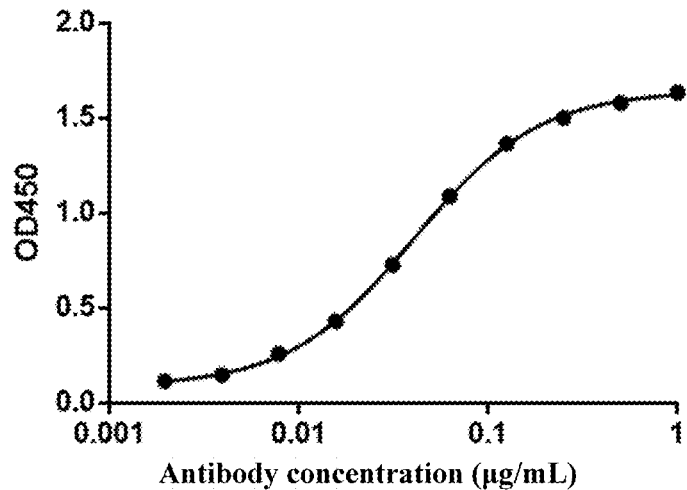
FIG. 4: ELISA results of m10D8 antibody and monkey TIGIT.
Figure 5:
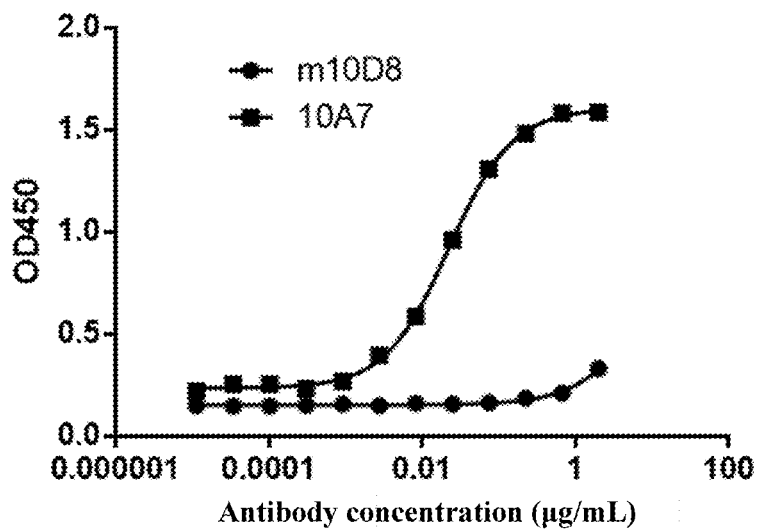
FIG. 5: ELISA results of m10D8 antibody and mouse TIGIT.

The antibody obtained by recombinant expression was further validated by ELISA for its binding capacity to human TIGIT (FIG. 3), monkey TIGIT (FIG. 4) and mouse TIGIT (FIG. 5). The positive control antibody was 10A7 antibody (a hamster anti-mouse TIGIT antibody, set forth in SEQ ID NO: 10, SEQ ID NO: 11, SEQ ID NO: 28 and SEQ ID NO: 30). The results showed that m10D8 can bind to human TIGIT and monkey TIGIT with proper affinity, but not to mouse TIGIT. The m10D8 antibody was subjected to an affinity assay using a Biacore-SPR system, giving an association rate constant of 1.02E+06 (1/Ms), a dissociation rate constant of 2.00E-04 (1/s) and an equilibrium dissociation constant $K_D$ of 1.97E-10 (M).

TABLE 2.1

Anti-TIGIT antibodies and related CDR sequences

| Name | Sequence | SEQ ID NO: |
|---|---|---|
| Amino acid sequence of mouse anti-human TIGIT antibody m10D8 heavy chain variable region | EVKLQESGGGLVQPGGSLKLSCAASGFTESSYGMSWVRQNPD KRLELVAT INSNGGSTYYPDSVKGRFTISRDNAKNTLYLQMSSLKSEDTA MYYCARLG TGTLGFAYWGQGTLVTVSS | 20 |
| Amino acid sequence of mouse anti-human TIGIT antibody m10D8 light chain variable region | DIVMTQAHKFMSTSGGDRVSITCKASQDVKTAVSWYQQKPG QSPKLLIYW ASTRHTGVPDRFTGSGSGTDYTLTISSVQAEDLALYYCQQHY STPWTFGG GTKLEIKR | 24 |
| m10D8 HCDR1 | SSYGMS | 21 |
| m10D8 HCDR2 | TINSNGGSTYYPDSVKG | 22 |
| m10D8 HCDR3 | LGTGTLGFAY | 23 |
| m10D8 LCDR1 | KASQDVKTAVS | 25 |
| m10D8 LCDR2 | WASTRHT | 26 |
| LCDR2 mutant | WASTRAT | 43 |
| m10D8 LCDR3 | QQHYSTPWT | 27 |
| Amino acid sequence of human IgG1 heavy chain constant region | ASTKGPSVFPLAPSSKSTSGGTAALGCLVKDYFPEPVTVSWNS GALTSGV HTFPAVLQSSGLYSLSSVVTVPSSSLGTQTYICNVNHKPSNTK VDKKVEP KSCDKTHTCPPCPAPELLGGPSVFLFPPKPKDTLMISRTPEVTC VVVDVS HEDPEVKFNWYVDGVEVHNAKTKPREEQYNSTYRVVSVLTV LHQDWLNGK EYKCKVSNKALPAPIEKTISKAKGQPREPQVYTLPPSRDELTK NQVSLTC LVKGFYPSDIAVEWESNGQPENNYKTTPPVLDSDGSFFLYSKL TVDKSRW QQGNVFSCSVMHEALHNHYTQKSLSLSPGK | 28 |
| Amino acid sequence 2 of human IgG1 heavy chain constant region | ASTKGPSVFPLAPSSKSTSGGTAALGCLVKDYFPEPVTVSWNS GALTSGV HTFPAVLQSSGLYSLSSVVTVPSSSLGTQTYICNVNHKPSNTK VDKKVEP KSCDKTHTCPPCPAPELLGGPSVFLFPPKPKDTLMISRTPEVTC VVVDVS HEDPEVKFNWYVDGVEVHNAKTKPREEQYNSTYRVVSVLTV | 29 |

TABLE 2.1-continued

Anti-TIGIT antibodies and related CDR sequences

| Name | Sequence | SEQ ID NO: |
|---|---|---|
| | LHQDWLNGK<br>EYKCKVSNKALPAPIEKTISKAKGQPREPQVYTLPPSREEMTK<br>NQVSLTC<br>LVKGFYPSDIAVEWESNGQPENNYKTTPPVLDSDGSFFLYSKL<br>TVDKSRW<br>QQGNVFSCSVMHEALHNHYTQKSLSLSPGK | |
| Amino acid sequence of human IgG1 light chain constant region | RTVAAPSVFIFPPSDEQLKSGTASVVCLLNNFYPREAKVQWKV<br>DNALQSGN<br>SQESVTEQDSKDSTYSLSSTLTLSKADYEKHKVYACEVTHQG<br>LSSPVTKS<br>FNRGEC | 30 |
| Amino acid sequence of mouse IgG2a heavy chain constant region | AKTTAPSVYPLAPVCGDTTGSSVTLGCLVKGYFPEPVTLTWN<br>SGSLSSGV<br>HTFPAVLQSDLYTLSSSVTVTSSTWPSQSITCNVAHPASSTKVD<br>KKIEPR<br>GPTIKPCPPCKCPAPNLLGGPSVFIFPPKIKDVLMISLSPIVTCVV<br>VDVS<br>EDDPDVQISWFVNNVEVHTAQTQTHREDYNSTLRVVSALPIQ<br>HQDWMSGK<br>EFKCKVNNKDLPAPIERTISKPKGSVRAPQVYVLPPPEEEMTK<br>KQVTLTC<br>MVTDFMPEDIYVEWTNNGKTELNYKNTEPVLDSDGSYFMYS<br>KLRVEKKNW<br>VERNSYSCSVVHEGLHNHHTTKSFSRTPGK | 31 |
| Nucleotide sequence of mouse IgG2a heavy chain constant region | gccaagaccaccgcccctagcgtgtaccctctggcccctgtgtgtggcgataccaccggctcctc<br>cgtgaccctgggctgtctggtgaagggctacttccctgagcccgtgacccgacctggaatagcg<br>gcagcctgagcagcggcgtgcacaccttccccgccgtgctgcagtccgacctgtacaccctgtcc<br>tccagcgtgaccgtgacctcctccacctggcctagccagagcatcacctgcaacgtggctcaccc<br>cgctagcagcaccaaggtggacaagaagatcgagcccaggggcctaccatcaagccttgccct<br>ccctgcaagtgcccgctcctaacctgctgggcggcccaagcgtgttcatctttccccccaagatc<br>aaggatgtgctgatgatcagcctgagcccatcgtgacctgtgtggtggtggacgtgtccgaggat<br>gatcccgatgtgcagatcagctggttcgtgaacaacgtggaggtgcacaccgctcagacccagac<br>ccaccgggaggactataatagcaccctgagggtggtgagcgctctgcctatccagcaccaggact<br>ggatgtccggcaaggagtttaagtgtaaggtgaacaacaaggatctgcccgccccatcgagcg<br>gaccatcagcaagcccaagggcagcgtgcgggcccctcaggtttatgtgctgccccccctgag<br>gaggagatgaccaagaagcaggtgaccctgacatgcatggtgaccgacttatgcccgaggatat<br>ctacgtggagtggaccaacaatggcaagaccgagctgaactacaagaacaccgagcccgtgctg<br>gattccgacggcagctatttcatgtactccaagctgcgggtggagaagaagaactgggtggagcg<br>gaacagctatagctgctccgtggtgcacgagggcctgcacaaccaccacaccaccaagagctttt<br>cccggaccccggtaaa | 49 |
| Amino acid sequence of mouse IgG2a light chain constant region | RADAAPTVSIFPPSSEQLTSGGASVVCFLNNFYPKDINVKWKI<br>DGSERQNG<br>VLNSWTDQDSKDSTYSMSSTLTLTKDEYERHNSYTCEATHKT<br>STSPIVKS<br>FNRNEC | 32 |
| Nucleotide sequence of mouse IgG2a light chain constant region | cgtgctgacgccgcccctaccgtgagcatctttcctccctccagcgagcagctgaccagcggcgg<br>agcctccgtggtgtgctttctgaacaacttttatcctaaggacatcaatgtgaagtggaagatcgatg<br>gctccgagaggcagaatggcgtgctgaactcctggaccgatcaggactccaaggactccaccta<br>ctccatgtccagcaccctgaccctgaccaaggatgagtatgagcggcacaattcctatacctgta<br>ggctacccacaagaccagcacctcccctatcgtgaagagcttcaataggaacgagtgt | 50 |

Example 3. Ability of the Mouse Anti-Human TIGIT Antibody to Block of Binding of TIGIT to its Ligand PVR Numerous studies indicated that the function of effector T cells and NK cells can be restored by blocking the binding of TIGIT to its ligand PVR using an anti-TIGIT antibody. As such, to determine whether the binding of TIGIT to its ligand PVR can be blocked by the mouse anti-human TIGIT antibody certified by the in vitro experiment is necessary.

Figure 6:
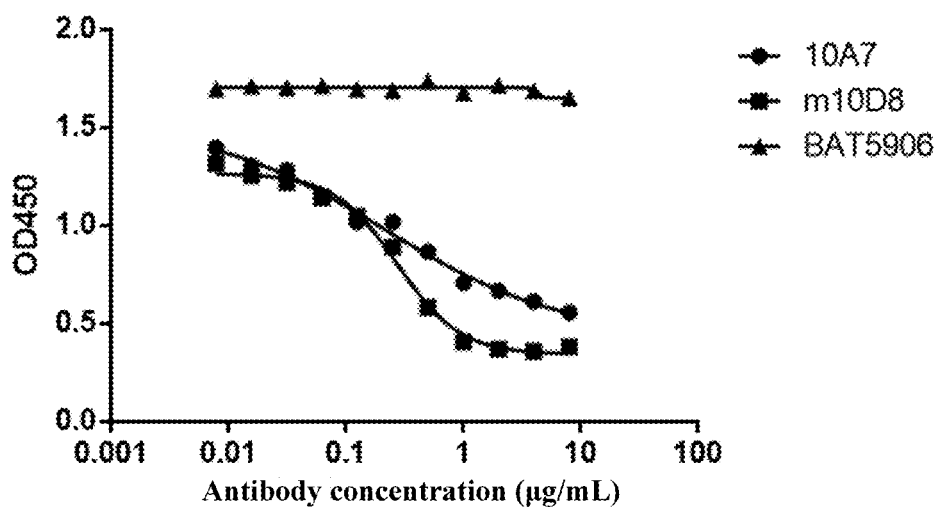
FIG. 6: Assay of the mouse anti-human TIGIT antibody for blocking the binding of TIGIT to PVR. ⬥ denotes 10A7, ■ denotes m10D8, and ▲ denotes an irrelevant antibody BAT5906 as negative control.

A proper amount of PVR-Fc protein was thawed from −80° C., and labelled using a biotin labeling kit (EZ-Link® HSulfo-NHS-LC-Biotinylation Kit, Cat. No.: 21435) purchased from Thermo Scientific according to the procedures in the instruction. The labeled protein was coded as PVR-Fc-bio. The procedures are as follows: 1) TIGIT-Fc (2 μg/mL) was immobilized on plates using 1×PBS (phosphate buffer solution) overnight at 4° C.; 2) the plates were blocked by 3% BSA in a thermostat incubator at 37° C. for 2 h; 3) PVR-Fc-bio was diluted with PBS to a final concentration of 2 μg/mL to serve as an antibody diluent; 4) m10D8, a positive control antibody 10A7 (hamster anti-mouse TIGIT antibody, as set forth in SEQ ID NO: 10, SEQ ID NO: 11, SEQ ID NO: 28 and SEQ ID NO: 30) and a negative irrelevant control antibody were diluted with the antibody diluent from an initial concentration of 8 μg/mL in a factor of two and added to the plates at a volume of 100 μL/well, and the plates were incubated in a 37° C. incubator for 2 h and washed 8 times with PBST (PBS containing 0.05% of Tween 20); 5) an enzyme-labelled secondary antibody (Jackson Immuno Research Inc., Cat. No.: 016-030-084, 1:10000 diluted) was added at 100 μL/well, and the mixture was incubated for 1 h in a 37° C. incubator and washed 8 times with PBST; 6) TMB (3,3',5,5'-tetramethylbenzidine) was added at 100 μL/well for chromogenic reaction; 7) the chromogenic reaction was terminated by adding 2 M $H_2SO_4$, and the plates were detected for the absorbance at 450 nm using a plate reader. As shown in FIG. 6, the competitive inhibition curve of m10D8 is below that of the positive antibody 10A7 in the same condition, indicating a higher ability of m10D8 to block the binding of TIGIT to its ligand PVR relative to the positive antibody.

Example 4. Biological Function Assay of the Mouse Anti-Human TIGIT Antibody

To simulate the complete activation of initial T cells requires joint participation of a first signal and a second signal. Accordingly, a method for detecting the biological activity of anti-TIGIT antibodies was developed. In this detection system, 2 cells were used. One was an artificially constructed similar antigen-presenting cell (sAPC) simultaneously overexpressing mouse anti-human CD3 single-chain antibody and PVR; the other one was an engineered Jurkat cell (CTI-Jurkat) overexpressing TIGIT and CD226 and additionally transfected with a luciferase reporter detection element based on the transcription and translation initiated by IL-2 promoter. The binding of the anti-human CD3 single-chain antibody on the sAPC cell membrane to a T cell receptor (TCR) on the Jurkat cell membrane that activates the T cell is the first signal, and the signaling caused by the interaction of PVR on the sAPC membrane and the stimulatory receptor CD226 or the inhibitory receptor TIGIT on the Jurkat cell membrane is the second signal. In the condition of no anti-TIGIT antibody participation, as the affinity of PVR for TIGIT is much higher than that of PVR for CD226, the preferential binding of PVR to TIGIT triggers TIGIT intracellular domain signaling to inhibit the proliferation of T cells and the release of cytokines; PVR also prevents CD226 on the surface of the same cell from forming functional dimers to affect the normal physiological functions of CD226; additionally, as CD226 has a weaker affinity for PVR and thus fails in competition against TIGIT for binding PVR in the same condition and in effectively activating T cells, T cells are generally in an inhibited state, and the IL-2 promoter cannot effectively initiate the transcription and translation of the luciferase reporter gene. In contrast, when an anti-TIGIT antibody is present in the detection system, the anti-TIGIT antibody can bind to TIGIT with high affinity so as to prevent the signaling of TIGIT and PVR; TIGIT can no longer prevent the dimerization of CD226, and CD226 can effectively bind to PVR to enable CD226 intracellular domain signaling and activate T cells. Thus the IL-2 promoter can effective initiate transcription and translation of the luciferase reporter gene, and accordingly, the substrate of luciferase can spontaneously emit a fluorescent signal to be captured by an instrument.

Preparation of sAPC cells: sAPC cells were cultured until the logarithmic phase in a CD CHO AGT™ medium (containing 25 μM of MSX and 400 μg/mL of hygromycin). The cultures were centrifuged at 800 rpm for 5 minutes. The sAPC cells were resuspended at a density of $4\times10^5$ cells/mL in a Ham's F-12 medium (containing 10% of PBS), and then transferred to a 96-well plate using a multi-channel pipette at 100 μL/well, i.e., $4\times10^4$ cells/well. The cells were then cultured in an 8% $CO_2$/37° C. incubator overnight. The medium was discarded, and the plate was dried using absorbent paper to remove the residual medium.

Preparation of CTI-Jurkat cells: CTI-Jurkat cells were cultured until the logarithmic phase in a 1640 medium containing 10% of FBS, and resuspended at $5\times10^6$ cells/mL in a 1640 medium (containing 1% of FBS). The CTI-Jurkat cell suspension was added to the wells containing sAPC cells at 40 μL/well, i.e., $2\times10^5$ cells/well, using a multi-channel pipette.

Preparation of antibodies: m10D8, a positive control antibody Tiragolumab (set forth in SEQ ID NO: 8, SEQ ID NO: 9, SEQ ID NO: 29 and SEQ ID NO: 30) and a negative control antibody BAT5906 (see Chinese Patent Application No. CN110003328A) were diluted in a 1640 medium (containing 1% of FBS) to 3 concentrations of 64, 32 and 16 μg/mL and vehicle controls were prepared. The diluted antibodies were then added to the wells containing sAPC and CTI-Jurkat cells at 40 μL/well (i.e., at final antibody concentrations of 32, 16, 8 and 0 μg/mL).

Figure 7:
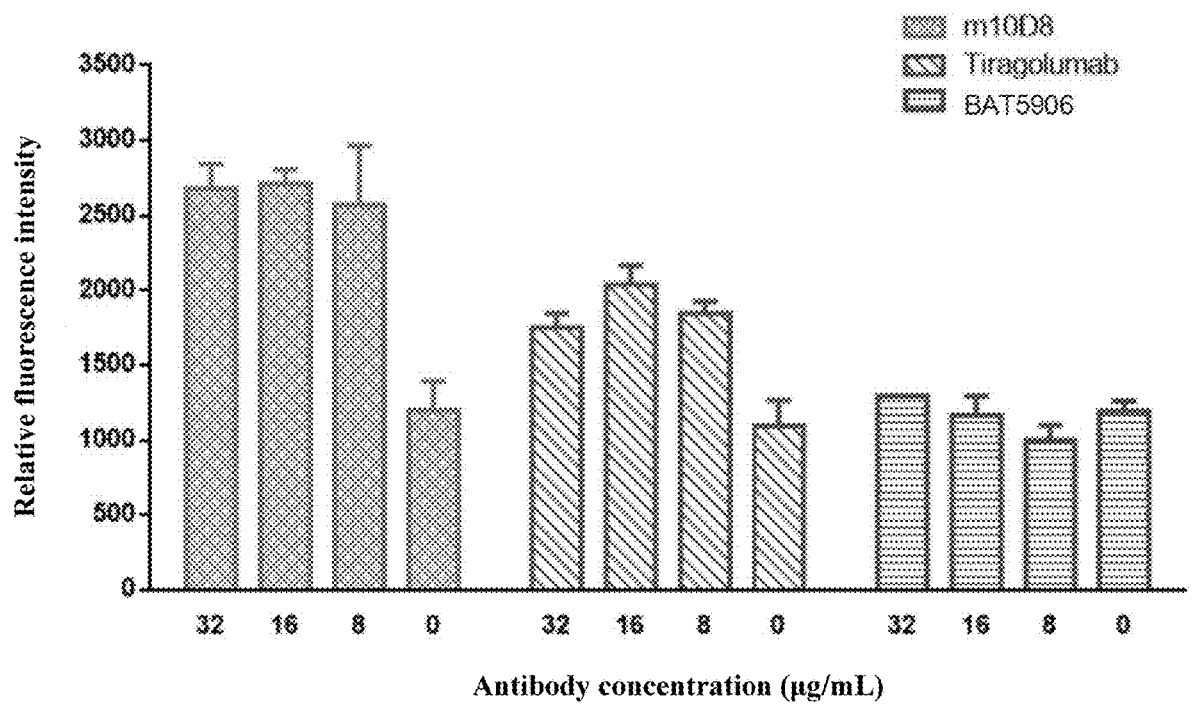
FIG. 7: Biological activity assay of the mouse anti-human TIGIT antibody. denotes m10D8, denotes an irrelevant antibody BAT5906 as negative control, and denotes Tiragolumab as positive control.

After the addition, the cell plate was incubated in an 8% $CO_2$/37° C. incubator for 4 hours, and then taken out and placed at room temperature for 10 minutes for return to room temperature. Luciferase substrate was thawed for 2 hours from −20° C. to room temperature, and added to the corresponding wells at 80 μL/well. The plate was placed in a plate reader and shaken for 5 s, and fluorescence signal was read after 10 minutes, as shown in FIG. 7. The results demonstrated that both Tiragolumab and m10D8 have the function of activating T cells, but m10D8 has the strongest ability to activate T cell functions in the same conditions.

Example 5. Humanization of Mouse Anti-Human TIGIT Antibody

Figure 8:
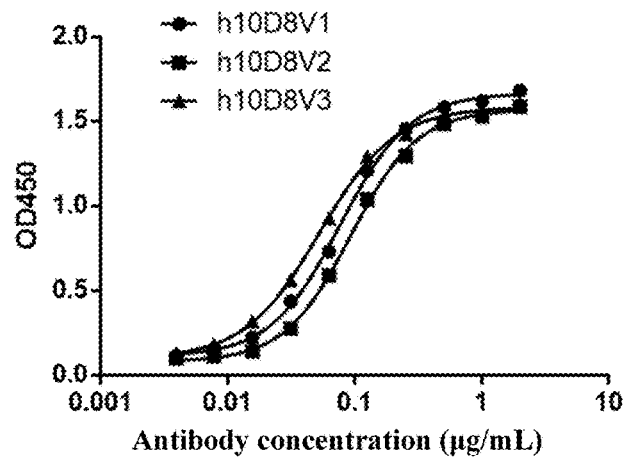
FIG. 8: Comparison of binding capacities of h10D8V1, h10D8V2 and h10D8V3 to TIGIT. denotes h10D8V1, denotes h10D8V2, and denotes h10D8V3.
Figure 9:
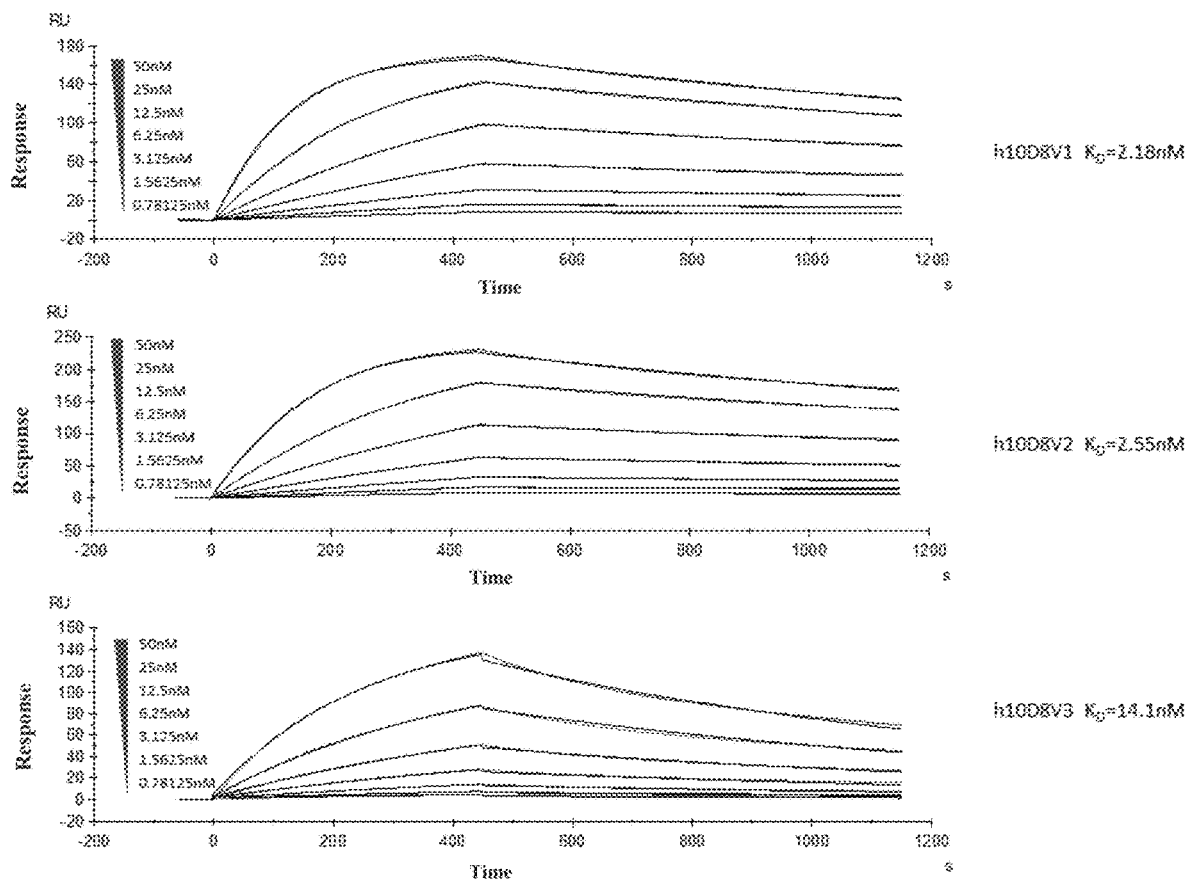
FIG. 9: Equilibrium dissociation constant determination for h10D8V1, h10D8V2 and h10D8V3 to TIGIT-his tag.
Figure 10:
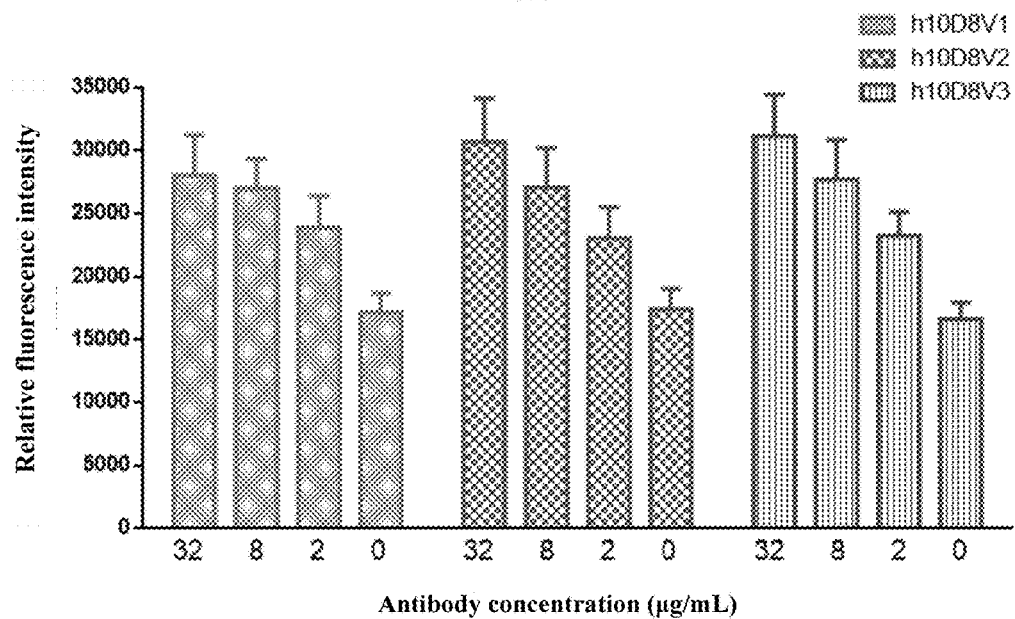
FIG. 10: Comparison of biological activities of h10D8V1, h10D8V2 and h10D8V3. denotes h10D8V1, denotes h10D8V2, and denotes h10D8V3.

The heavy chain variable region and light chain variable region of the mouse anti-human TIGIT antibody were compared to sequences in a human antibody database. The results are shown in Table 5.1. In the humanization process, for considerations of druggability and potential immunogenicity and for ensuring the high affinity of the antibody, 3 mutants were designed during the first humanization for the m10D8 humanized antibody in conjunction with bioinformatics modeling calculation: h10D8V1 (set forth in SEQ ID NO: 33, SEQ ID NO: 34, SEQ ID NO: 29 and SEQ ID NO: 30), h10D8V2 (set forth in SEQ ID NO: 33, SEQ ID NO: 34, SEQ ID NO: 28 and SEQ ID NO: 30) and h10D8V3 (set forth in SEQ ID NO: 37, SEQ ID NO: 38, SEQ ID NO: 28 and SEQ ID NO: 30). For h10D8V1 and h10D8V2, the light chain variable region framework was IGKV4-1*01, and the heavy chain variable region framework was IGHV3-23*01. For h10D8V3, the heavy chain variable region framework was IGHV3-64*04, and the light chain variable region framework was IGKV1-NL1*01. The mutant proteins were subjected to a binding assay to TIGIT and a biological activity assay. Purified h10D8V1, h10D8V2 and h10D8V3 were subjected to a binding assay to TIGIT. The ELISA results (see FIG. 8) showed that the $EC_{50}$ (half maximal effective concentration) of 3 antibodies were 0.07623 μg/mL, 0.09241 μg/mL and 0.05259 μg/mL, respectively. h10D8V3 demonstrated the strongest binding capacity to TIGIT in terms of $EC_{50}$. However, ELISA result only reflects the static antigen-antibody binding, but not the dynamic antibody-antigen association and dissociation. As such, the equilibrium dissociation constant $K_D$ of 3 antibodies to TIGIT-his tag antigen was determined by SPR-Biacore technique (see FIG. 9 and Table 5.2). It can be seen from the result that as compared to the other 2 antibodies, h10D8V3 demonstrated a slower association and a faster dissociation, and thus a greater equilibrium dissociation constant than those of the other 2 antibodies, i.e. a lower affinity than those of the other 2 antibodies. The variable regions of h10D8V1 and h10D8V2 were identical, and the only 2 differences were at amino acid residue positions 356 (EU-numbered, corresponding to Kabat-numbered position 377) and 358 (EU-numbered, corresponding to Kabat-numbered position 381) of the constant region. Thus the difference in affinity was not significant. By comparing the biological activity of h10D8V1, h10D8V2 and h10D8V3 (refer to Example 4 for the method), the results (see FIG. 10) showed that the abilities of h10D8V1, h10D8V2 and h10D8V3 to activate T cells were similar, suggesting that the 3 antibodies have similar biological activities.

TABLE 5.1

Comparison of murine antibodies to a human germline gene database (IMGT Scientific Chart)

| Sequence | Human germline gene | Similarity |
|---|---|---|
| m10D8 VH | IGHV3-23*01 | 74.1% |
| m10D8 VL | IGK3-7*04 | 69.1% |

TABLE 5.2

Equilibrium dissociation constant assay of h10D8V1, h10D8V2 and h10D8V3 to TIGIT-his tag antigen

| Ab | ka (1/Ms) | kd (1/s) | KD (M) |
|---|---|---|---|
| h10D8V1 | 2.05E+05 | 4.46E−04 | 2.18E−09 |
| h10D8V2 | 1.93E+05 | 4.92E−04 | 2.55E−09 |
| h10D8V3 | 8.12E+04 | 1.14E−03 | 1.41E−08 |

Figure 11:
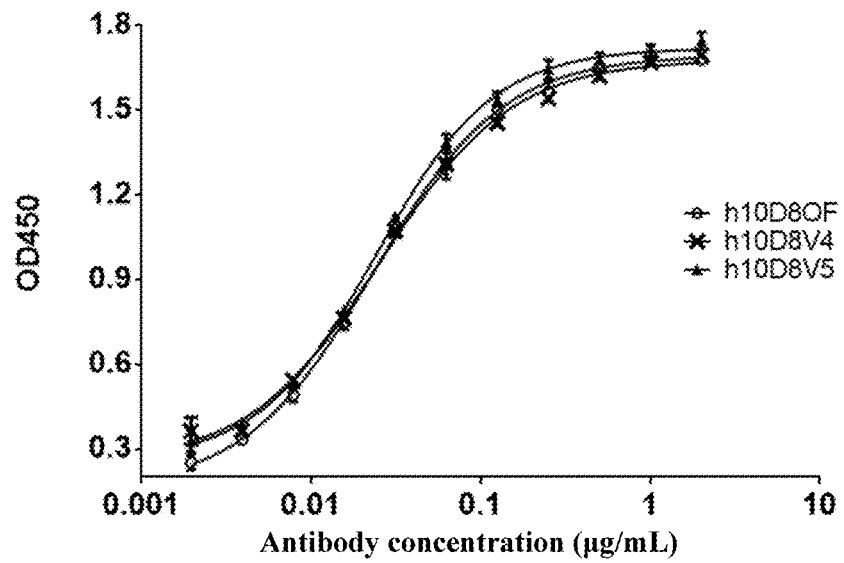
FIG. 11: Comparison of binding capacities of h10D8OF, h10D8V4, and h10D8V5 to TIGIT. denotes h10D8OF, denotes h10D8V4, and denotes h10D8V5.

According to the above results for h10D8V1, h10D8V2 and h10D8V3, a second humanization design was performed on m10D8, and 3 mutants were obtained: h10D8OF (set forth in SEQ ID NO: 35, SEQ ID NO: 36, SEQ ID NO: 28 and SEQ ID NO: 30, i.e., the heavy chain sequence is SEQ ID NO: 44 and the light chain sequence is SEQ ID NO: 45), h10D8V4 (set forth in SEQ ID NO: 39, SEQ ID NO: 40, SEQ ID NO: 28 and SEQ ID NO: 30), and h10D8V5 (set forth in SEQ ID NO: 41, SEQ ID NO: 42, SEQ ID NO: 28 and SEQ ID NO: 30). For h10D8OF, the heavy chain framework was IGHV3-64*04, and the framework used for the light chain was IGKV3D-7*01. For h10D8V4, the heavy chain framework was IGHV3-64*04, the light chain framework was IGKV4-1*01, and the main characteristic was that some amino acid residues on the framework were consistent with those on the murine antibody m10D8. For h10D8V5, heavy chain framework and the light chain framework were the same as those of h10D8V4, and the main characteristic was that the interface of the antibody and the antigen was nearly consistent with the interface of the murine antibody m10D8 and TIGIT. The binding capacities of h10D8OF, h10D8V4 and h10D8V5 to TIGIT were compared. As shown in FIG. 11, the results showed that the binding curves for the 3 antibodies h10D8OF, h10D8V4 and h10D8V5 were substantially coincident, and the $EC_{50}$ were 0.02329 µg/mL, 0.02560 µg/mL and 0.02408 µg/mL, respectively.

Figure 12:
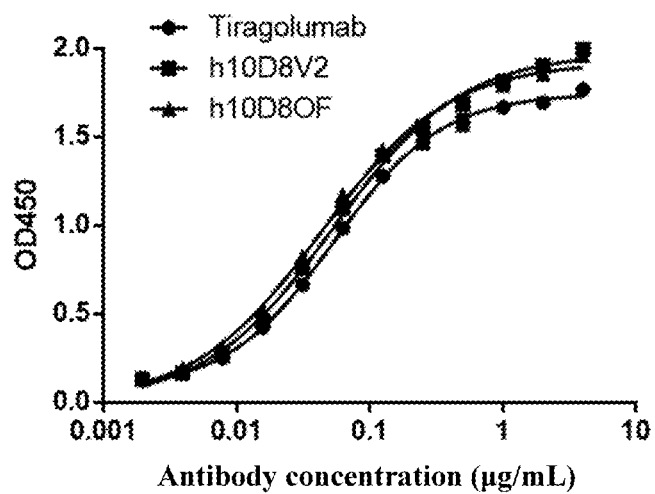
FIG. 12: Comparison of binding capacities of h10D8OF and h10D8V2 to TIGIT. denotes Tiragolumab, denotes h10D8V2, and denotes h10D8OF.
Figure 13:
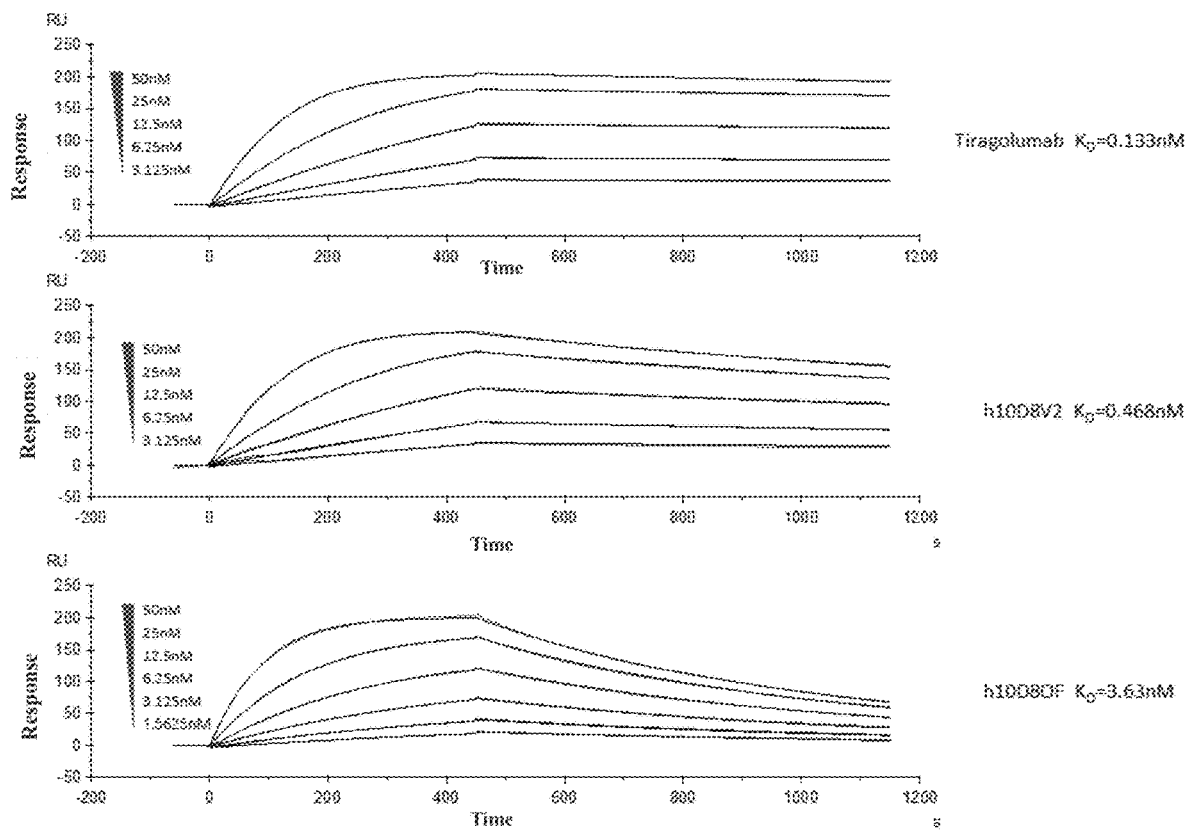
FIG. 13: Equilibrium dissociation constant determination for h10D8OF and h10D8V2 to TIGIT-his tag antigen.
Figure 14:
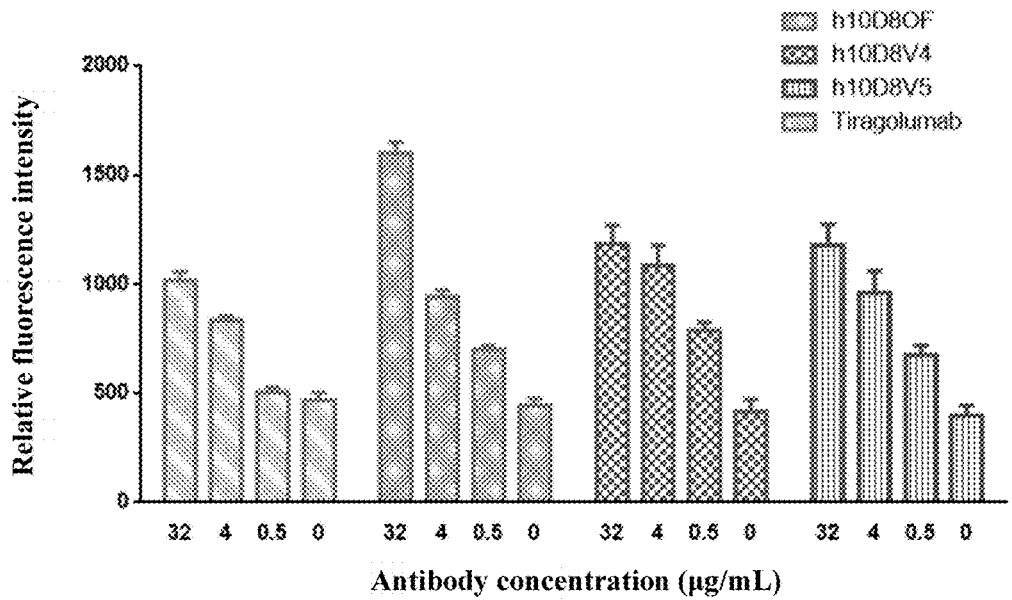
FIG. 14: Comparison of biological activities of h10D8OF, h10D8V4 and h10D8V5. denotes h10D8OF, denotes h10D8V4, denotes h10D8V5, and denotes Tiragolumab.

Meanwhile, by comparing the binding capacity of h10D8OF and h10D8V2 to TIGIT, it was found that the two binding curves were highly coincident, and the $EC_{50}$ of h10D8OF was slightly lower than that of h10D8V2. In terms of the ELISA results, the former demonstrated a higher affinity (as shown in FIG. 12). The $EC_{50}$ of h10D8OF, h10D8V2 and Tiragolumab were 0.04273 µg/mL, 0.05310 µg/mL and 0.05361 µg/mL, respectively. The equilibrium dissociation constant $K_D$ of h10D8OF, h10D8V2 and Tiragolumab to TIGIT-his tag antigen was detected by SPR-Biacore technique (as shown in FIG. 13 and Table 5.3), and by dynamic affinity detection it was found that the affinity of h10D8V2 for univalent TIGIT-his was higher than that of h10D8OF. The biological activities of h10D8OF, h10D8V4 and h10D8V5 were detected using a similar detection method to that of Example 4. The results (FIG. 14) showed that at a higher concentration (32 µg/mL), the capability of h10D8OF for restoring T cell functions was higher, and h10D8V4 and h10D8V5 demonstrated similar results.

TABLE 5.3

Equilibrium dissociation constant assay of h10D8OF and h10D8V2 to TIGIT-his tag antigen[a]

| Ab | ka(1/Ms) | kd(1/s) | KD(M) |
|---|---|---|---|
| h10D8OF | 5.02E+05 | 1.83E−03 | 3.63E−09 |
| h10D8V2 | 1.02E+05 | 4.80E−04 | 4.68E−10 |
| Tiragolumab | 8.18E+05 | 9.24E−05 | 1.13E−10 |

[a] Note: the TIGIT-his tag used in this table was different from the antigen batch used in Table 5.2, and thus the results are different.

TABLE 5.4

Humanized sequences

| Name | Sequence | SEQ ID NO: |
|---|---|---|
| h10D8V1 heavy chain V region | QVQLQESGGELGKPGGSLRLSCAASGFTFSSYGMSWVRQAPGKGL ELVATINSNGGSTYYPDSVKGRFTISRDNSKNTLYLQMDSLRAED TAVYYCARLGTGTLGFAYWGQGTLVTVSS | 33 |
| h10D8V1 light chain V region | DIQMTQSPSTLSAFVGDTITITCKASQDVKTAVSWYQQKPGQPPK LLIYWASTRHTGVPDRFSGSGSGTDYTLTISSLQAEDVAVYYCQQ HYSTPWTFGQGTKVDIK | 34 |
| h10D8OF heavy chain V region sequence | QVQLVESGGGVVQPGRSLRLDCKASGFTFSSYGMSWVRQAPGKGL ELVATINSNGGSTYYPDSVKGRFTISRDNSKNTLFLQMNSLRAED TAVYYCARLGTGTLGFAYWGQGTLVTVSS | 35 |

TABLE 5.4-continued

Humanized sequences

| Name | Sequence | SEQ ID NO: |
|---|---|---|
| h10D8OF light chain V region | EIVMTQSPATLSLSPGERATLSCKASQDVKTAVSWYQQKPGQAPR LLIYWASTRATGIPARFSGSGSGTDYTLTISSLEPEDFAVYYCQQ HYSTPWTFGQGTKVEIK | 36 |
| h10D8V3 heavy chain V region | EVQLVESGGGLVQPGGSLRLSCAASGFTFSSYGMSWVRQAPGKGL ELVATINSNGGSTYYPDSVKGRFTISRDNSKNTLYLQMNSLRAED TAVYYCARLGTGTLGFAYWGQGTLVTVSS | 37 |
| h10D8V3 light chain V region | DIQMTQSPSSLSASVGDRVTITCKASQDVKTAVSWYQQKPGKAPK LLIYWASTRHTGVPSRFSGSGSGTDYTLTISSLQPEDFATYYCQQ HYSTPWTFGGGTKVEIK | 38 |
| h10D8V4 heavy chain V region | QVQLQESGGGLVQPGGSLRLSCAASGFTFSSYGMSWVRQAPGKGL ELVATINSNGGSTYYPDSVKGRFTISRDNAKNTLYLQMNSLRAED TAVYYCARLGTGTLGFAYWGQGTLVTVSS | 39 |
| h10D8V4 light chain V region | DIVMTQSPSTLSASVGDRVTITCKASQDVKTAVSWYQQKPGQPPK LLIYWASTRHTGVPDRFSGSGSGTDYTLTISSLQAEDVAVYYCQQ HYSTPWTFGQGTKVEIK | 40 |
| h10D8V5 heavy chain V region | QVQLQESGGGLVQPGGSLRLSCAASGFTFSSYGMSWVRQNPDKRL ELVATINSNGGSTYYPDSVKGRFTISRDNAKNTLYLQMNSLRAED TAMYYCARLGTGTLGFAYWGQGTLVTVSS | 41 |
| h10D8V5 light chain V region | DIVMTQSPKTLSASVGDRVTITCKASQDVKTAVSWYQQKPGQSPK LLIYWASTRHTGVPDRFSGSGSGTDYTLTISSLQAEDVALYYCQQ HYSTPWTFGGGTKVEIK | 42 |
| h10D8OF heavy chain | QVQLVESGGGVVQPGRSLRLDCKASGFTFSSYGMSWVRQAPGKGL ELVATINSNGGSTYYPDSVKGRFTISRDNSKNTLFLQMNSLRAED TAVYYCARLGTGTLGFAYWGQGTLVTVSSASTKGPSVFPLAPSSK STSGGTAALGCLVKDYFPEPVTVSWNSGALTSGVHTFPAVLQSSG LYSLSSVVTVPSSSLGTQTYICNVNHKPSNTKVDKKVEPKSCDKT HTCPPCPAPELLGGPSVFLFPPKPKDTLMISRTPEVTCVVVDVSH EDPEVKFNWYVDGVEVHNAKTKPREEQYNSTYRVVSVLTVLHQDW LNGKEYKCKVSNKALPAPIEKTISKAKGQPREPQVYTLPPSRDEL TKNQVSLTCLVKGFYPSDIAVEWESNGQPENNYKTTPPVLDSDGS FFLYSKLTVDKSRWQQGNVFSCSVMHEALHNHYTQKSLSLSPGK | 44 |
| h10D8OF light chain | EIVMTQSPATLSLSPGERATLSCKASQDVKTAVSWYQQKPGQAPR LLIYWASTRATGIPARFSGSGSGTDYTLTISSLEPEDFAVYYCQQ HYSTPWTFGQGTKVEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSFNRGEC | 45 |

Figure 15:
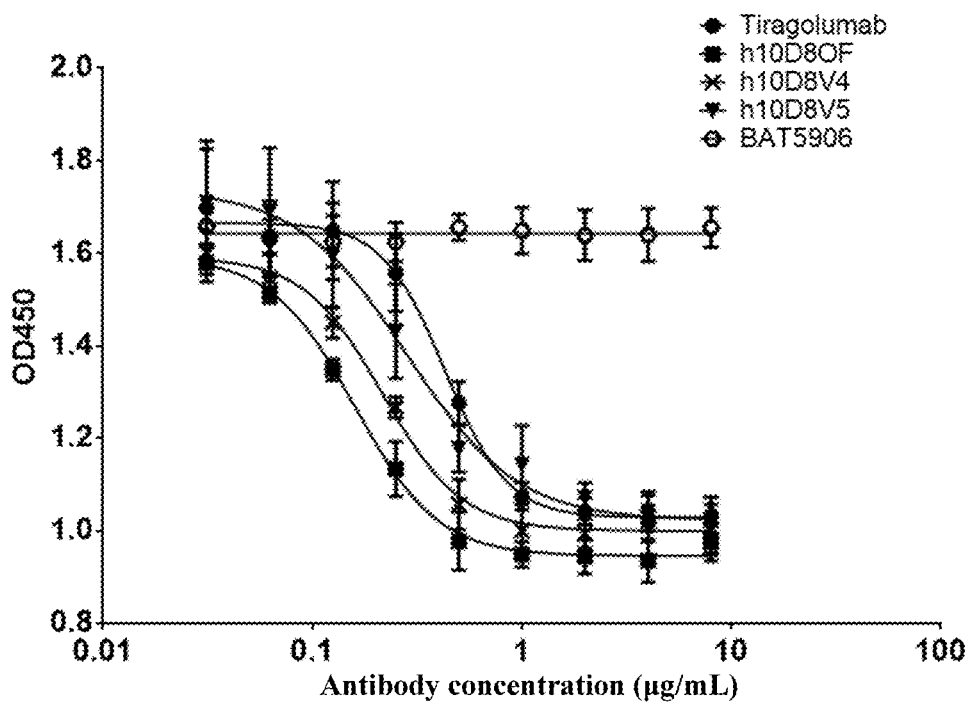
FIG. 15: Assay of h10D8OF, h10D8V4 and h10D8V5 for blocking the binding of TIGIT to PVR. denotes Tiragolumab, denotes h10D8OF, denotes h10D8V4, denotes h10D8V5, and denotes an irrelevant control BAT5906.

Example 6. Assay of Humanized Antibodies for Blocking the Binding of TIGIT to PVR Some functions of the murine antibody, such as blocking the binding of TIGIT to PVR, may theoretically be retained after humanization. The blocking assay for the binding of TIGIT and PVR by humanized antibody is similar to the method in Example 3. The abilities of h10D8OF, h10D8V4, h10D8V5, Tiragolumab (positive control antibody) and irrelevant antibody (isotype control) BAT5906 to block the binding of TIGIT to PVR in the same conditions were tested by ELISA. The experimental results (FIG. 15) showed that h10D8OF, h10D8V4, h10D8V5, and Tiragolumab were all effective in blocking the binding of TIGIT to PVR, and the $IC_{50}$ half maximal inhibitory concentration) values were 0.1592 μg/mL, 0.2166 μg/mL, 0.2837 μg/mL and 0.4289 μg/mL, respectively. It can be seen from the $IC_{50}$ and the upper and lower plateau values of the 4-parameter curve that, the h10D8OF and h10D8V4 have a stronger ability to block the binding of TIGIT to PVR than that of the positive control antibody Tiragolumab.

Figure 16:
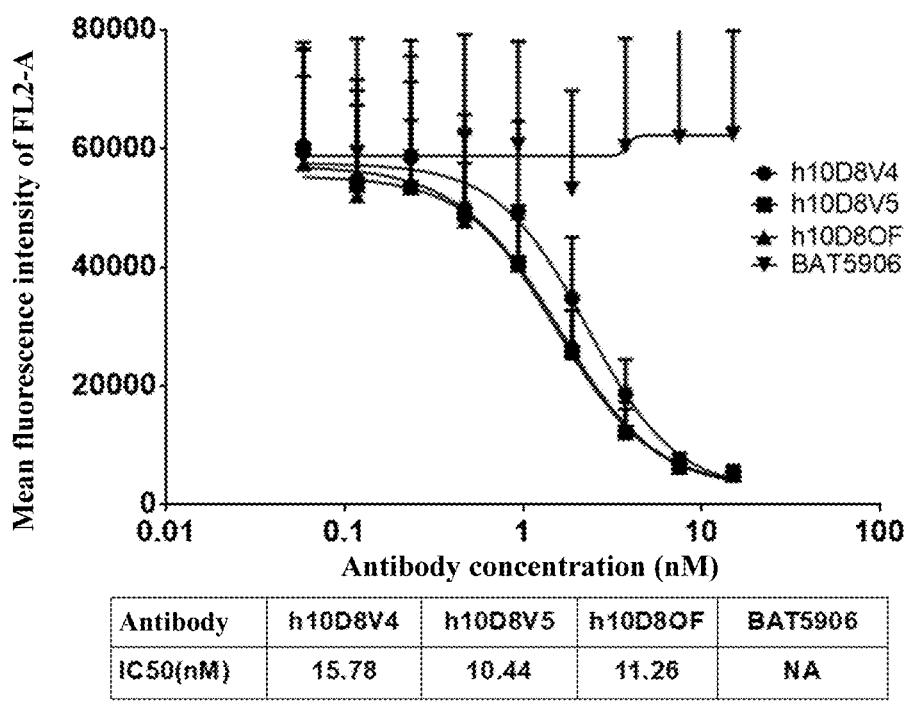
FIG. 16: Comparison of abilities of h10D8OF, h10D8V4, and h10D8V5 to block the binding of TIGIT on Jurkat cell membrane to PVR. denotes h10D8V4, denotes h10D8V5, denotes h10D8OF, and denotes an irrelevant control BAT5906.
Figure 17:
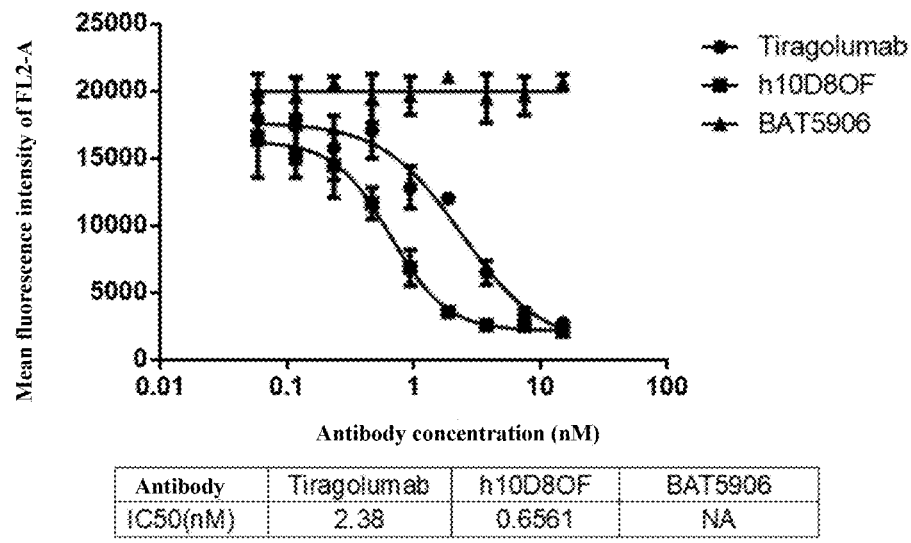
FIG. 17: Comparison of abilities of h10D8OF and Tiragolumab to block the binding of TIGIT on Jurkat cell membrane to PVR. denotes Tiragolumab, denotes h10D8OF, and denotes an irrelevant control BAT5906.

Such antibodies were also re-validated for blocking the binding of biotinylated PVR to TIGIT on Jurkat cell surface using Jurkat cells overexpressing human TIGIT (Jurkat-hTIGIT 2E6). The reaction system was prepared as follows: an 80 nM solution of biotinylated PVR-Fc protein in PBS was prepared as an antibody diluent to dilute the antibody. The antibody was serially two-fold diluted from 15 nM to the $10^{th}$ concentration (including 0 nM). The 10 concentration gradients of antibody were separately transferred into 10 centrifuge tubes each containing $1 \times 10^6$ Jurkat-hTIGIT cells. The cells were then resuspended, and the mixture was incubated at 4° C. for 1 hour. The cells were centrifuged. The supernatant was discarded and the cells were washed twice with PBS. The cells were resuspended in 100 μL of 1:2000 diluted streptavidin PE (Thermo, Cat. No.: 12-4317-87) and incubated at 4° C. for 40 minutes. The cells were centrifuged, and the supernatant was discarded. The cells were washed twice with PBS, resuspended in 200 μL of PBS, and were detected for fluorescent signal using a flow analyzer (mean FL2-A). Finally, the collected fluorescent signals were plotted by 4-parameter fitting for analysis, and the $IC_{50}$ was calculated. The $IC_{50}$ of h10D8OF, h10D8V4 and h10D8V5 (as shown in FIG. 16) was 11.26 nM, 15.78 nM and 10.44 nM. The 3 antibodies can effectively block the binding of biotinylated PVR-FC to TIGIT on the cell membrane surface of Jurkat-hTIGIT, and h10D8OF and h10D8V5 demonstrate better blocking effects. Meanwhile, the abilities of h10D8OF and the positive control antibody Tiragolumab to block the binding of PVR to TIGIT were compared (as shown in FIGS. 17), and h10D8OF showed a stronger blocking effect.

Example 7. ADCC Activity Assay of Humanized Antibody

Figure 18:
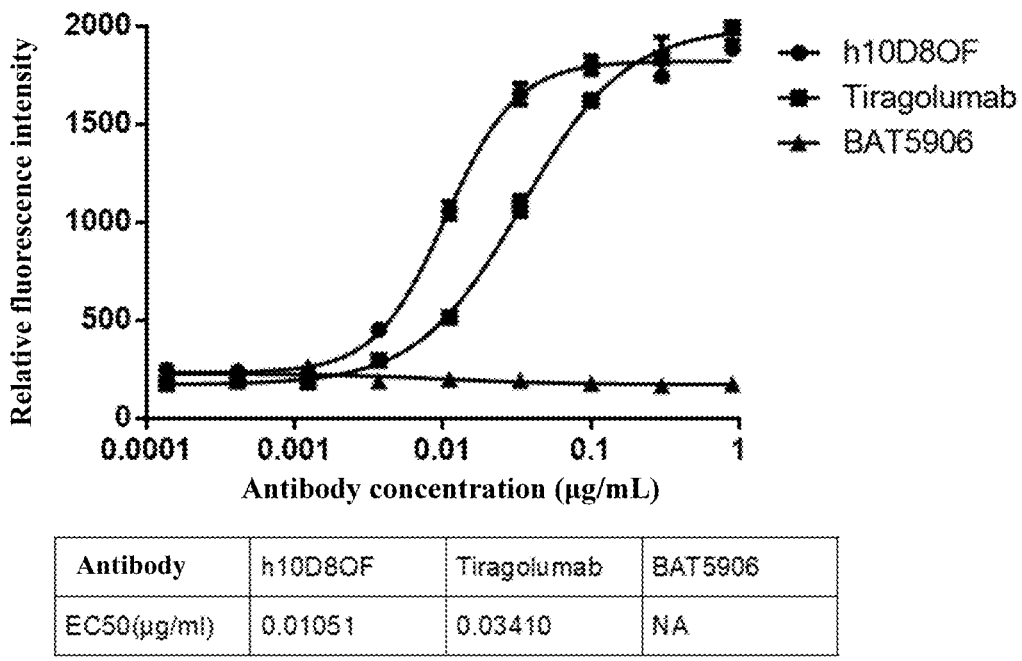
FIG. 18: ADCC activity assay of h10D8OF. denotes h10D8OF, denotes Tiragolumab, and denotes an irrelevant control BAT5906.

NFAT and luciferase reporter gene elements and the FcγRIIIa (CD16) receptor gene were transfected in Jurkat cells (ATCC, Clone E6-1, Cat. No.: TIB-152™). As such, a stable cell line steadily expressing the FcγRIIIa receptor was successfully constructed, which is an essential molecule for mediating ADCC biological activity. By connecting effector cells to target cells, a monoclonal antibody can activate the NFAT pathway and initiate luciferase reporter gene expression. Jurkat cells (ATCC, Clone E6-1) were transfected with human TIGIT gene to overexpress the human TIGIT molecule, and this stable cell line was the target cell. The procedures for detecting the ADCC activity of the antibody are as follows: 1) An appropriate amount of cells were taken according to cell density and centrifuged at 1200 rpm for 5 min to remove the growth medium, and the cell density was adjusted. 2) The 2 cells were mixed well and transferred to a cell culture plate (Corning, Cat. No.: 3917). The number of effector cells per well was $8\times10^4$, the number of target cells per well was $2\times10^4$, and the total volume of the mixture per well was 50 μL. 3) The antibody was diluted with a 1640 medium containing 1% of FBS. h10D8OF, Tiragolumab and irrelevant antibody (without ADCC activity) were serially 3-fold diluted from 1.8 μg/mL (50 μL per well, with a final concentration of 0.9 μg/mL) in triplicate to a final concentration gradient of 0 μg/mL. 4) After the antibodies were added, the mixtures were well mixed. The cells were then incubated in a 37° C./8% $CO_2$ incubator for 4 hours. 5) After the incubation the cells were let stand at room temperature for 10 min, and the luciferase substrate reagent was also equilibrated to room temperature in advance. The substrate solution was added at 100 μL/well and after 10 min the detection was started. The results are shown in FIG. 18, where both h10D8OF and Tiragolumab have ADCC activity, and h10D8OF shows a slightly higher ADCC activity than that of Tiragolumab in the same conditions.

Figure 19:
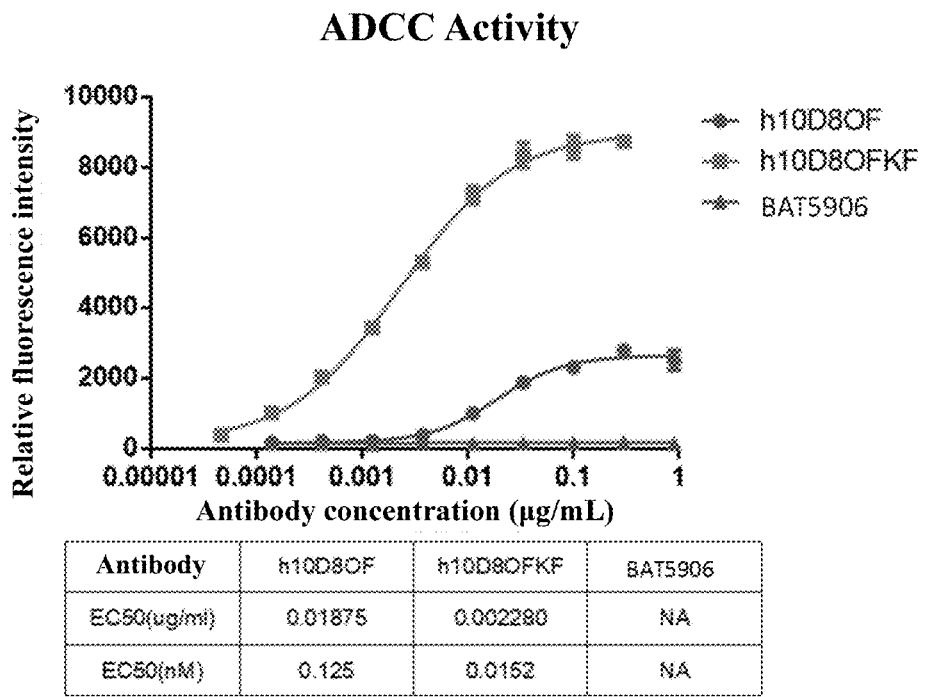
FIG. 19: Comparison of ADCC activities of h10D8OF and h10D8OFKF.

In another experiment, host CHO cells secreting h10D8OF were engineered (see Patent Nos. CN107881160A and WO2019029713A1 for the engineering method) to remove the fucose in the h10D8OF antibody. The resulting antibody was coded h10D8OFKF. The ADCC activities of h10D8OFKF and h10D8OF were compared using a method similar to that described above. As shown in FIG. 19, both h10D8OFKF and h10D8OF have ADCC activity, and the $EC_{50}$ was 0.0152 nM and 0.125 nM, respectively. h10D8OFKF showed an ADCC activity 8.8 times that of h10D8OF in the same condition, which indicates a possibly better in vivo efficacy.

Example 8. Cytokine Release Assay in the Effect of Humanized Anti-TIGIT Antibodies The binding of TIGIT to PVR (CD155) expressed on the surface of a tumor cell or APC down-regulates the effector function of T cells and suppresses the anti-tumor immune response. The ability of anti-TIGIT antibodies to block PVR-mediated inhibition of T cell cytokine release was examined Commercially available primary human CD3+ cells (Leide Biosciences Co., Ltd., Cat. No.: 1507) were subjected to an induction culture in a 1640 medium containing PHA (2 μg/mL), IL-2 (4 ng/mL) and PBS (10%) for 10 days. After that the cells were centrifuged and resuspended in a medium free of PHA and IL-2, and then incubated in a 5% $CO_2$/37° C. incubator for 24 hours of static culture. The cells were then resuspended at a density of $5\times10^5$ cells/mL and co-incubated with the irrelevant antibody BAT5906 (see Chinese Patent Application No. CN110003328A), h10D8OF (25 μg/mL or 10 μg/mL) or Tiragolumab (25 μg/mL or 10 μg/mL) for 30 min at room temperature. After the incubation was completed, the cells were inoculated into cell culture plates pre-coated with anti-CD3 antibody (10 μg/mL) (BD Biosciences, Cat. No. 555336), PVR-Fc (10 μg/mL), or anti-CD3 antibody (10 μg/mL)+PVR-Fc (10 μg/mL), and incubated in an incubator (37° C., 5% $CO_2$) for 48 hours. Finally, the cells in the cell culture plate were collected and centrifuged. The supernatant was diluted in a certain factor, and was detected for the release of the cytokines IFN-γ and IL-2 in the cell supernatant.

Figure 20:
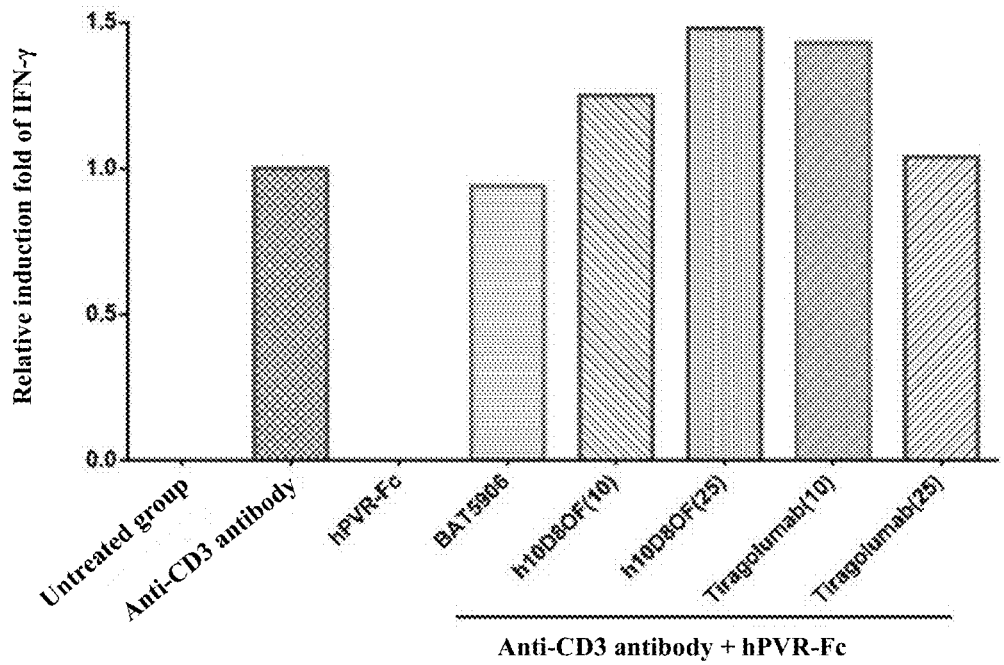
FIG. 20: IFN-γ relative induction fold. 10 denotes 10 μg/mL, and 25 denotes 25 μg/mL.
Figure 21:
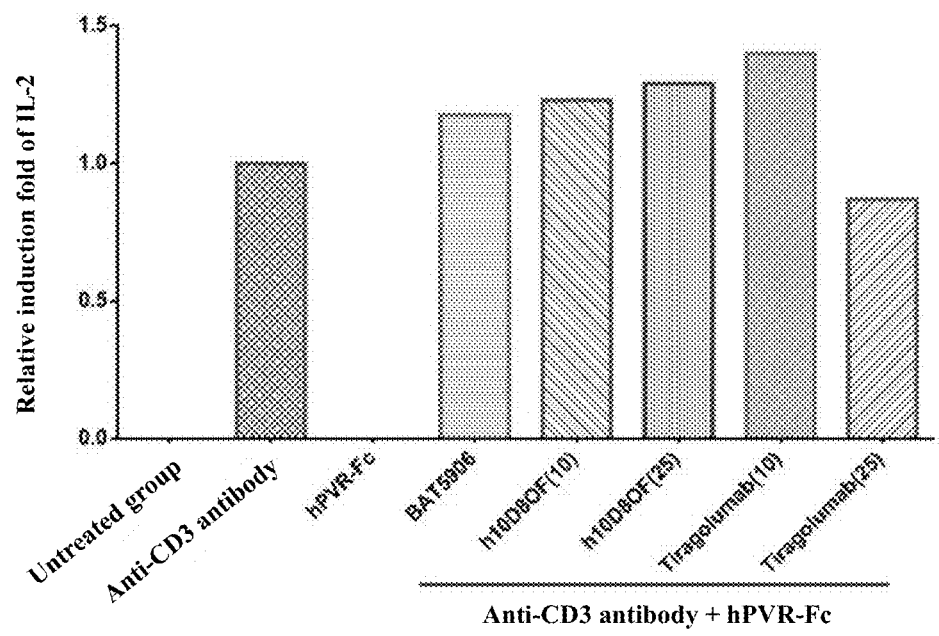
FIG. 21: IL-2 relative induction fold. 10 denotes 10 μg/mL, and 25 denotes 25 μg/mL.

The cytokine produced in lymphocytes induced by other treatments was normalized by that induced by the anti-CD3 antibody alone, as shown in FIGS. 20 and 21. The results showed that, h10D8OF induced lymphocytes to produce more IFN-γ and IL-2 in a concentration-dependent manner.

Example 9. Validation of Ability of Anti-TIGIT Antibodies to Inhibit Tumor Growth in Mouse B-hPD-1/hTIGIT Double Humanized MC38 Tumor Graft Model Since the humanized antibody does not recognize mouse TIGIT, the extracellular regions of PD-1 and TIGIT molecules in the mouse genome with the C57BL/6 background were humanized and transformed into human PD-1 and human TIGIT, i.e., B-hPD-1/hTIGIT double humanized mouse. The mouse was C57BL/6-Pdcd1 tm1 (hPDCD1) Tigit tm1 (hTIGIT)/Bgen (Biocytogen Pharmaceuticals Co., Ltd.). In homozygous B-hPD-1/hTIGIT mouse splenocytes, hTIGIT and hPD-1 mRNA expressions can be detected, and no mTIGIT or mPD-1 mRNA expression is detected (data from official website of Biocytogen Pharmaceuticals Co., Ltd.). The MC38 colon cancer animal model was established by using the B-hPD-1/hTIGIT humanized mice to validate the efficacies of the anti-TIGIT antibody and the combination of the anti-TIGIT antibody and an anti-PD-1 antibody.

Figure 22:
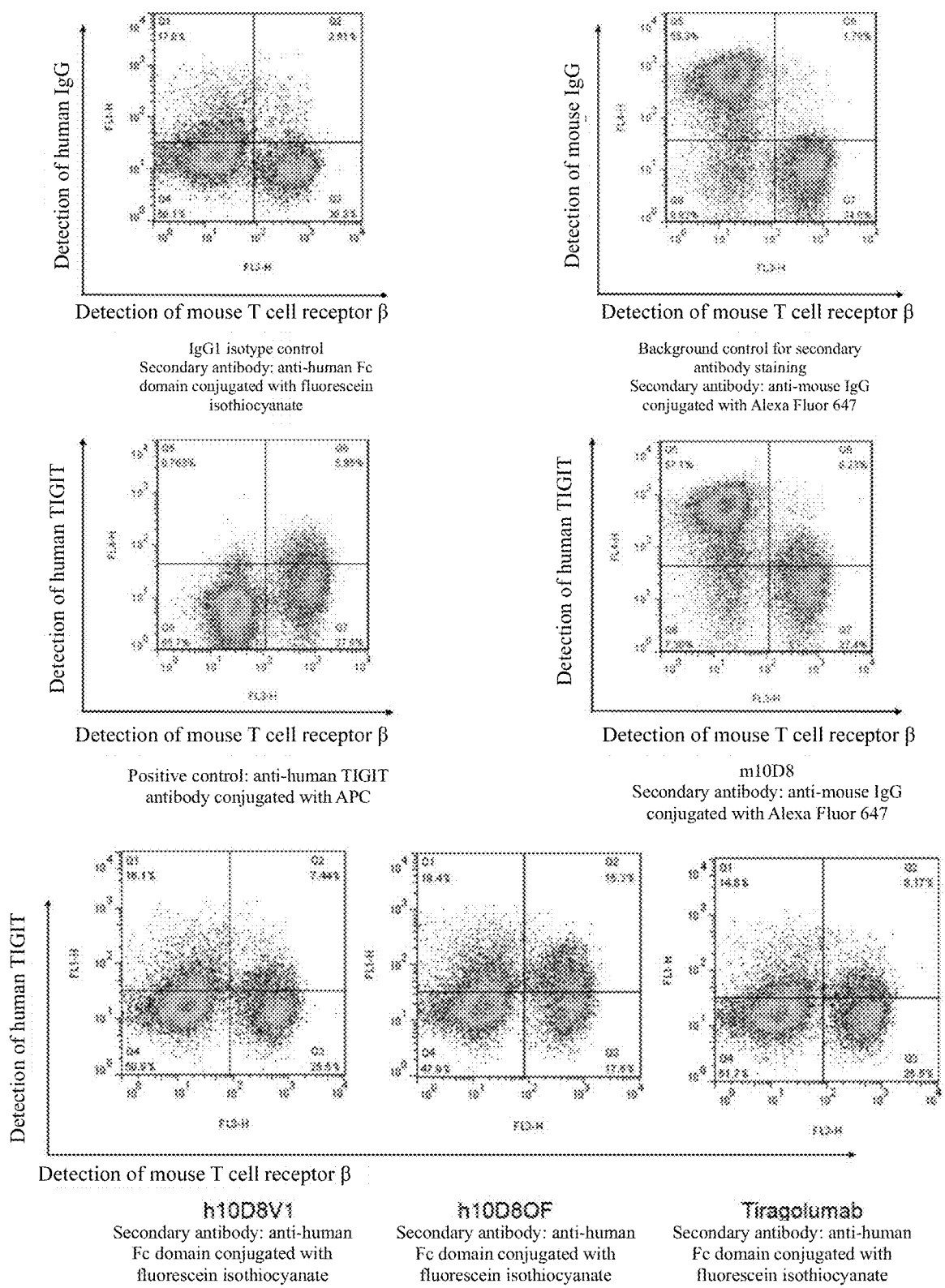
FIG. 22: Binding assay of anti-TIGIT antibodies to hTIGIT on the surface of a B-hPD-1/hTIGIT double humanized mouse T cell. The secondary antibody for the humanized antibody was an anti-human Fc, FITC; the secondary antibody of the murine antibody was an anti-mouse IgG, Alexa Fluor 647.
Figure 23:
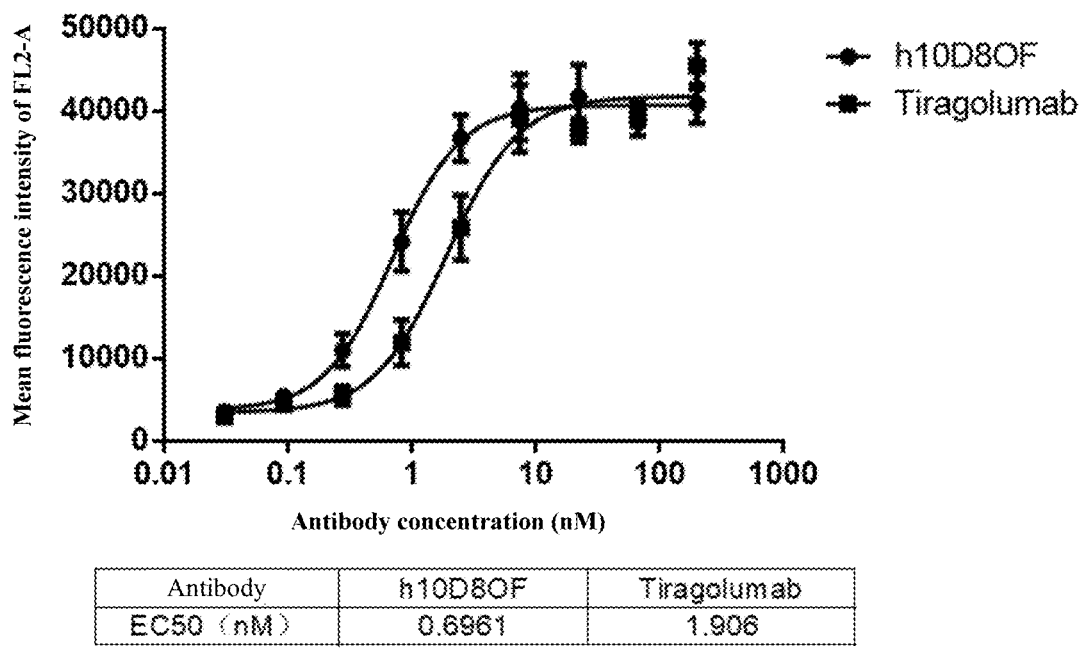
FIG. 23: Comparison of binding capacities of h10D8OF and Tiragolumab to TIGIT on the surface of a Jurkat-hTIGIT cell. denotes h10D8OF, and denotes Tiragolumab.

Before animal pharmacodynamic study, a preliminary study was conducted to validate that the anti-TIGIT antibody can effectively bind to hTIGIT on cell surface in the B-hPD-1/hTIGIT double-humanized mice. 11.5 μg of anti-mCD3e antibody (Biolegend, Cat. No.: 100301) was dissolved in 300 μL of PBS. A B-hPD-1/hTIGIT double-humanized mouse was injected intraperitoneally with 200 μL of anti-mCD3e antibody solution. After 24 h, the mouse was sacrificed, and the spleen was collected and transferred to a 15-mL centrifuge tube containing 5 mL of PBS. After centrifugation, the spleen was then transferred to a 6-well plate and placed on a 70-μm mesh screen. 1 mL of PBS was added. The spleen was ground with a sterile syringe tail. The mesh screen was then rinsed with 1-2 mL of PBS. The filtered cell suspension was centrifuged at 3000 rpm for 5 min, and the supernatant was discarded. The cells were subjected to a transient centrifugation and the supernatant was discarded. 1 mL of red blood cell lysis buffer (Beyotime, Cat. No.: C3702) was added to each spleen and the cells were lysed on ice for 5 min. Finally, 5 mL of PBS was added. The cells were mixed well and centrifuged at 3000 rpm at 4° C. for 3 min. The supernatant was discarded, and the cells were subjected to a transient centrifugation and the supernatant was discarded. For the subsequent flow cytometry, the cells were suspended in 300 μL of PBS and mixed with 6 μL of anti-mCD16/32 antibody (Biolegend, Cat. No.: 101310) and Human TruStrain FcX (Biolegend, Cat. No.: 422302) and incubated on ice for 15 min. 1.2 mL of PBS was added to mix the cells well and the cell density was adjusted to $4 \times 10^7$ cells/mL. 25 μL of cell suspension was added to tubes to be stained, and the corresponding antibodies PerCP-anti-mTcRβ (Biolegend, Cat. No.: 109228) and APC-anti-hTIGIT antibody (eBioscience, Cat. No.: 17-9500-42), mouse anti-TIGIT antibody secondary antibody anti-mouse IgG/Alexa Fluor 647 (goat anti-mouse IgG/Alexa Fluor 647; Beijing Bioss Biotech Co., Ltd., Cat. No.: bs-0296G-AF647), and humanized anti-TIGIT antibody secondary antibody anti-human Fc, FITC (goat anti-human IgG Fc secondary antibody, FITC; Invitrogen, Cat. No.: 18818) were added for assay. The experiment design is shown in Table 9.1. The flow cytometry results showed (as shown in FIG. 22) that m10D8, h10D8V1, h10D8OF and Tiragolumab can effectively bind to hTIGIT on the surface of T cells of B-hPD-1/hTIGIT double-humanized mice, wherein the binding capacity of h10D8OF to hTIGIT is stronger than those of the other antibodies in the same conditions. Similar events were also observed in binding assay of h10D8OF and Tiragolumab to Jurkat-hTIGIT 2E6 on Jurkat cells overexpressing human TIGIT (see FIG. 23), possibly indicating that h10D8OF ($EC_{50}$ was 0.6961 nM) had a stronger affinity for TIGIT in physiological or near physiological conditions than Tiragolumab ($EC_{50}$ was 1.906 nM).

Figure 24:
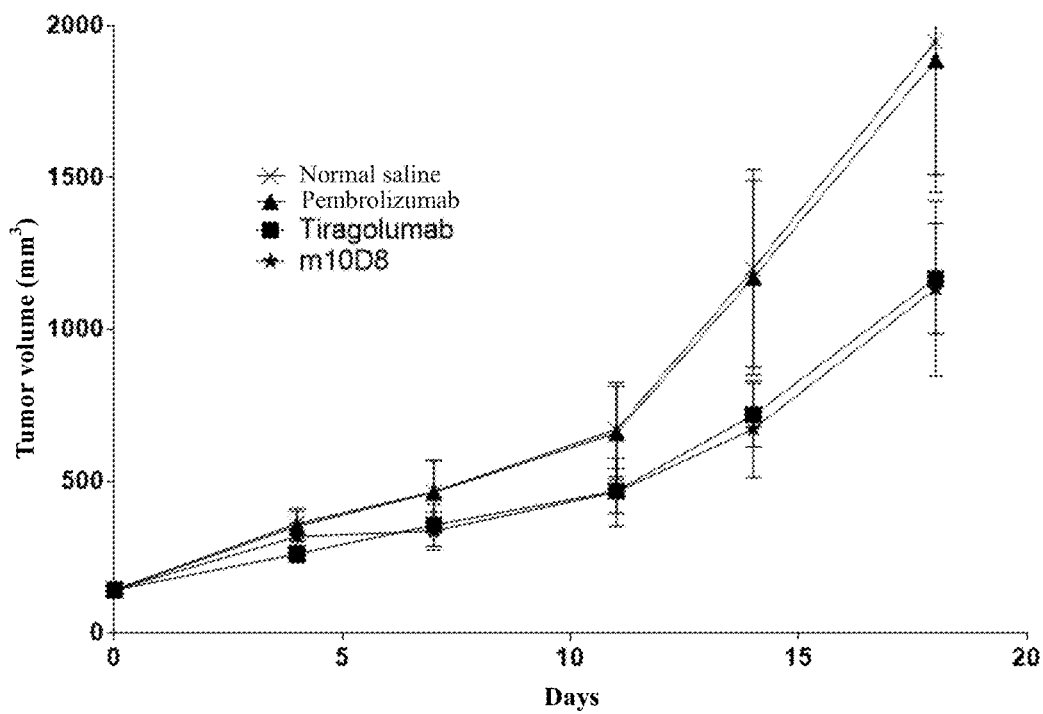
FIG. 24: Efficacy of murine antibody monotherapies. denotes normal saline (vehicle), denotes Pembrolizumab monotherapy (0.1 mg/kg), denotes Tiragolumab monotherapy (20 mg/kg), and denotes m10D8.
Figure 25:
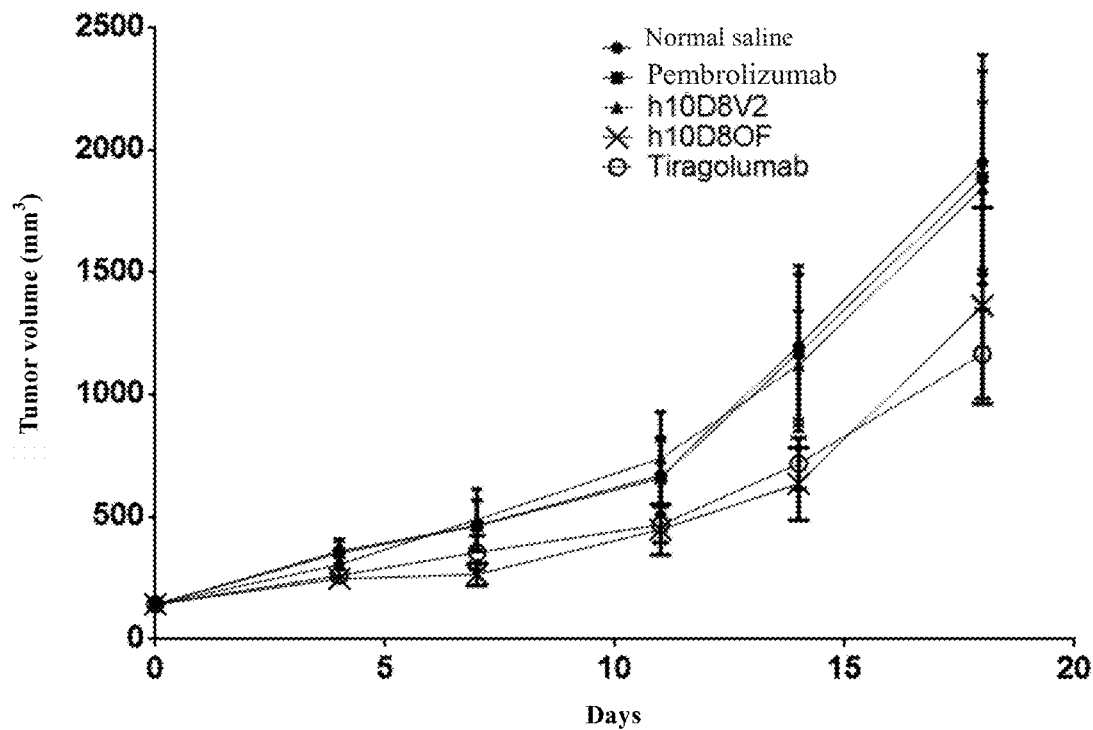
FIG. 25: Efficacy of humanized antibody combination therapies. denotes normal saline, denotes Pembrolizumab monotherapy (0.1 mg/kg), denotes h10D8V2 monotherapy (20 mg/kg), denotes Tiragolumab monotherapy (20 mg/kg), and denotes h10D8OF monotherapy (20 mg/kg).
Figure 26:
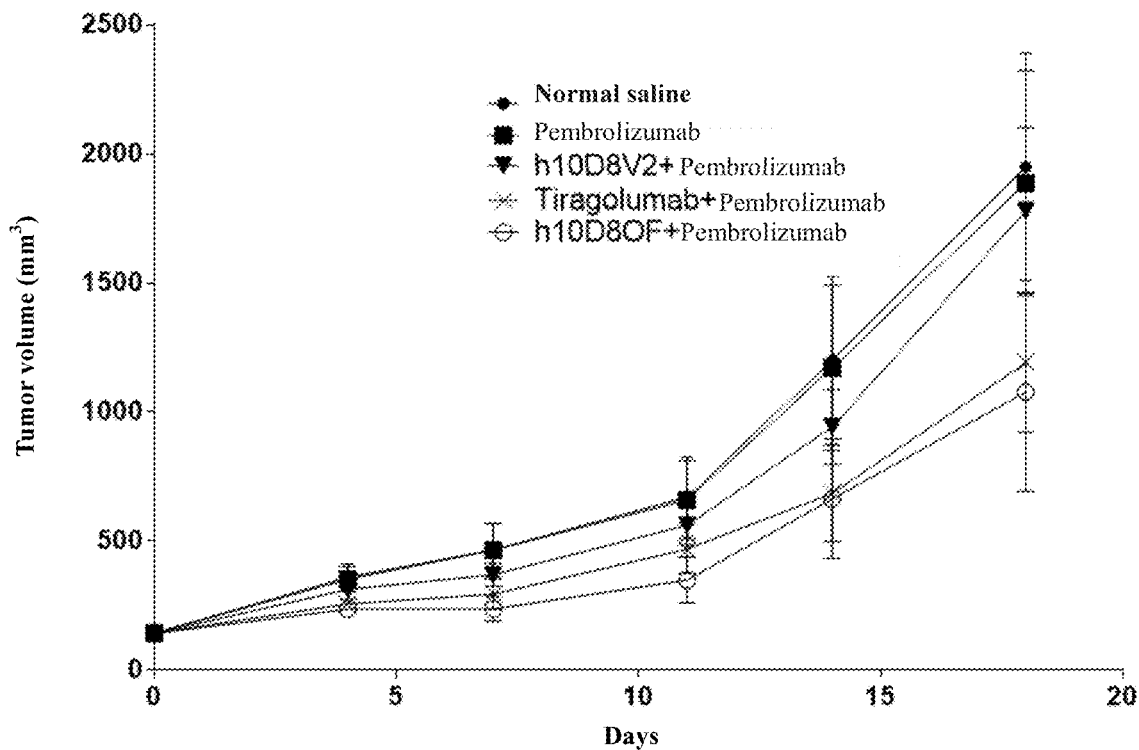
FIG. 26: Efficacy of humanized antibody combination therapies. denotes normal saline, denotes Pembrolizumab, denotes the combination therapy of h10D8V2 (20 mg/kg) and Pembrolizumab (0.1 mg/kg), denotes the combination therapy of Tiragolumab (20 mg/kg) and Pembrolizumab (0.1 mg/kg), and denotes the combination therapy of h10D8OF (20 mg/kg) and Pembrolizumab (0.1 mg/kg).

Female mice aged 6-8 weeks were selected and divided into groups of n=6. MC38 cells were inoculated at right axilla of the mice (Biocytogen Jiangsu Co., Ltd.) at $5 \times 10^5$/0.1 mL/mouse, and the mice were grouped and treated when the tumor volume reached $150 \pm 50$ mm$^3$ while those with large or small tumor volume were excluded. The treatment was given once every 3 days, and the tumor volume was measured twice weekly. The dose of Pembrolizumab for each administration was 0.1 mg/kg, and the doses of Tiragolumab and m10D8 were 20 mg/kg. The efficacy results of the anti-TIGIT antibody monotherapies (see FIG. 24) showed that both Tiragolumab and m10D8 can inhibit tumor growth, and the monotherapy efficacies for m10D8 and Tiragolumab are close. The efficacy results of the humanized anti-TIGIT antibody monotherapies (see FIG. 25) showed that the h10D8V2 has a poor tumor inhibitory effect, and the tumor inhibitory effects of h10D8OF and Tiragolumab are close. The efficacy results of the anti-TIGIT antibody/Pembrolizumab combination therapies (see FIG. 26) showed that the combination of h10D8V2 and Pembrolizumab has a poor tumor inhibitory effect, and the tumor inhibitory effects of h10D8OF/Pembrolizumab and Tiragolumab/Pembrolizumab combinations are close. Generally, in terms of animal pharmacodynamics, the murine antibodies and the humanized antibodies have the effect of inhibiting tumor proliferation and have the potential for use in combination with Pembrolizumab.

TABLE 9.1

Binding assay of anti-TIGIT antibodies to hTIGIT on the surface of a B-hPD-1/hTIGIT double humanized mouse T cell

| Sample number | Detection | Volume of primary antibody | Staining | Volume of liquid | Cell | CD3 stimulation | Mouse |
|---|---|---|---|---|---|---|---|
| Anti-human Fc conjugation FITC | mTcRβ + hIgG | 0.5 μL | PerCP + FITC | 50 μL | | | B-hPD-1/hTIGIT |
| Anti-TIGIT[a] | mTcRβ + hTIGIT | 0.5 μL + 1 μL | PerCP + APC | 50 μL | | | B-hPD-1/hTIGIT |
| Anti-mouse IgG Af647 | mTcRβ + mIgG | 0.5 μL | PerCP + AF647 | 50 μL | | | B-hPD-1/hTIGIT |
| m10D8 | mTcRβ + m10D8 + mIgG | 0.5 μL | PerCP + AF647 | 50 μL | Spleen cells | 7.5 μg, stimulation for 24 h | B-hPD-1/hTIGIT |
| h10D8V1 | mTcRβ + h10D8V1 + hIgG | 0.5 μL | PerCP + FITC | 50 μL | | | B-hPD-1/hTIGIT |
| h10D8OF | mTcRβ + h10D8OF + hIgG | 0.5 μL | PerCP + FITC | 50 μL | | | B-hPD-1/hTIGIT |
| Tiragolumab | mTcRβ + Tiragolumab + hIgG | 0.5 μL | PerCP + FITC | 50 μL | | | B-hPD-1/hTIGIT |

[a]denotes reagent antibody (eBioscience, Cat. No.: 7-9500-42)

Example 10. Effect of Humanized Anti-TIGIT Antibodies on Lymphocyte Subpopulations The effect of anti-TIGIT antibodies on CD4+ T cells and CD8+ T cells in mouse MC38 tumor infiltrating lymphocytes (TILs) was analyzed at the therapeutic endpoint in the in vivo pharmacodynamic study. The vehicle control group (normal saline for injection; n=4) and h10D8OF monotherapy group (20 mg/kg; n=5) were selected. Fresh tumor tissues were surgically excised from the mice, washed with PBS and kept on ice. The tissues were repeatedly cut by ophthalmic scissors, and ground in an IKA grinder in 10-s forward/reverse cycles at 1200 rpm for 2 min. The ground tumor tissue solution was filtered through a 70-μm screen into a 50-mL centrifuge tube, washed once and centrifuged for 5 min at 2000 rpm in a low-temperature centrifuge at 4°

C. The supernatant was discarded, and the tumor cells were resuspended by using a proper amount of PBS.

The dead/viable cells were stained first. 2 μL of Zombie NIR™ dye (Biolegend, Cat. No.: 423106) was added to 500 μL of PBS to prepare a 2× dead/viable cell staining solution. 25 μL of tumor cell suspension was added into the wells of a 96-well plate, and 25 μL of the 2× dead/viable cell staining solution was added into the corresponding wells containing the tumor cell suspension. The plate was incubated for 15 min in the dark at room temperature by gentle shaking. The cell surface staining was then performed, and the stained cells in the above step were transferred to another 96-well plate by a pipette in an amount of 25 μL. 25 μL of cell surface marker staining solution was added to each well, followed by an incubation at 4° C. for 30 min in the dark. The cell surface marker staining solution contained: an anti-CD45 antibody (FITC, 0.5 μL, Biolegend, Cat. No. 231092), an anti-mCD4 antibody (PE, 0.5 μL, Biolegend, Cat. No. 248731), an anti-mCD8 antibody (BV510, 0.5 μL, Biolegend, Cat. No. 248151), and an anti-hTIGIT antibody (APC, 1 μL, Biolegend, Cat. No. 4272773). After the incubation, 185 μL of PBS was added to resuspend the cells. After mixing, the mixture was centrifuged for 5 min at 2000 rpm and 4° C. The supernatant was discarded, and the residue was further dried by absorbent paper. Then 200 μL of fixing solution (1×) was added to each well to resuspend the cells, and after mixing, the mixture was let stand overnight at 4° C. After fixation, the cells were centrifuged at 3000 rpm for 5 min. The supernatant was discarded, and the residue was further dried by absorbent paper. 200 μL of membrane-penetrating solution was added to each well, and the cells were centrifuged at 3000 rpm for 5 min. The supernatant was discarded, and the residue was further dried by absorbent paper. 25 μL of the membrane-penetrating solution was added to each well to resuspend the cells, and 25 μL of prepared intracellular dye (Anti-Mouse/Rat Foxp3, APC) was added. The mixture was incubated at 4° C. for 30 min in the dark. 200 μL of 1× membrane-penetrating solution was added to each well. After mixing, the cells were centrifuged at 3000 rpm and 4° C. for 5 min. The supernatant was discarded, and the residue was further dried by absorbent paper. The cells were resuspended in 250 μL of PBS and tested according to the SOP for Attune NXT flow cytometer analysis.

Figure 27:
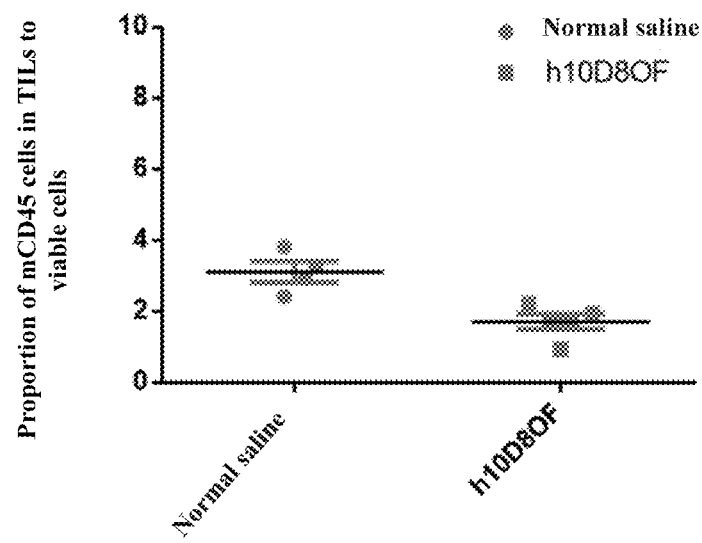
FIG. 27: Proportion of viable mCD45 cells in MC38 tumor-infiltrating lymphocytes. denotes normal saline, and denotes h10D8OF.
Figure 28:
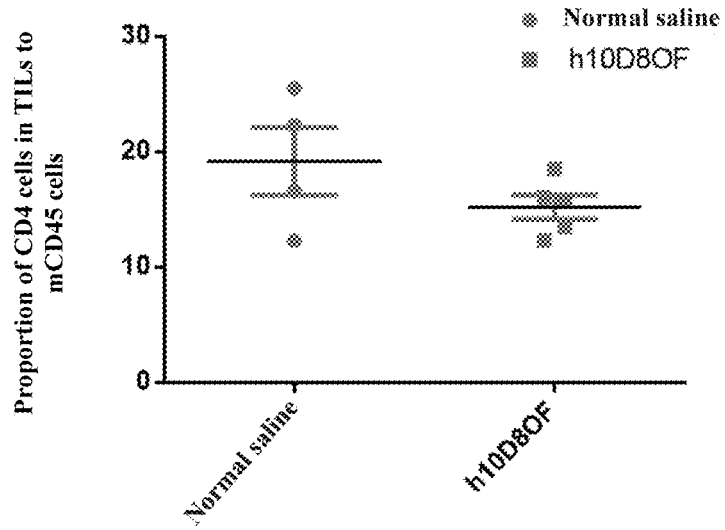
FIG. 28: Proportion of CD4+ T cells in viable mCD45 cells. denotes normal saline, and denotes h10D8OF.
Figure 29:
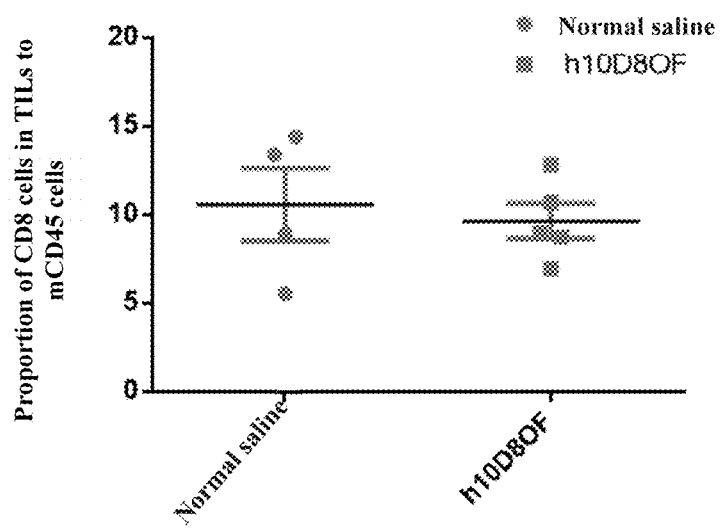
FIG. 29: Proportion of CD8+ T cells in viable mCD45 cells. denotes normal saline, and denotes h10D8OF.
Figure 30:
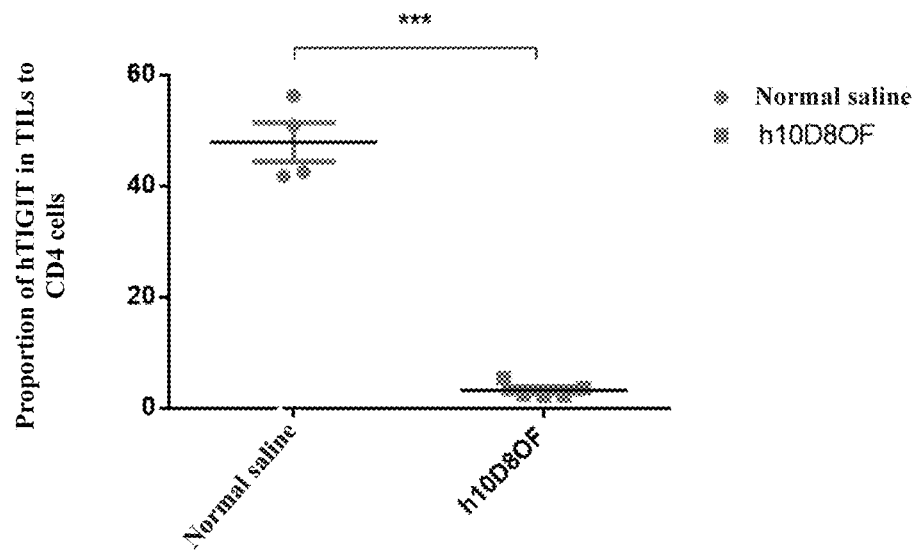
FIG. 30: Proportion of TIGIT+/CD4+ T cells in viable CD4+ T cells. denotes normal saline, and denotes h10D8OF.
Figure 31:
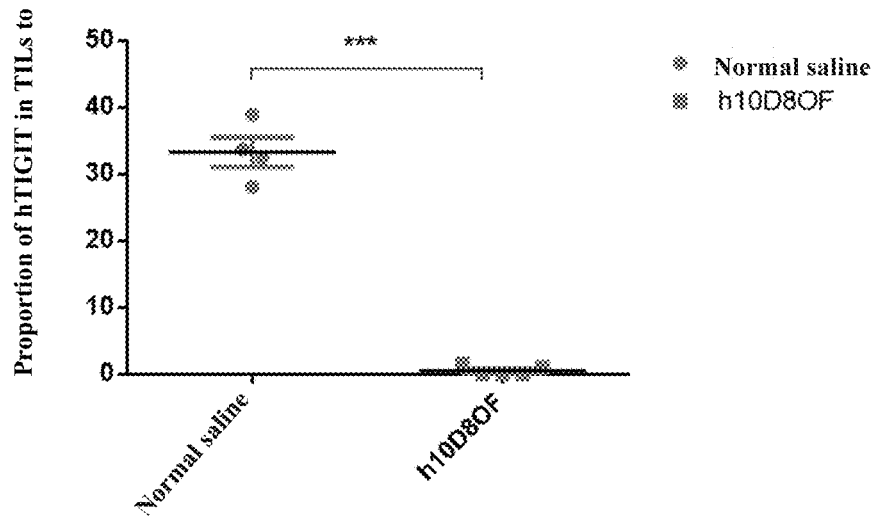
FIG. 31: Proportion of TIGIT+/CD8+ T cells in viable CD8+ T cells. denotes normal saline, and denotes h10D8OF.

The mCD45+ white blood cells were first sorted out of the prepared single cells (see FIG. 27), and CD4+ T (see FIG. 28) and CD8+ T (see FIG. 29) cells in the mCD45+ cells were then analyzed. The results indicated that there was no significant difference in mCD45+ lymphocytes in TILs of two groups, and further analysis also revealed that there was no significant difference in CD4+ T and CD8+ T cells. Further analysis of TIGIT+CD4+ T cells and TIGIT+CD8+ T cells (see FIGS. 30 and 31) found that the proportions of TIGIT+CD4+ T cells and TIGIT+CD8+ T cells were significantly decreased in the monotherapy groups relative to the control group. The results indicated that under the action of anti-TIGIT antibodies, the expression of TIGIT molecules in CD4+ and CD8+ T cells of mouse colon cancer MC38 tumor TILs is likely down-regulated, and further indirectly indicated that the function of CD8+ T cells is restored.

Example 11. Validation of Ability of Humanized Anti-TIGIT Antibodies to Inhibit Tumor Growth in B-hTIGIT Humanized Mice and hPD-L1 MC38 Tumor Graft Model Since the humanized anti-TIGIT antibody does not recognize mouse TIGIT, the extracellular region of TIGIT molecule in the mouse genome with the C57BL/6 background was humanized and transformed into human TIGIT, i.e., B-hTIGIT humanized mouse. The mouse was C57BL/6-Tigit$^{tm1(hTIGIT)}$/Begen (Biocytogen Pharmaceuticals Co., Ltd.). In homozygous B-hTIGIT mouse splenocytes, hTIGIT mRNA expression can be detected, and no mTIGIT mRNA expression is detected (data from official website of Biocytogen Pharmaceuticals Co., Ltd.). The study validated the ability of humanized anti-TIGIT antibodies to inhibit tumor growth and the potential synergistic effect of the anti-TIGIT antibody/anti-PD-L1 antibody combination in B-hTIGIT humanized mice and hPD-L1-overexpressing MC38 tumor graft model.

In order to allow h10D8OF and Tiragolumab to exert the most efficient ADCC function in mice, the heavy chain constant regions of h10D8OF and Tiragolumab were replaced with the heavy chain constant region of an mouse antibody IgG2a (SEQ ID NO: 31), and the light chain constant regions of h10D8OF and Tiragolumab were replaced with the light chain constant region of the mouse antibody IgG2a (SEQ ID NO: 32). The recombinant antibodies were named mh10D8OF and mTiragilumab.

Figure 32:
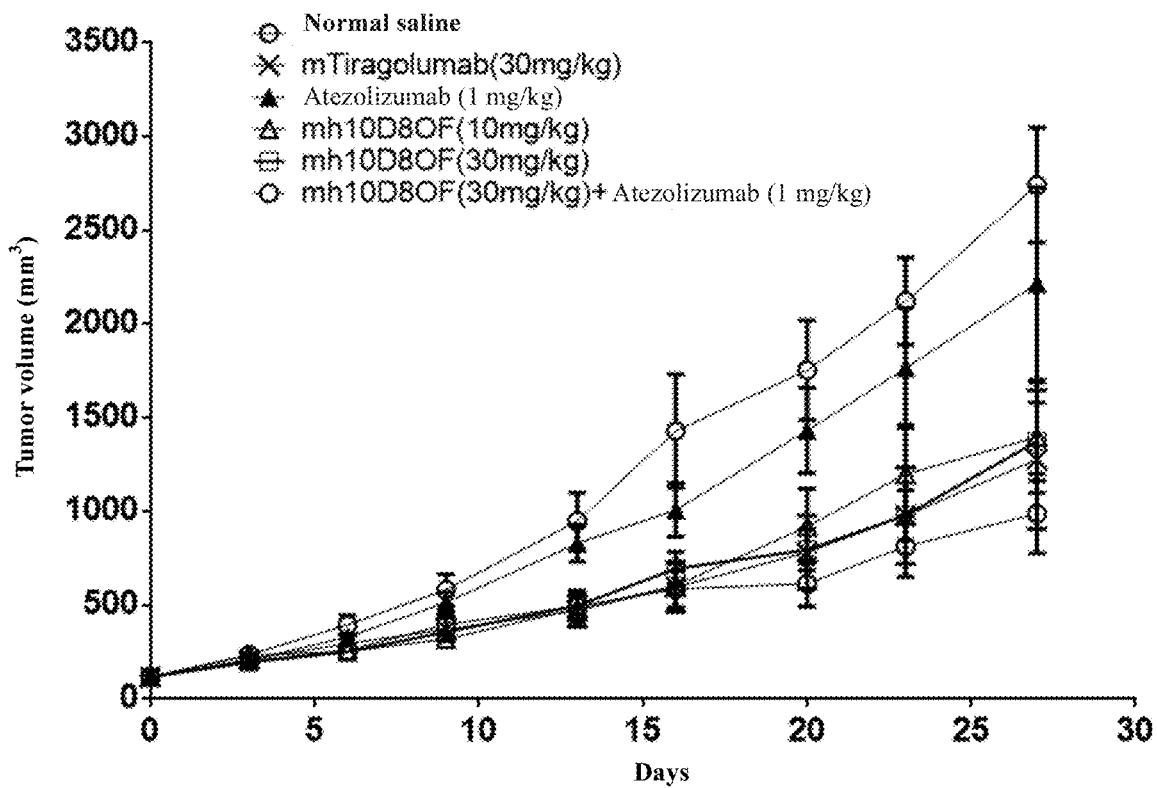
FIG. 32: In vivo pharmacodynamic study. denotes normal saline, denotes mTiragolumab (30 mg/kg), denotes Atezolizumab (1 mg/kg), denotes m10D8OF (10 mg/kg), denotes mh10D8OF (30 mg/kg), and denotes the combination therapy of mh10D8OF (30 mg/kg)+Atezolizumab (1 mg/kg).

B-hTIGIT humanized mice aged 6-8 weeks were selected and each subcutaneously inoculated, in the right dorsal side, with 0.1 mL of MC38-hPD-L1 cells (MC38 cells expressing human PD-L1 with murine PD-L1 knock-out; Biocytogen Beijing Co., Ltd.) resuspended in PBS at a concentration of $5 \times 10^5$ cells/0.1 mL. When the average tumor volume reached 100-150 mm$^3$, mice with proper tumor volume and body weight were selected and distributed evenly into 6 experimental groups of 10. The treatment was given by intraperitoneal injection. The control group received vehicle (normal saline for injection); 2 treatment groups received mh10D8OF at doses of 10 mg/kg and 30 mg/kg; mTiragolumab was administered at 30 mg/kg; the anti-PD-L1 antibody Atezolizumab was administered at 1 mg/kg; the combination group received mh10D8OF at 30 mg/kg and the anti-PD-L1 antibody Atezolizumab at 1 mg/kg. The results are shown in FIG. 32.

It can be seen that mh10D8OF and mTiragolumab can effectively inhibit the tumor growth, the inhibition has no statistical difference, and the TGIs were all above 50%. TGI (tumor growth inhibition) is the inhibitory rate of tumor (volume), and serves as the evaluation of the inhibition of tumor growth by test compound in vivo (i.e., in animal experiments). It can be calculated using the formula (100−T/C×100)%, wherein T is the average relative tumor volume after treatment and C is the average relative tumor volume before treatment. No significant synergy was seen in this study due to the dose settings. However, in a biological sense, at this dose the combination therapy had a much more significant tumor inhibition, with a tumor inhibition rate TGI of 66%.

The invention claimed is:

1. An antibody or a fragment thereof specifically binding to a T cell immunoreceptor with immunoglobulin and immunoreceptor tyrosine-based inhibitory motif domains (TIGIT), wherein the antibody or the fragment thereof comprises a VH CDR1 set forth in SEQ ID NO: 21, a VH CDR2 set forth in SEQ ID NO: 22, a VH CDR3 set forth in SEQ ID NO: 23, a VL CDR1 set forth in SEQ ID NO: 25, a VL CDR2 set forth in SEQ ID NO: 26 or 43, and a VL CDR3 set forth in SEQ ID NO: 27.

2. The antibody or the fragment thereof according to claim 1, further comprising a human Fc region.

3. The antibody or the fragment thereof according to claim 2, wherein the human Fc region comprises an amino acid E at position 356 (EU numbering system).

4. The antibody or the fragment thereof according to claim 2, wherein the human Fc region comprises an amino acid M at position 386 (EU numbering system).

5. The antibody or the fragment thereof according to claim 2, which comprises the amino acid sequence set forth in SEQ ID NO: 28 or 29.

6. The antibody or the fragment thereof according to claim 2, which comprises the amino acid sequence set forth in SEQ ID NO: 30.

7. An antibody or an antigen-binding fragment thereof, comprising a heavy chain variable region comprising an amino acid sequence selected from the group consisting of SEQ ID NOs: 20, 33, 35, 37, 39 and 41, and a light chain variable region comprising an amino acid sequence selected from the group consisting of SEQ ID NOs: 24, 34, 36, 38, 40 and 42.

8. The antibody or the fragment thereof of claim 7, wherein the heavy chain variable region comprises the amino acid sequence set forth in SEQ ID NO: 35 and the light chain variable region comprises the amino acid sequence set forth in SEQ ID NO: 36.

9. The antibody or the fragment thereof according to claim 7, comprising a heavy chain that comprises the amino acid sequence set forth in SEQ ID NO: 28, and a light chain that comprises the amino acid sequence set forth in SEQ ID NO: 30.

10. The antibody or the fragment thereof according to claim 7, comprising a heavy chain that comprises the amino acid sequence set forth in SEQ ID NO: 29, and a light chain that comprises the amino acid sequence set forth in SEQ ID NO: 30.

11. The antibody or the fragment thereof of claim 7, comprising a heavy chain comprising the amino acid sequence set forth in SEQ ID NO: 44, and a light chain comprising the amino acid sequence set forth in SEQ ID NO: 45.

12. The antibody or the fragment thereof according to claim 1, wherein the antibody or the fragment thereof has ADCC activity.

13. A polynucleotide encoding the antibody or the fragment thereof according to claim 1.

14. A method for treating a cancer or an infection in a patient in need, comprising administering to the patient an effective dose of the antibody or the fragment thereof according to claim 1.

15. The method according to claim 14, wherein the cancer is a solid tumor.

16. The method according to claim 14, wherein the cancer is selected from bladder cancer, liver cancer, colon cancer, rectal cancer, endometrial cancer, leukemia, lymphoma, pancreatic cancer, small cell lung cancer, non-small cell lung cancer, breast cancer, urethral carcinoma, head and neck cancer, gastrointestinal cancer, gastric cancer, esophageal cancer, ovarian cancer, renal cancer, melanoma, prostate cancer and thyroid cancer.

* * * * *